US007329667B2

(12) United States Patent
Di Fabio et al.

(10) Patent No.: US 7,329,667 B2
(45) Date of Patent: Feb. 12, 2008

(54) CRF RECEPTOR ANTAGONISTS

(75) Inventors: Romano Di Fabio, Verona (IT); Fabrizio Micheli, Verona (IT); Alessandra Pasquarello, Verona (IT); Yves St. Denis, Verona (IT)

(73) Assignee: Glaxo Group Limited, Middlesex (GB)

( * ) Notice: Subject to any disclaimer, the term of this patent is extended or adjusted under 35 U.S.C. 154(b) by 122 days.

(21) Appl. No.: 10/476,441

(22) PCT Filed: Apr. 30, 2002

(86) PCT No.: PCT/GB02/01981

§ 371 (c)(1),
(2), (4) Date: May 28, 2004

(87) PCT Pub. No.: WO02/087573

PCT Pub. Date: Nov. 7, 2002

(65) Prior Publication Data

US 2004/0235871 A1 Nov. 25, 2004

(30) Foreign Application Priority Data

Apr. 30, 2001 (GB) ................................ 0110566.7
Apr. 30, 2001 (GB) ................................ 0110579.0
Jul. 17, 2001 (GB) ................................ 0117423.4
Feb. 11, 2002 (GB) ................................ 0203203.5

(51) Int. Cl.
*A01N 43/54* (2006.01)
*C07D 239/00* (2006.01)

(52) U.S. Cl. ....................................... 514/267; 544/251

(58) Field of Classification Search ................ 544/251; 514/267

See application file for complete search history.

(56) References Cited

U.S. PATENT DOCUMENTS 6,514,982 B1 * 2/2003 Haddach et al. ............ 514/267
2001/0000340 A1 4/2001 Chen et al.

FOREIGN PATENT DOCUMENTS

| | | |
|---|---|---|
| WO | WO 97/44038 | 11/1997 |
| WO | WO 00/27846 | 5/2000 |
| WO | WO 00/27850 | 5/2000 |
| WO | WO 03/008414 | 1/2003 |

OTHER PUBLICATIONS

Banker, Gilbert S. et al., Modem Pharmaceutics, Marcel Dekker, New York, 1996, pp. 451 and 596.*

Wolff, Manfred E., Burger's Medicinal Chemistry and Drug Discovery, Fifth Ed., vol. 1: Principles and Practice, John Wiley & Sons, 1995, pp. 975-977.*

West, Anthony R., Solid State Chemistry and Its Applications, Wiley, New York, 1988, pp. 358 & 365.*

* cited by examiner

*Primary Examiner*—James O. Wilson
*Assistant Examiner*—Erich A. Leeser
(74) *Attorney, Agent, or Firm*—Laura K. Madden; Loretta Sauermelch; Mary E. McCarthy

(57) ABSTRACT

The present invention relates to tricyclic pyrimidines compounds of formula (I) including stereoisomers, prodrugs and pharmaceutically acceptable salts or solvates thereof, (I)

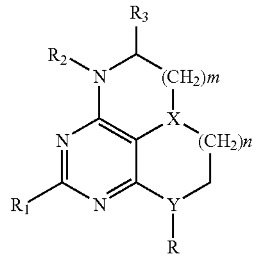

to processes for their preparation, to pharmaceutical compositions containing them and to their use in the treatment of conditions mediated by corticotropin-releasing factor (CRF).

17 Claims, No Drawings

CRF RECEPTOR ANTAGONISTS

The present invention relates to tricyclic derivatives, to processes for their preparation, to pharmaceutical compositions containing them and to their use in therapy.

The first corticotropin-releasing factor (CRF) was isolated from ovine hypothalami and identified as a 41-amino acid peptide (Vale et al., Science 213: 1394-1397, 1981).

CRF has been found to produce profound alterations in endocrine, nervous and immune system function. CRF is believed to be the major physiological regulator of the basal and stress-release of adrenocorticotropic hormone ("ACTH"), Bendorphin, and other propiomelanocortin ("POMC")-derived peptides from the anterior pituitary (Vale et al., Science 213: 1394-1397, 1981).

In addition to its role in stimulating the production of ACTH and POMC, CRF appears to be one of the pivotal central nervous system neurotransmitters and plays a crucial role in integrating the body's overall response to stress.

Administration of CRF directly to the brain elicits behavioral, physiological, and endocrine responses identical to those observed for an animal exposed to a stressful environment.

Accordingly, clinical data suggests that CRF receptor antagonists may be useful in the treatment of the neuropsychiatric disorders manifesting hypersecretion of CRF, and, in particular, may represent novel antidepressant and/or anxiolytic drugs.

The first CRF receptor antagonists were peptides (see, e.g., Rivier et al., U.S. Pat. No. 4,605,642; Rivier et al., Science 224: 889, 1984). While these peptides established that CRF receptor antagonists can attenuate the pharmacological responses to CRF, peptide CRF receptor antagonists suffer from the usual drawbacks of peptide therapeutics including lack of stability and limited oral activity. More recently, small molecule CRF receptor antagonists have been reported.

WO 00/27846 discloses CRF receptor antagonists with the following general formula (A)

(A)

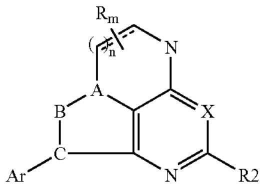

with the proviso that at least one of A, B and C is nitrogen, A, B and C are not all nitrogen and either A-B or B-C is a double bond. A, B and C may be nitrogen or carbon.

Due to the physiological significance of CRF, the development of biologically-active small molecules having significant CRF receptor binding activity and which are capable of antagonizing the CRF receptor remains a desirable goal. Such CRF receptor antagonists would be useful in the treatment of endocrine, psychiatric and neurologic conditions or illnesses, including stress-related disorders in general.

While significant strides have been made toward achieving CRF regulation through administration of CRF receptor antagonists, there remains a need in the art for effective small molecule CRF receptor antagonists. There is also a need for pharmaceutical compositions containing such CRF receptor antagonists, as well as methods relating to the use thereof to treat, for example, stress-related disorders. The present invention fulfills these needs, and provides other related advantages.

In particular the invention relates to novel compounds which are potent and specific antagonists of corticotropin-releasing factor (CRF) receptors.

The present invention provides compounds of formula (I) including stereoisomers, prodrugs and pharmaceutically acceptable salts or solvates thereof (I)

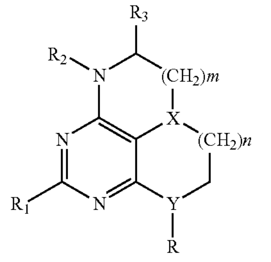

wherein

R is aryl or heteroaryl, wherein each of the above groups R may be substituted by 1 to 4 substituents indendently selected from the group consisting of:

halogen, C1-C6 alkyl, C1-C6 alkoxy, halo C1-C6 alkyl, C2-C6 alkenyl, C2-C6 alkynyl, halo C1-C6 alkoxy, C1-C6 mono or dialkylamino, nitro, cyano and a group $R_4$;

$R_1$ is hydrogen, C1-C6 alkyl, C2-C6 alkenyl, C2-C6 alkynyl, halo C1-C6 alkyl, halo C1-C6 alkoxy, $NH_2$, halogen or cyano;

$R_2$ is hydrogen or $C(H)_n(R_5)_q(CH_2)_pZR_6$;

$R_3$ is hydrogen, C2-C6 alkenyl, C2-C6 alkynyl or $[CH(R_5)(CH_2)_p]_mZR_6$;

$R_4$ is C3-C7 cycloalkyl, which may contain one or more double bonds; aryl; or a 5-6 membered heterocycle;

wherein each of the above groups $R_4$ may be substituted by one or more groups selected from: halogen, C1-C6 alkyl, C1-C6 alkoxy, halo C1-C6 alkyl, C2-C6 alkenyl, C2-C6 alkynyl, halo C1-C6 alkoxy, C1-C6 mon a or dialkylamino, nitro, and cyano;

$R_5$ is hydrogen, C2-C6 alkenyl, C2-C6 alkynyl or $(CH_2)_pZR_6$;

$R_6$ is C1-C6 alkyl, which may be substituted by one or more groups selected from halogen, halo C1-C6 alkyl, C2-C6 alkenyl, C2-C6 alkynyl, halo C1-C6 alkoxy, C1-C6 alkoxy, C1-C6 mono or dialkylamino, nitro, cyano and a group $R_4$;

Y and X are independently carbon or nitrogen;

m and n are independently 0 or 1;

p is 0 or an integer from 1 to 4;

q is 1 or 2;

Z is a bond, O, NH or S.

Acid addition salts of the free base amino compounds of the present invention may be prepared by methods well known in the art, and may be formed from organic and inorganic acids. Suitable organic acids include maleic, malic, fumaric, benzoic, ascorbic, succinic, methanesulfonic, p-toluensulfonic, acetic, oxalic, propionic, tartaric, salicylic, citric, gluconic, lactic, mandelic, cinnamic, aspartic, stearic, palmitic, glycolic, glutamic, and benzenesulfonic acids. Suitable inorganic acids include hydrochloric, hydrobromic, sulfuric, phosphoric, and nitric acids. Thus, the term "pharmaceutically acceptable salt" of structure (I) is intended to encompass any and all acceptable salt forms.

The solvates may, for example, be hydrates.

References hereinafter to a compound according to the invention include both compounds of formula (I) and their pharmaceutically acceptable acid addition salts together with pharmaceutically acceptable solvates.

In addition, prodrugs are also included within the context of this invention. Prodrugs are any covalently bonded carriers that release a compound of structure (I) in vivo when such prodrug is administered to a patient. Prodrugs are generally prepared by modifying functional groups in a way such that the modification is cleaved, either by routine manipulation or in vivo, yielding the parent compound. Prodrugs include, for example, compounds of this invention wherein hydroxy, amine or sulfhydryl groups are bonded to any group that, when administered to a patient, cleaves to form the hydroxy, amine or sulfhydryl groups. Thus, representative examples of prodrugs include (but are not limited to) acetate, formate and benzoate derivatives of alcohol, sulfhydryl and amine functional groups of the compounds of structure (I). Further, in the case of a carboxylic acid (—COOH), esters may be employed, such as methyl esters, ethyl esters, and the like.

With regard to stereoisomers, the compounds of structure (I) may have chiral centers and may occur as recemates, racemic mixtures and as individual enantiomers or diastereomers. All such isomeric forms are included within the present invention, including mixtures thereof. Furthermore, some of the crystalline forms of the compounds of structure (I) may exist as polymorphs, which are included in the present invention.

The term C1-C6 alkyl as used herein as a group or a part of the group refers to a straight or branched alkyl group containing from 1 to 6 carbon atoms; examples of such groups include methyl, ethyl, propyl, isopropyl, n-butyl, isobutyl, tert butyl, pentyl or hexyl.

The term C3-C7 cycloalkyl group means a non aromatic monocyclic hydrocarbon ring of 3 to 7 carbon atom such as, for example, cyclopropyl, cyclobutyl, cyclopentyl, cyclohexyl or cycloheptyl; while unsaturated cycloalkyls include cyclopentenyl and cyclohexenyl, and the like.

The term halogen refers to a fluorine, chlorine, bromine or iodine atom.

The term halo C1-C6 alkyl means an alkyl group having one to six carbon atoms and wherein at least one hydrogen atom is replaced with halogen such as for example a trifluoromethyl group and the like.

The term C2-C6 alkenyl defines straight or branched chain hydrocarbon radicals containing one or more double bond and having from 2 to 6 carbon atoms such as, for example, ethenyl, 2-propenyl, 3-butenyl, 2-butenyl, 2-pentenyl, 3-pentenyl, 3-methyl-2-butenyl or 3-hexenyl and the like.

The term C1-C6 alkoxy group may be a straight or a branched chain alkoxy group, for example methoxy, ethoxy, propoxy, prop-2-oxy, butoxy, but-2-oxy or methylprop-2-oxy and the like.

The term halo C1-C6 alkoxy group may be a C1-C6 alkoxy group as defined before substituted with at least one halogen, preferably fluorine, such as $OCHF_2$, or $OCF_3$.

The term C2-C6 alkynyl defines straight or branched chain hydrocarbon radicals containing one or more triple bond and having from 2 to 6 carbon atoms including acetylenyl, propynyl, 1-butynyl, 1-pentynyl, 3-methyl-1-butynyl and the like.

The term C1-C6 mono or dialkylamino represents an amino group independently substituted with one or two C1-C6 alkyl groups, as defined before.

The term aryl means an aromatic carbocyclic moiety such as phenyl, biphenyl or naphthyl.

The term heteroaryl means an aromatic heterocycle ring of 5- to 10 members and having at least one heteroatom selected from nitrogen, oxygen and sulfur, and containing at least 1 carbon atom, including both mono- and bicyclic ring systems.

Representative heteroaryls include (but are not limited to) furyl, benzofuranyl, thiophenyl, benzothiophenyl, pyrrolyl, indolyl, isoindolyl, azaindolyl, pyridyl, quinolinyl, isoquinolinyl, oxazolyl, isooxazolyl, benzoxazolyl, pyrazolyl, imidazolyl, benzimidazolyl, thiazolyl, benzothiazolyl, isothiazolyl, pyridazinyl, pyrimidinyl, pyrazinyl, triazinyl, cinnolinyl, phthalazinyl, and quinazolinyl.

The term heterocycle means a 5 to 7-membered monocyclic, or 7- to 14-membered polycyclic, heterocycle ring which is either saturated, unsaturated or aromatic, and which contains from 1 to 4 heteroatoms independently selected from nitrogen, oxygen and sulfur, and wherein the nitrogen and sulfur heteroatoms may be optionally oxidized, and the nitrogen heteroatom may be optionally quaternized, including bicyclic rings in which any of the above heterocycles are fused to a benzene ring as well as tricyclic (and higher) heterocyclic rings. The heterocycle may be attached via any heteroatom or carbon atom. Heterocycles include heteroaryls as defined above. Thus, in addition to the aromatic heteroaryls listed above, heterocycles also include (but are not limited to) morpholinyl, pyrrolidinonyl, pyrrolidinyl, piperidinyl, hydantoinyl, valerolactamyl, oxiranyl, oxetanyl, tetrahydrofuranyl, tetrahydropyranyl, tetrahydropyridinyl, tetrahydroprimidinyl, tetrahydrothiophenyl, tetrahydrothiopyranyl, tetrahydropyrimidinyl, tetrahydrothiophenyl, tetrahydrothiopyranyl, and the like.

The term 5-6 membered heterocycle means, according to the above definition, a monocyclic heterocyclic ring which is either saturated, unsaturated or aromatic, and which contains from 1 to 4 heteroatoms independently selected from nitrogen, oxygen and sulfur, and wherein the nitrogen and sulfur heteroatoms may be optionally oxidized, and the nitrogen heteroatom may be optionally quaternized. The heterocycle may be attached via any heteroatom or carbon atom. Thus, the term includes (but is not limited to) morpholinyl, pyrrolidinonyl, pyrrolidinyl, piperidinyl, hydantoinyl, valerolactamyl, oxiranyl, oxetanyl, tetrahydrofuranyl, tetrahydropyranyl, tetrahydropyridinyl, tetrahydroprimidinyl, tetrahydrothiophenyl, tetrahydrothiopyranyl, tetrahydropyrimidinyl, tetrahydrothiophenyl, tetrahydrothiopyranyl, and the like.

Representative compounds of this invention include the following structure (II) and (III)

(II)

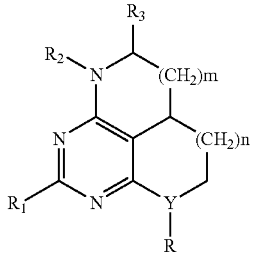

-continued (III)

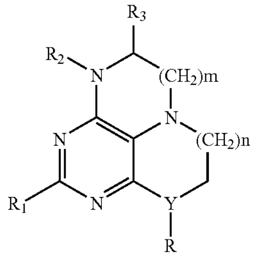

wherein, respectively, X corresponds to a carbon and a nitrogen atom.

Thus, representative compounds of this invention include the following structures (IIa), (IIb), (IIc), (IId), when X corresponds to a carbon atom (IIa)

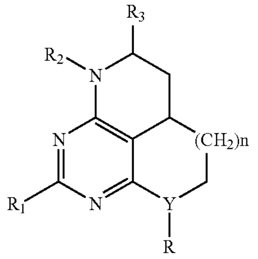

(IIb)

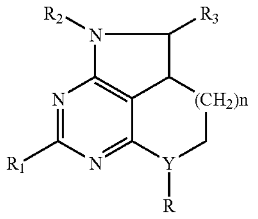

(IIc)

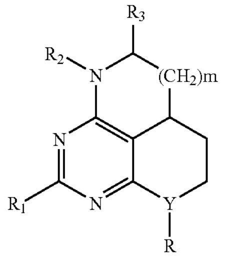

(IId)

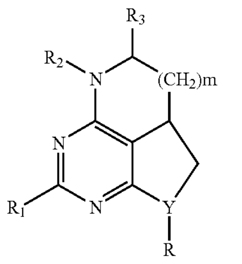

Depending upon the choice of X, the representative compounds of this invention include, but are not limited to, the following compounds (Ia-1), (Ib-1), (Ic-1).

(Ia-1)

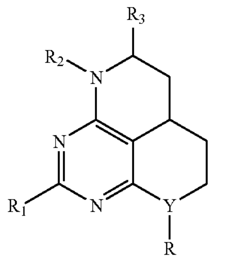

(Ib-1)

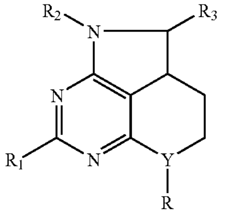

(Ic-1)

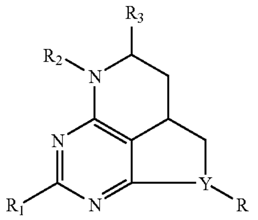

Depending upon the choice of X and Y the representative compounds of this invention include, but are not limited to, the following compounds (I-1), (I-2), (I-3) and (I-4).

(I-1)

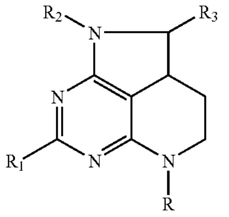

(I-2)

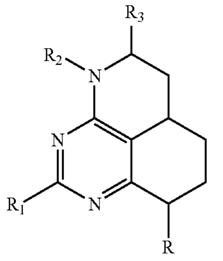

(I-3)

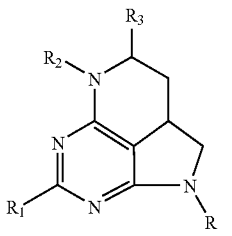

-continued (I-4)

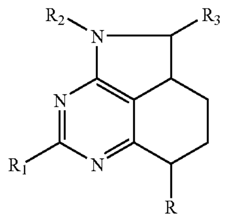

More specific embodiments of the invention include, but are not limited to, compounds of the formula (I); (II), (III), (IIa), (IIb), (IIc), (IId); (Ia-1), (Ib-1), (Ic-1); (I-1), (I-2), (I-3), (I-4): wherein:

$R_2$ and $R_3$ are not simultaneously hydrogen.

Further specific embodiments of the invention include, but are not limited to, compounds of the formula (I); (II), (III), (IIa), (IIb), (IIc), (IId); (Ia-1), (Ib-1), (Ic-1); (I-1), (I-2), (I-3), (I-4): wherein:

$R_1$ is C1-C3 alkyl group or halo C1-C3 alkyl group, preferably methyl or trifluoromethyl.

Preferred embodiments of the invention include, but are not limited to, compounds of the formula (I); (II), (III), (IIa), (IIb), (IIc), (IId); (Ia-1), (Ib-1), (Ic-1); (I-1), (I-2), (I-3), (I-4): wherein:

$R_2$ and $R_3$ are not simultaneously hydrogen; and $R_1$ is C1-C3 alkyl group or halo C1-C3 alkyl group, preferably methyl or trifluoromethyl;

More preferred embodiments of the invention include, but are not limited to, compounds of the formula (I); (II), (III), (IIa), (IIb), (IIc), (IId); (Ia-1), (Ib-1), (Ic-1); (I-1), (I-2), (I-3), (I-4): wherein:

$R_2$ and $R_3$ are not simultaneously hydrogen;

$R_1$ is C1-C3 alkyl group or halo C1-C3 alkyl group, preferably methyl or trifluoromethyl;

R is an aryl group selected from: 2,4-dichlorophenyl, 2-chloro-4-methylphenyl, 2-chloro-4-trifluoromethyl, 2-chloro-4-methoxyphenyl, 2,4,5-trimethylphenyl, 2,4-dimethyl-phenyl, 2-methyl-4-methoxyphenyl, 2-methyl-4-chlorophenyl, 2-methyl-4-trifluoromethyl, 2,4-dimethoxyphenyl, 2-methoxy-4-trifluoromethylphenyl, 2-methoxy-4-chlorophenyl, 3-methoxy-4-chlorophenyl, 2,5-dimethoxy-4-chlorophenyl, 2-methoxy-4-isopropylphenyl, 2-methoxy-4-trifluoromethylphenyl, 2-methoxy-4-isopropylphenyl 2-methoxy-4-methylphenyl, 2-trifluoromethyl-4-chlorophenyl, 2,4-trifluoromethylphenyl, 2-trifluoromethyl-4-methylphenyl, 2-trifluoromethyl-4-methoxyphenyl, 2-bromo-4-isopropylphenyl, 4-methyl-6-dimethylaminopyridin-3-yl, 4-dimethylamino-6-methyl-pyridin-3-yl, 6-dimethylamino-pyridin-3-yl and 4-dimethylamino-pyridin-3-yl.

Preferred compounds according to the invention are:

5-(2,4-dichlorophenyl)-1-(1-ethylpropyl)-7-methyl-1,2,2a,3,4,5-hexahydro-1,5,6,8-tetraaza-acenaphthylene (I-1-1);

5-(2,4-dichlorophenyl)-1-(2-ethylbutyl)-7-methyl-1,2,2a,3,4,5,5a,8b-octahydro-1,5,6,8-tetraazaacenaphthylene (I-1-2);

5-(2,4-dichlorophenyl)-1-(2-methoxy-1-methoxymethyl-ethyl)-7-methyl-1,2,2a,3,4,5,5a,8b-octahydro-1,5,6,8-tetraazaacenaphthylene (I-1-3);

7-methyl-1-(1-propylbutyl)-5-[4-(1,1,2-trifluoroethyl)-2-trifluoromethylphenyl]-1,2,2a,3,4,5-hexahydro-1,5,6,8-tetraazaacenaphthylene (I-1-4);

7-methyl-1-(1-propylbutyl)-5-[4-(1,1,2-trifluoroethyl)-2-trifluoromethylphenyl]-1,2,2a(S),-3,4,5-hexahydro-1,5,6,8-tetraazaacanaphthylene;

7-methyl-1-(1-propylbutyl)-5-[4-(1,1,2-trifluoroethyl)-2-trifluoromethylphenyl]-1,2,2a-(R),3,4,5-hexahydro-1,5,6,8-tetraazazcanaphthylene;

5-(2,4-dichlorophenyl)-7-methyl-1-(1-propylbutyl)-1,2,2a,3,4,5-hexahydro-1,5,6,8-tetraaza-acenaphthylene (I-1-5);

5-(2,4-dichlorophenyl)-7-methyl-1-(1-propylbutyl)-1,2,2a-(S),3,4,5,5a,8b-octahydro-1,5,6,8-tetraazaacenaphthylene;

5-(2,4-dichlorophenyl)-7-methyl-1-(1-propylbutyl)-1,2,2a-(R),3,4,5,5a,8b-octahydro-1,5,6,8-tetraazaacenaphthylene;

9-(2,4-dichlorophenyl)-4-(1-ethylpropyl)-2-methyl-5,6,6a,7,8,9-hexahydro-4H-1,3,4-triazaphenalene (isomer 1) and 9-(2,4-dichlorophenyl)-4-(1-ethylpropyl)-2-methyl-5,6,6a,7,8,9-hexahydro-4H-1,3,4-triazaphenalene (isomer 2) (2-1-1);

5-cyclopropylmethyl-1-(2,4-dichlorophenyl)-7-methyl-1,2,2a,3,4,5-hexahydro-1,5,6,8-tetraazaacenaphthylene (3-1-1);

1-(2,4-dichlorophenyl)-5-(2-methoxyethyl)-7-methyl-1,2,2a,3,4,5-hexahydro-1,5,6,8-tetraaza-acenaphthylene (3-1-2);

1-(2,4-dichlorophenyl)-5-(1-ethylpropyl)-7-methyl-1,2,2a,3,4,5-hexahydro-1,5,6,8-tetraaza-acenaphthylene (3-1-3);

1-(2,4-dichlorophenyl)-5-(2-ethylbutyl)-7-methyl-1,2,2a,3,4,5-hexahydro-1,5,6,8-tetraaza-acenaphthylene (3-1-4);

1-(2,4-dichlorophenyl)-7-methyl-5-(1-propylbutyl)-1,2,2a,3,4,5-hexahydro-1,5,6,8-tetraaza-acenaphthylene (3-1-5);

7-methyl-5-(1-propylbutyl)-1-[4-(1,1,2-trifluoro-ethyl)-2-trifluoromethylphenyl]-1,2,2a,3,4,5-hexahydro-1,5,6,8-tetraazaacenaphthylene (3-1-6);

5-cyclopropylmethyl-1-(2,4-dichlorophenyl)-7-methyl-4-propyl-1,2,2a,3,4,5-hexahydro-1,5,6,8-tetraazaacenaphthylene (3-1-7);

4-butyl-5-cyclopropylmethyl-1-(2,4-dichlorophenyl)-7-methyl-1,2,2a,3,4,5-hexahydro-1,5,6,8-tetraazaacenaphthylene (3-1-8);

5-cyclopropylmethyl-1-(2,4-dichlorophenyl)-7-methyl-4-propoxy-1,2,2a,3,4,5-hexahydro-1,5,6,8-tetraazaacenaphthylene (3-1-9);

4,5-dibutyl-1-(2,4-dichlorophenyl)-7-methyl-1,2,2a,3,4,5-hexahydro-1,5,6,8-tetraaza-acenaphthylene (3-1-10);

5-(2,4-dichlorophenyl)-1-(1-ethylpropyl)-7-methyl-1,2,2a,3,4,5-hexahydro-1,6,8-triaza-acenaphthylene (4-1-1).

Compounds of formula (I), and salts and solvates thereof, may be prepared by the general methods outlined hereinafter. In the following description, the groups R, $R_1$, $R_2$, $R_3$, $R_4$, $R_5$, $R_6$, X, Y, Z, m, n, p and q have the meaning as previously defined for compounds of formula (I) unless otherwise stated.

Compounds of formula (I) when $R_3$ is different from hydrogen and m is 1 are equivalent to compounds of formula (IV), in which G corresponds to the previous meanings of $R_3$ other than hydrogen, may be prepared by reaction of a compound of formula (V), (V)

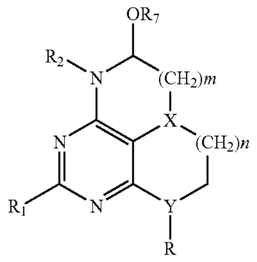

wherein $R_7$ is a C1-C4 linear or branched alkyl group and m is 1, equivalent to compounds of formula (VI). Then compounds of formula (VI) may react with the organo-metallic compound GM,

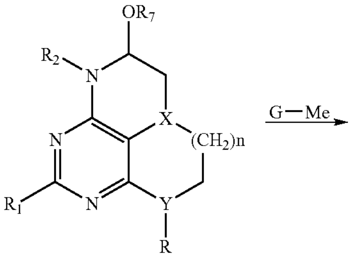

(VI)

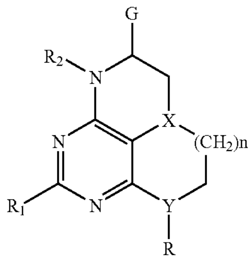

(IV)

wherein M is a metal to give compounds of formula (IV), optionally in the presence of a Lewis acid such as boron-trifluoride etherate. Suitable metals for this reaction include lithium, copper or magnesium.

Compounds of formula (I) when $R_3$ is hydrogen are equivalent to compounds of formula (Ia), may be prepared by reduction of a compound of formula (V) wherein $R_7$ is hydrogen and equivalent to compounds of formula (Va), in the presence of an organic acid (e.g. trifluoroacetic). Convenient reducing agents for this reaction are trialkylsilanes (e.g. triethylsilane). The reaction is preferably carried out in an aprotic solvent such as dichloromethane.

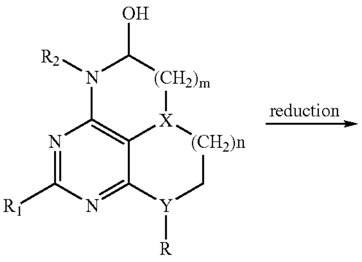

(Va)

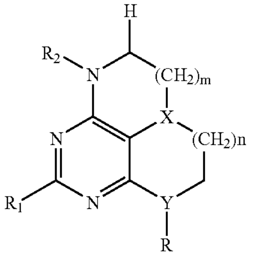

(Ia)

Compounds of formula (IIb), corresponding to compounds of formula (II) in which $R_3$ is hydrogen, may be prepared from compounds of formula (VII) according to the following general Scheme:

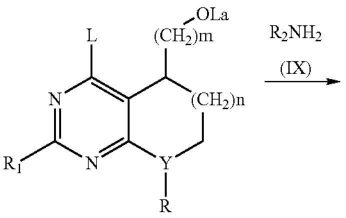

(VII)

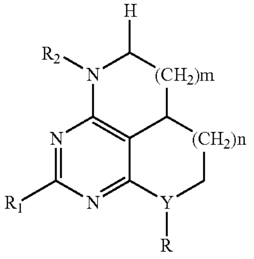

(IIb)

wherein L is a leaving group selected in a group consisted from halogens, preferably chlorine and reactive residue of sulphonic acid (such as mesylate, triflate) and La represents a suitable reactive group able to render OLa a good leaving group (such as mesylate, triflate).

The reaction takes place by heating using the amine $R_2NH_2$ (IX) in excess, preferably as solvent.

Compounds of formula (VI), may be prepared by oxidation of the allyl group of compounds of formula (VIII) to the corresponding aldehyde followed by in situ cyclisation and conversion of the hydroxy group into the alkoxy group which will be described in details later on.

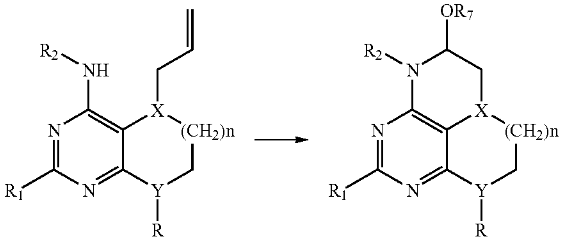

(VIII) (VI)

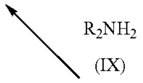

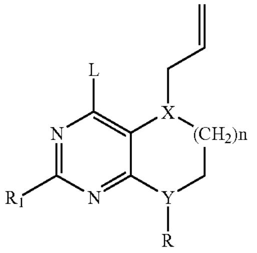

(X)

The oxidation is carried out with osmium tetroxide in the presence of N-methylmorpholine oxide (NMO), followed by treatment with sodium periodate. The reaction is conveniently carried out in a water miscible organic solvent such acetone, tetrahydrofuran optionally in the presence of water.

The conversion of the hydroxy group into C1-C4 alkoxy may be carried out by treatment of the hydroxy group with C1-C4 alcohol in the presence of a suitable inorganic acid, e.g. hydrochloric acid.

Compounds of formula (VIII) may be prepared by treatment of a compound of formula (X), with the amine $R_2NH_2$ (IX).

In an alternative process, compounds of formula (IIa), may be prepared by reaction of a compound of formula (XI), (XI)

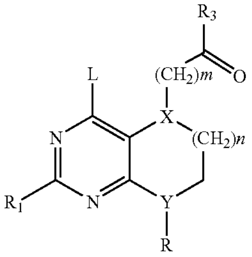

and when m is 1 it is equivalent to a compound of formula (XIa)

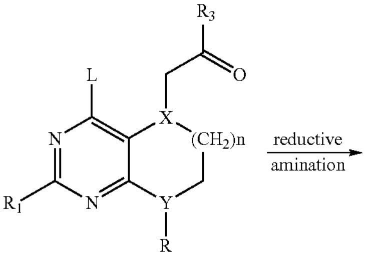

(XIa)

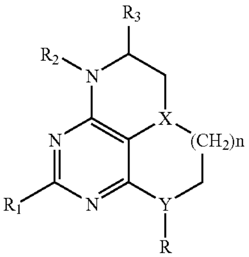

(IIa)

with the amine (IX) in the presence of a suitable reducing agent, followed by in situ cyclisation.

Suitable reducing agents for this reaction include hydride, for example a borane hydride, or a metal hydride complex like lithium aluminum hydride, borohydride, or an organometallic complex such as borane methyl sulphide, 9-borabicyclononane (9-BBN), triethylsilane, sodium triacetoxyborohydride, sodium cyanoborohydride.

Alternatively, boranes may be produced in situ by reacting Sodium Borohydride in the presence of Iodine, an inorganic acid (e.g. sulphoric acid) or an organic acid such as formic acid, trifluoroacetic, acetic acid or methansulphonic acid.

Suitable solvents for this reaction are alcohol (e.g. methanol), ether (e.g. tetrahydrofuran), or halohydrocarbon (e.g. dichloromethane) or an amide (e.g. N,N-dimethylformamide) at a temperature within the range of room temperature to the reflux temperature of the reaction mixture.

Compounds of formula (X) wherein Y is nitrogen and X is carbon are equivalent to compounds of formula (Xa), may be obtained from a compound of formula (XIIa),

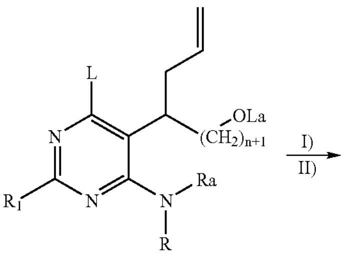

(XIIa)

-continued

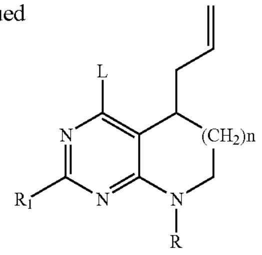

(Xa)

equivalent to compounds of formula (XII)

(XII)

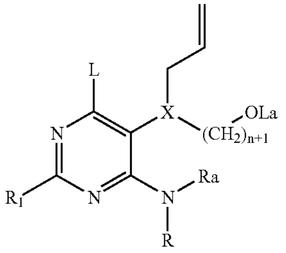

in which X is carbon, La is a suitable reactive group able to render OLa a good leaving group, (such as mesylate) and Ra corresponds to hydrogen or a suitable nitrogen protecting group, if necessary.

Compounds of formula (XIIa) may be subjected to the following reactions:

i) optionally removal of the nitrogen protecting group Ra; and ii) cyclisation in the presence of organic base such as a tertiary amine e.g. triethylamine.

These reactions are preferably carried out in an aprotic solvent such as ether (e.g. tetrahydrofuran), halohydrocarbon such as dichloromethane or amide such as N,N-dimethylformamide.

Compounds of formula (XII) in which X is carbon and n is 0 are equivalent to compounds of formula (XIIa), may be prepared by introduction of the suitable reactive group La on a compound of formula (XIII) in which Hal, Ra, n, are defined as above.

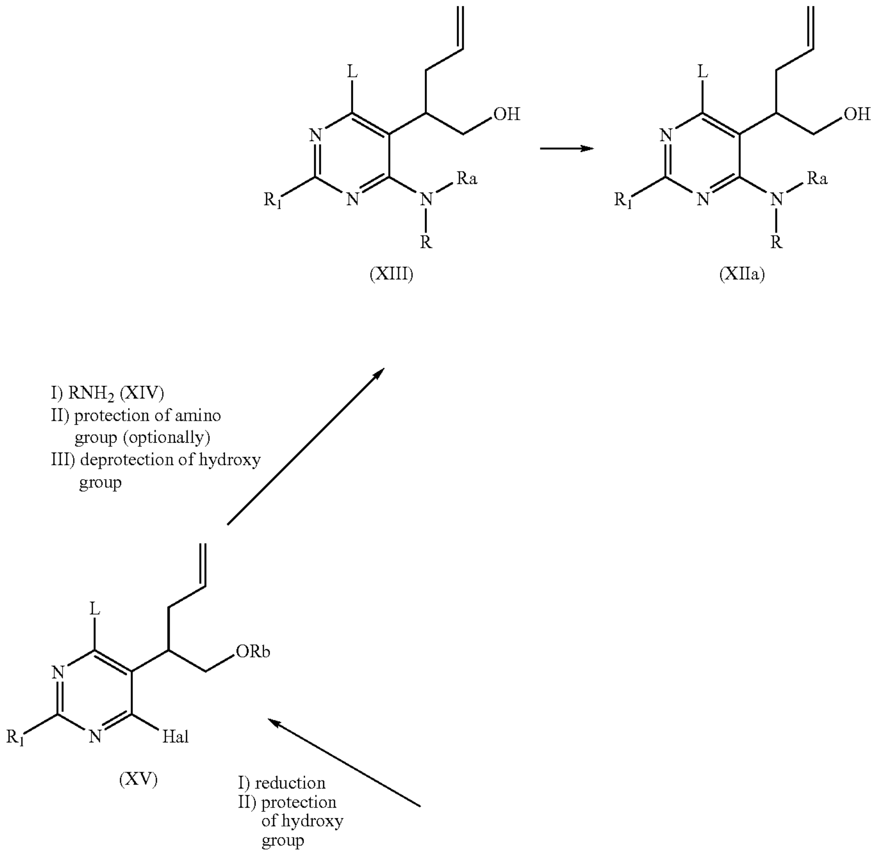

(XIII) (XIIa) (XV)

-continued

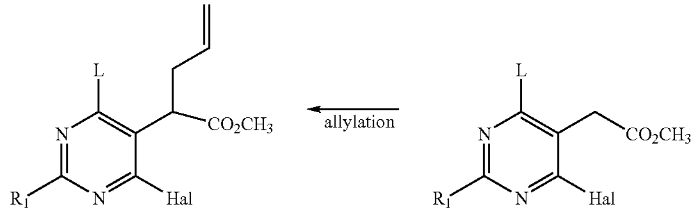

(XVI) (XVII)

Compounds of formula (XIII) may be obtained by reaction of a compound of formula (XV), wherein Rb is a suitable hydroxy protecting group, with amine (XIV), followed by protection of the nitrogen group (if necessary) and removal of hydroxy protecting group.

The reaction with the amine is suitably carried out in an aprotic solvent such as DMF (dimethylformamide) in the presence of a strong base (e.g. sodium hydride).

Compounds of formula (XV) may be prepared by reduction of an ester of formula (XVI) to the corresponding hydroxy with a suitable reducing agent, such as diisobutylaluminumhydride followed by protection of the hydoxy group with a hydroxy suitable protecting group.

Compounds of formula (XVI) may be prepared by reaction of a compound of formula (XVII) with allyl halide (e.g. allyl iodide). The reaction is carried out in the presence of an organic base such as lithiumhexamethyldisilazane at low temperature and in an aprotic solvent (e.g. tetrahydrofuran).

Compounds of formula (XII) wherein n is 1 and X is carbon are equivalent to compounds of formula (XIIb), may be prepared by reduction of a compound of formula (XVIII), with a suitable reducing agent, e.g. sodium borohydride in a solvent such as for example an alcohol (e.g. methanol).

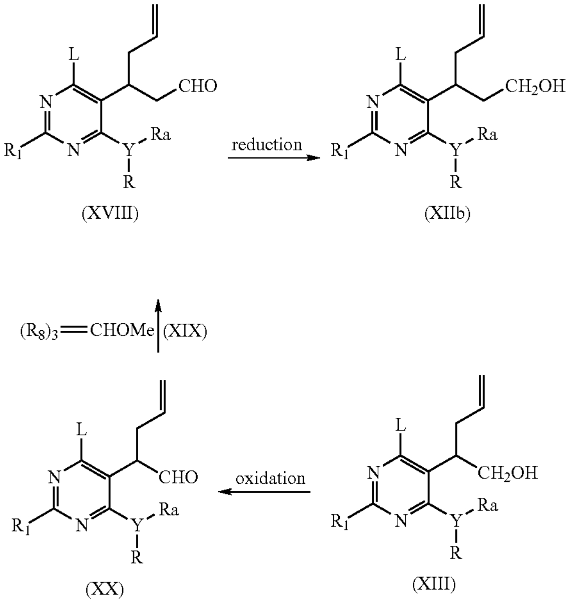

(XVIII) (XIIb)

(XX) (XIII)

Compounds of formula (XVIII) may be prepared by Wittig reaction of a compound of formula (XX) with a phosphorus ylide (XIX), in which $R_8$ is a phenyl derivative, followed by hydrolysis with an acid (e.g hydrochloric acid). The reaction is carried out in an aprotic solvent such as acetonitrile or an ether such as tetrahydrofuran.

Compounds of formula (XX) may also be prepared by oxidation of a compound of formula (XIII). The oxidation may be carried out using the conventional methods known for converting a hydroxy group into an aldehyde group. Thus, for example, the reaction may be carried out using Swern conditions.

Compounds of formula (X) when Y is carbon and X is carbon are equivalent to compounds of formula (Xb), may be prepared by halogenation of a compound of formula (XXI), (XXI)

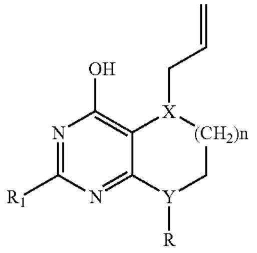

in which, when X and Y are both carbon, is equivalent to a compound of formula (XXIb).

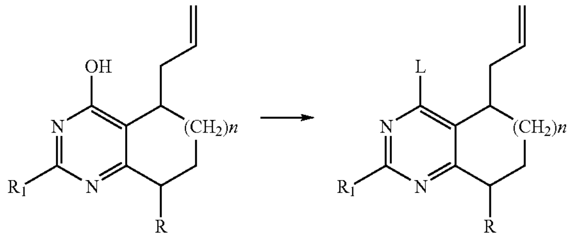

(XXIb) (Xb)

-continued

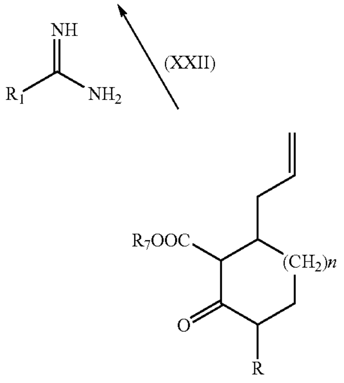

(XXIII)

The halogenation reaction may be carried out using conventional methods known in the art.

Thus for example the reaction may be carried out by treatment with $PO(Hal)_3$, wherein within the halogens, chlorine is preferred.

Compounds of formula (XXIb) may be obtained by reaction of a cyclohexanone of formula (XXIII), in which $R_7$ is defined as before, with a salt (e.g hydrochloride) of acetamidine (XXII).

The reaction is carried out in the presence of a C1-C4 alkaline alkoxylate (e.g. sodium methoxylate), in a solvent such as methyl alcohol.

Compounds of formula (XXIII) when n is 1 are equivalent to compounds of formula (XXIIIa), may be prepared by reaction of a compound of formula (XXIV) with a silane derivative (XXV), wherein $R_7$ is as defined before. The reaction is carried out in the presence of Lewis acid and in an organic solvent.

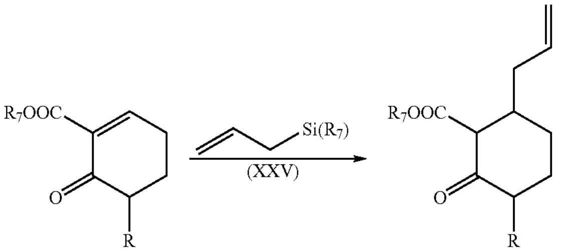

(XXIV) (XXIIIa)

Compounds of formula (XXIII) when n is 0 are equivalent to compounds of formula (XXIIIb), may be prepared by reaction of a compound of formula (XXVI), in which R7 is defined as before and R7' has the same meanings as R7 but not at the same time,

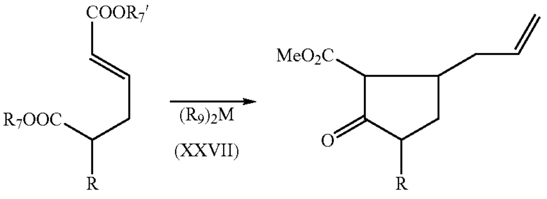

(XXVI) (XXIIIb)

with an organo metallic compound $(R_9)_2M$ (XXVII), in which $R_9$ is an allyl group and M is a metal, optionally in the presence of a Lewis acid such as boron trifluoride etherate. Suitable metals for this reaction include lithium, copper and magnesium.

Compounds of formula (X) when X is nitrogen are equivalent to compound of formula (Xc), may be prepared by reaction of a compound of formula (XXVIII) with allyl halide (e.g. allyl bromide). The reaction is carried out in the presence of an inorganic base such as sodium hydride at low temperature and in aprotic solvent (e.g. tetrahydrofuran or NN-dimethylformamide).

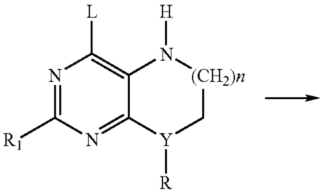

(XXVIII)

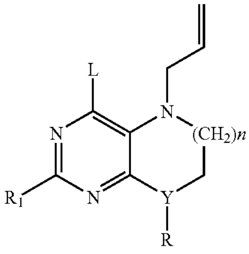

(Xc)

Compounds of formula (XXVIII) when n is 0 and Y is carbon are equivalent to compounds of formula (XXVIIIa), may be prepared by subjecting a compound of formula (XXIX), in which q is as previously defined, (XXIX)

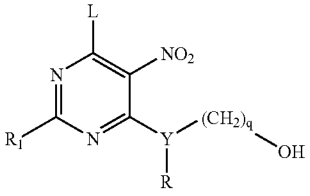

Compounds of formula (XXIXa), corresponding to compounds (XXIX) in which q is 1 and Y is carbon, may be subjected to the following reactions:

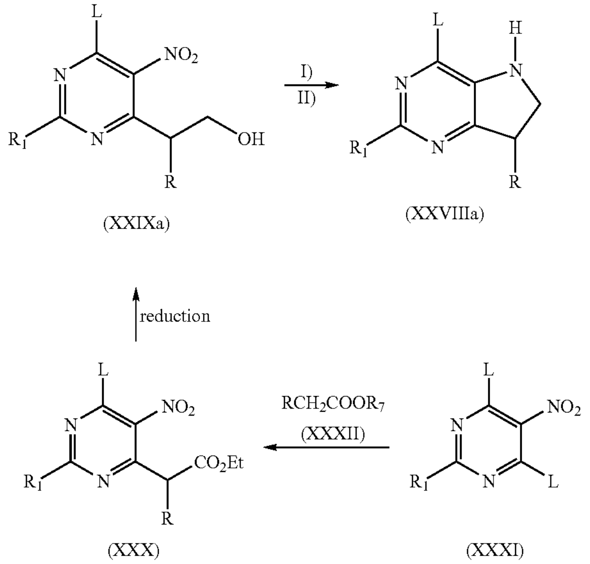

(XXIXa) (XXVIIIa) (XXX) (XXXI)

i) conversion of the hydroxy group into a suitable leaving group such as mesylate, ii) conversion of the nitro group into the amine by reduction in the presence of $Na_2S_2O_4$ and an inorganic base such as potassium carbonate and in situ cyclisation.

Compounds of formula (XXIXa), may be prepared by reduction of an ester compound of formula (XXX). The reduction can be conveniently carried out with sodium borohydride in a protic solvent such alcohol (e.g. methanol or ethanol) and preferably heating e.g. 40-100° C. Compounds of formula (XXX) may be prepared by reaction of a compound of formula (XXXI), with an ester compound (XXXII).

The reaction takes place in an aprotic solvent such as DMF and in the presence of an inorganic base (i.e. sodium hydride).

Compounds of formula (XXIX) when n is 2 and Y is carbon are equivalent to compounds of formula (XXIXb), may be prepared by reduction of compounds of formula (XXXIII) using conventional reducing reagent to convert aldehyde into alcohol. Thus a suitable reducing agent for this reaction is sodium borohydride.

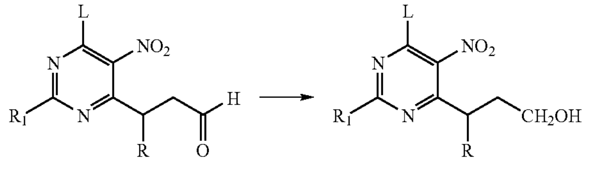

(XXXIII) (XXIXb)

-continued

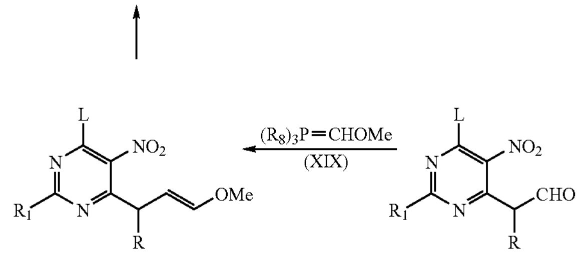

(XXXIV) (XXXV)

Compounds of formula (XXXIII) may be obtained by hydrolysis of enolether of formula (XXXIV). The reaction is preferably carried out in the presence of an inorganic acid such as for example hydrogen chloride. Compounds of formula (XXXIV) may be obtained from (XXXV) by Wittig reaction with the ylide (XIX), in the presence of a suitable organic base like n-BuLi. The reaction is carried out in an aprotic solvent such as acetonitrile or an ether such as tetrahydrofuran. Compounds of formula (XXXV) may be prepared by oxidation of compounds (XXIXa) when Y corresponds to carbon, by using conventional methods known to convert alcohol to aldehyde.

Compounds of formula (XI) when $R_3$ is different from hydrogen are equivalent to compounds of formula (XIb), may be prepared by reaction of a compound of formula (XI) when $R_3$ is hydrogen (equivalent to a compound of formula (XIc)), with the organo metallic compound GMgBr (XXXVI), to give the alcohol compound (XXXVII), which may be oxidised to the keto compound (XIb) according to the following scheme

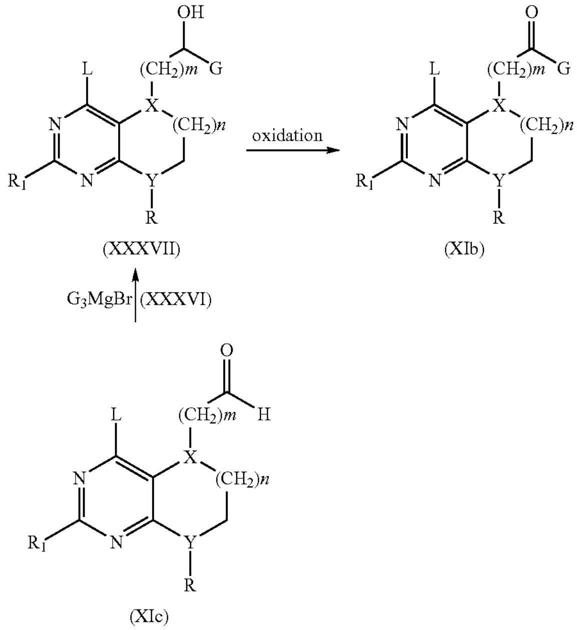

(XXXVII) (XIb) (XIc)

Compounds of formula (XIc) when m is 1 are equivalent to compounds of formula (XId), may be prepared by oxidation of a compound of formula (X).

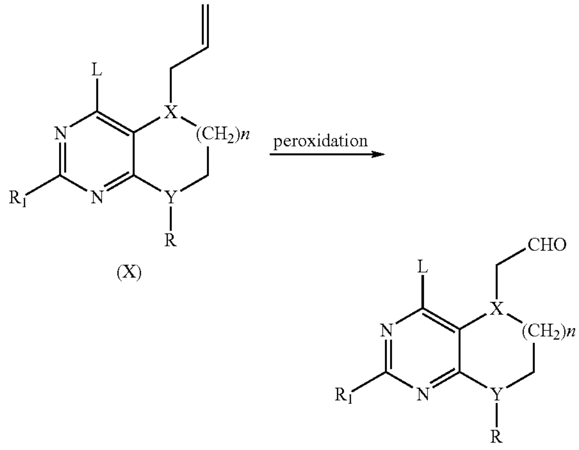

(X)

(XId)

The oxidation reaction is conveniently carried out in the presence of ozone at low temperature e.g. −78° C. in a solvent such as dicholoromethane.

Alternatively, the oxidation takes place by reaction with with osmium tetraoxide in the presence of N-methyl morpholine oxide (NMO) followed by treatment with sodium periodate. The reaction is conveniently carried out in a water miscible organic solvent such as acetone or tetrahydrofuran optionally in the presence of water.

Compounds of formula (XIc) when X and Y are carbon, m is 0 and n is 1 are equivalent to compounds of formula (XIe), may be prepared by treating compounds of formula (XXXVIII) with an inorganic base such as potassium hydroxide in a solvent such as alcohol, followed by reaction with potassium permanganate. The reaction is suitably carried out in water.

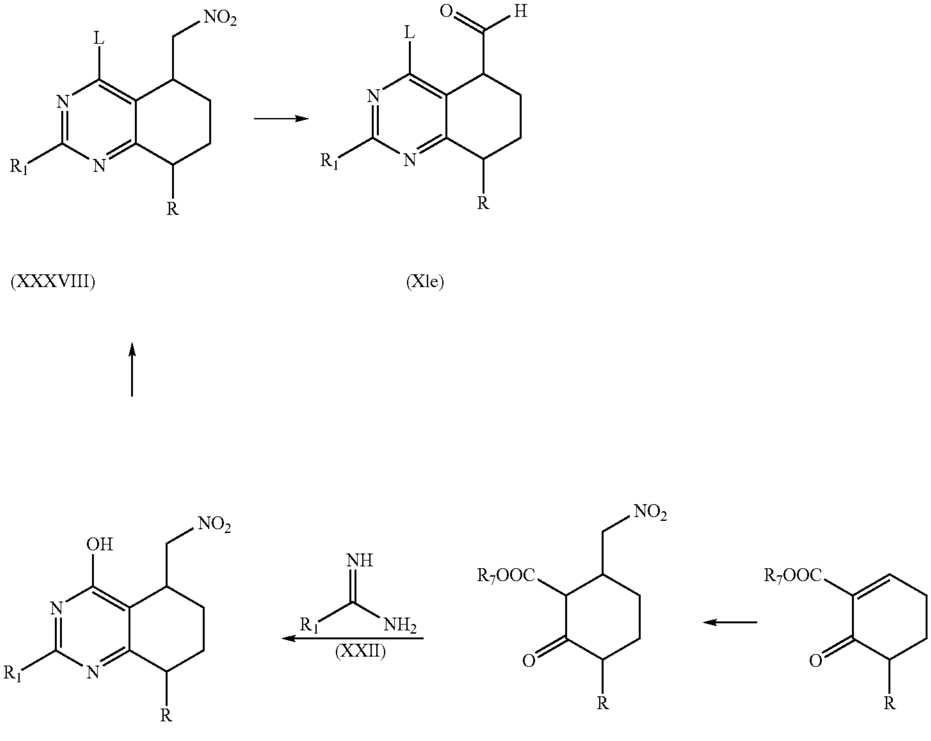

(XXXVIII)

(XIe)

(XXII)

(XXXIX)

(XL)

(XXIV)

Compounds of formula (XXXVII), may be prepared by halogenation of a compound of formula (XXXIX). The halogenation reaction may be carried as described above.

Compounds of formula (XXXIX) may be prepared by reaction of a compound of formula (XL) with a salt (e.g hydrochloric acid) of acetamidine (XXII) using condition as described above. Compounds of formula (XL) may be prepared by reacting compounds of formula (XXIV), in which R7 is as defined before, with nitromethane.

Compounds of formula (XIc) when X is carbon, m is 0, n is 1 and Y is nitrogen are equivalent to compounds of formula (XIf), may be prepared by oxidation of a compound of formula (XLI), using conventional oxidation methods known to convert a hydroxy group into an aldehyde.

i) optionally, removal of the nitrogen protecting group, ii) cyclisation and iii) removal of the hydroxy protecting group Rb.

Compounds of formula (XLII) may be prepared as discussed before by oxidation of a compound of formula (XLIII), followed by reduction to hydroxy group and conversion in a leaving group.

The oxidation reaction is conveniently carried out in the presence of ozone at low temperature e.g. −78° C. in a solvent such as dichloromethane. The reduction is carried out using sodium borohydride as reducing agent.

Compounds of formula (XLIII) may be obtained from a compound of formula (XV) with amine (XIV), followed by protection of the nitrogen group.

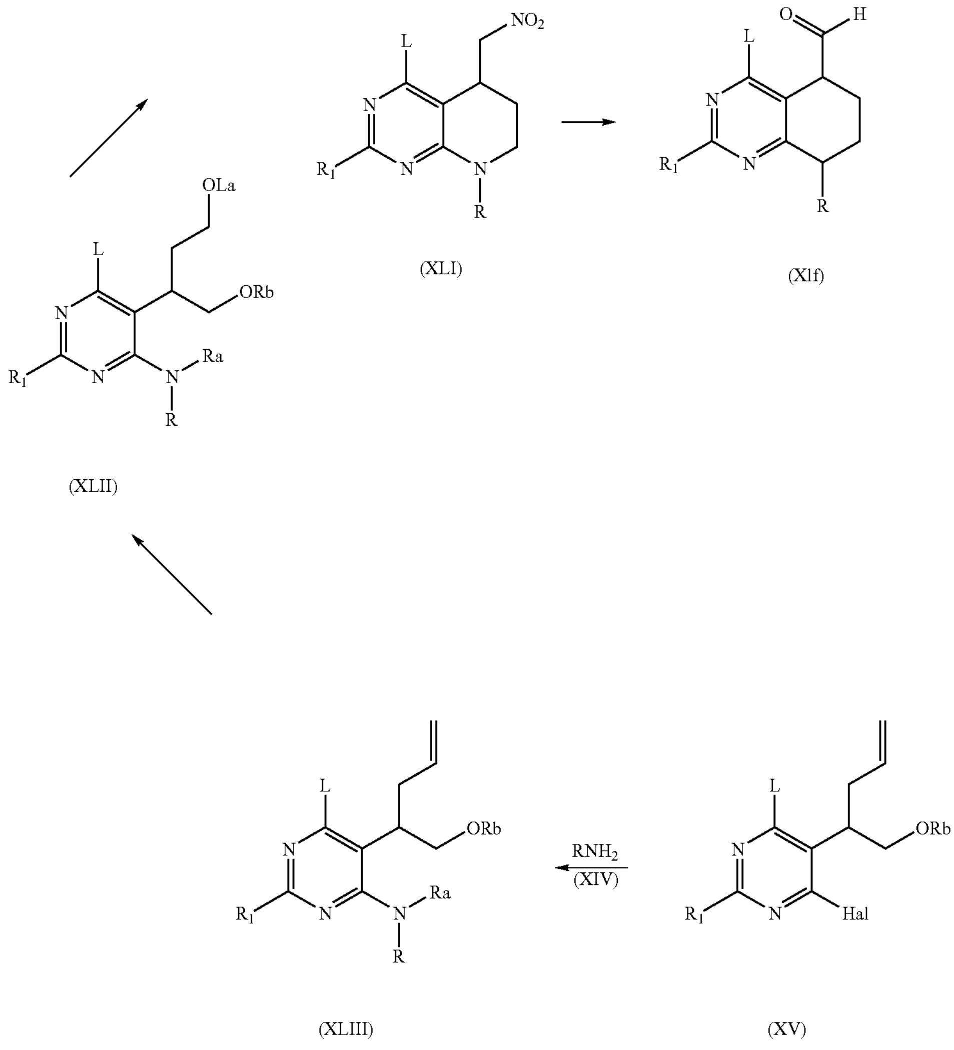

(XLI) (XIf) (XLII) (XLIII) (XV)

Compounds of formula (XLI) may be prepared by subjecting a compound of formula (XLII), wherein La is a suitable leaving group, such as mesylate, Ra and Rb are as defined above, to the following reactions:

Compounds of formula (XLI) may be converted to compounds of formula (VIIa), corresponding to compounds of formula (VII) in which X is carbon, Y is nitrogen m and n are 1, according to known methods.

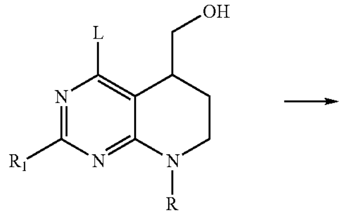

(XLI)

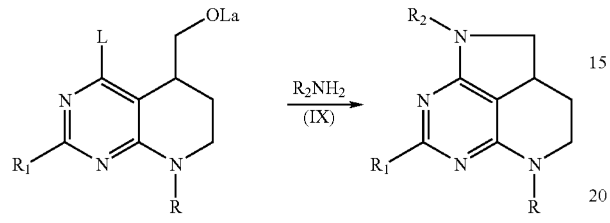

(VIIa) (I-1a)

According to a previous Scheme, compounds of formula (VIIa) may be converted to compound of formula (I-1a), corresponding to compound of formula (I-1) in which $R_3$ is hydrogen.

Compounds of formula (Xc) in which X and Y are nitrogen and n is 1 are equivalent to compounds of formula (Xc'), may be prepared by reaction of a compound of formula (XLIV) with dibromoethane, in the presence of an organic or inorganic base. The reaction is suitably carried out in an aprotic solvent such as NN-dimethylformamide or acetonitrile.

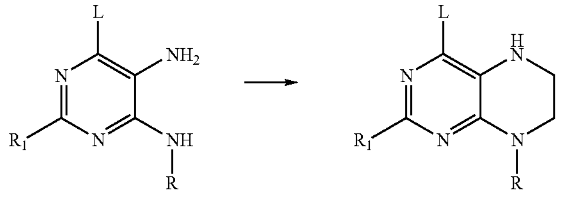

(XLIV) (Xc')

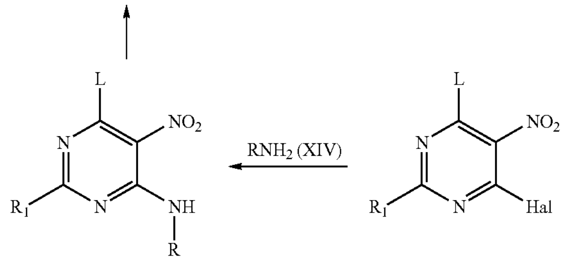

(XLV) (XXXI)

Compounds of formula (XLIV) may be prepared by compounds of formula (XLV) by treatment with iron and an inorganic acid e.g. hydrochloric acid. Compounds of formula (XLV) may be prepared by reaction of compound (XXXI) and the amine (XIV).

Compounds of formula (XVII), (XXIV), (XXVI) and (XXXI) are either known compounds or may be prepared by analogous method to those described for known compounds.

In summary, compounds of formula (I-1a), may be prepared according to the following Scheme 1:

Scheme 1

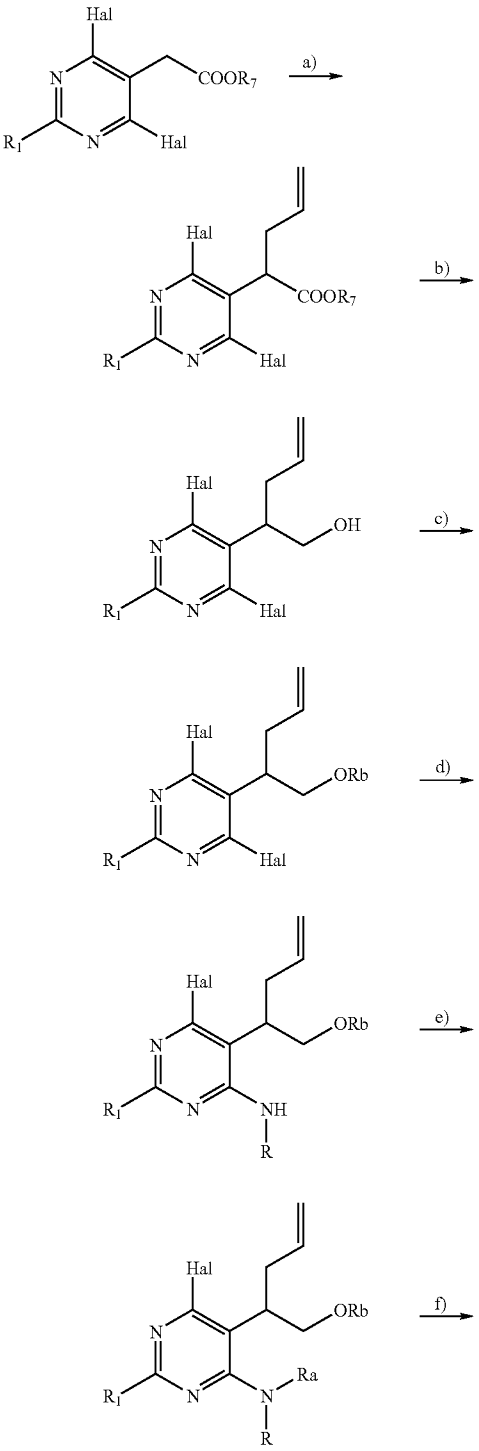

-continued

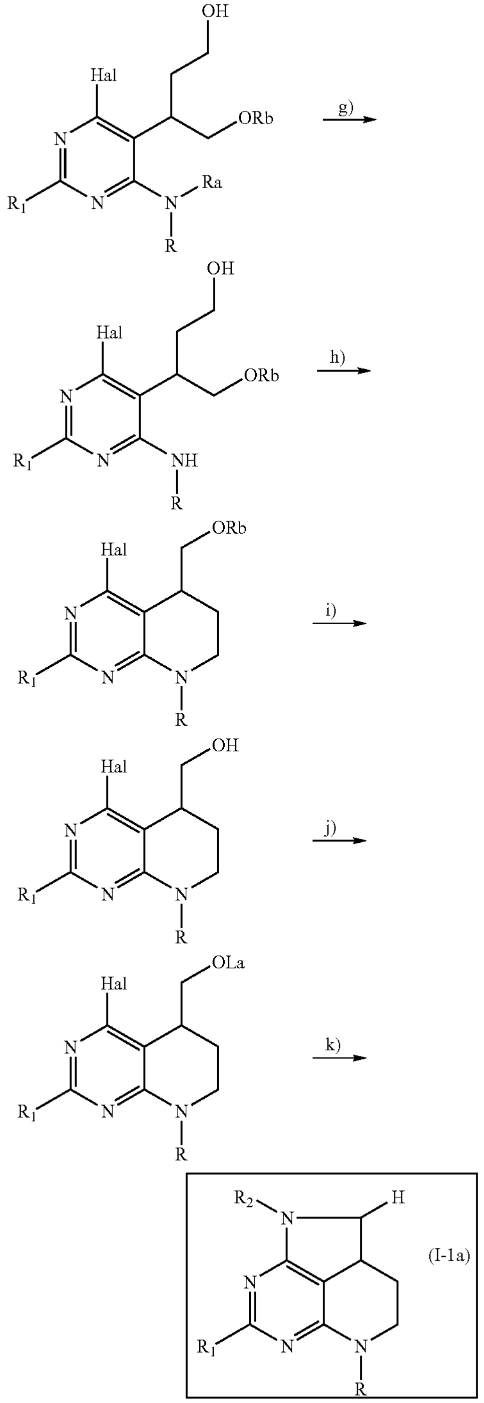

(I-1a)

in which Hal, R, $R_1$, $R_7$, $R_2$, La, Ra and Rb are defined as above and preferably $R_7$ is a methyl group, Hal is chlorine, Ra is t-butylcarbonyl, Rb is t-$BuPh_2$ Si derivative, OLa is a mesyl group and step a stands for allylation with allyl iodide at 0° C. in basic conditions (e.g. LiHMDS); the starting material may be prepared in similar way to what described in Wayne G. C. et al., J. Prakt. Chem., (2000), 342(5), 504-7;

step b stands for reduction of the ester group with a suitable reducing agent, e.g. DIBAl-H, in usual conditions ($CH_2Cl_2$, 0° C. to r.t.);

step c stands for protection of the hydroxy group, preferably with t-$BuPh_2SiCl$, in DMF with DMAP as catalyst (0° C. to r.t);

step d stands for reaction with the amine $RNH_2$ (XIV) as described above;

step e stands for protection of the amino group with a suitale protecting group, for example by treatment with $(BOC)_2O$ in presence of DMAP;

step f stands for, i) oxidation with $OsO_4$ in acetone/water, then ii) treatment with $NaIO_4$ in THF/water, and finally iii) reduction with $NaBH_4$ in a suitable solvent (e.g. EtOH);

step g stands for deprotection of the amino protecting group (e.g. $CF_3CO_2H$ in $CH_2Cl_2$);

step h stands for intramolecular cyclisation, for example by mesylation of the hydroxy group in basic conditions (i.e. $Et_3N$);

step i stands for deprotection of the hydroxy protecting group (e.g. $Et_3N$-3HF in DMF at 40° C.);

step j stands for transformation of the hydroxy group in a suitable leaving group (e.g. mesylation);

step k stands for reaction with the amine (IX) as described above.

Alternatively, the synthesis can be modified following the steps below (starting from an already described intermediate) according to Scheme 2

Scheme 2

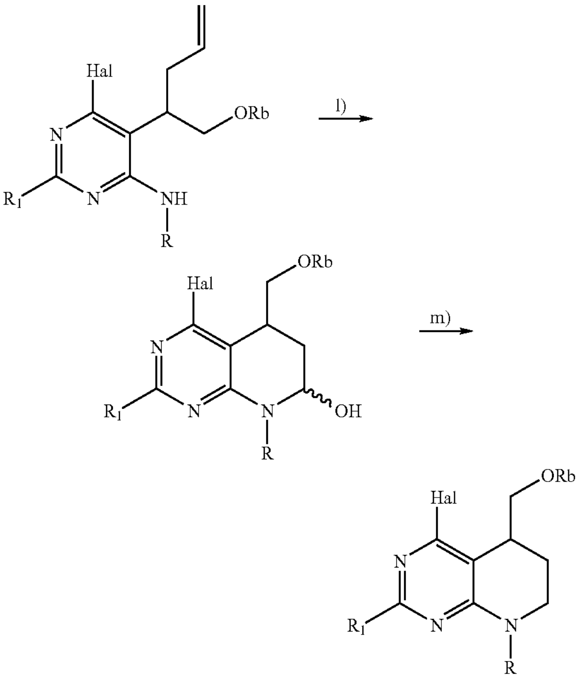

in which step l stands for the first two reactions of previous step f, and step m stands for treatment with $Et_3SiH$ in the presence of $BF_3$-$Et_2O$.

The synthesis is then completed as described in Scheme 1.

In another alternative, the protection of the amino group can be avoided through the following sequence of steps (starting from an already described intermediate) according to scheme 2a Scheme 2a

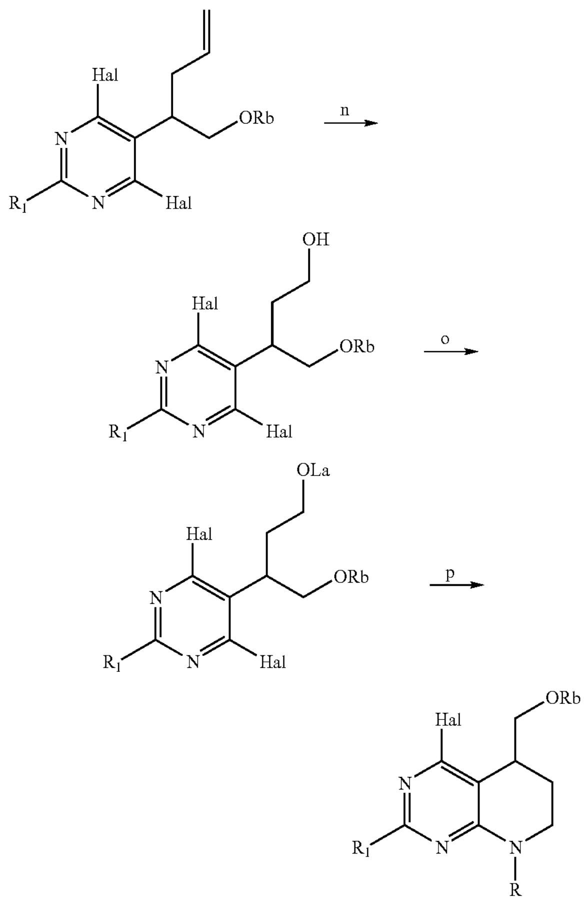

in wich step n corresponds to previous step f);

step o corresponds to previous step j);

step p stands for reaction with the amine $RNH_2$ (XIV) as described above;

The synthesis is then completed as described in Scheme 1.

In another embodiment of the invention, compounds of formula (I-2), in which R3 is hydrogen are equivalent to compounds of formula (I-2a), may be prepared according to the following Scheme 3

Scheme 3

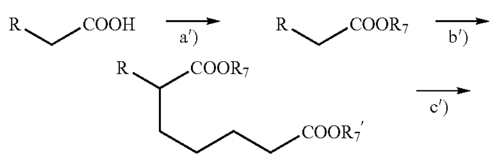

-continued

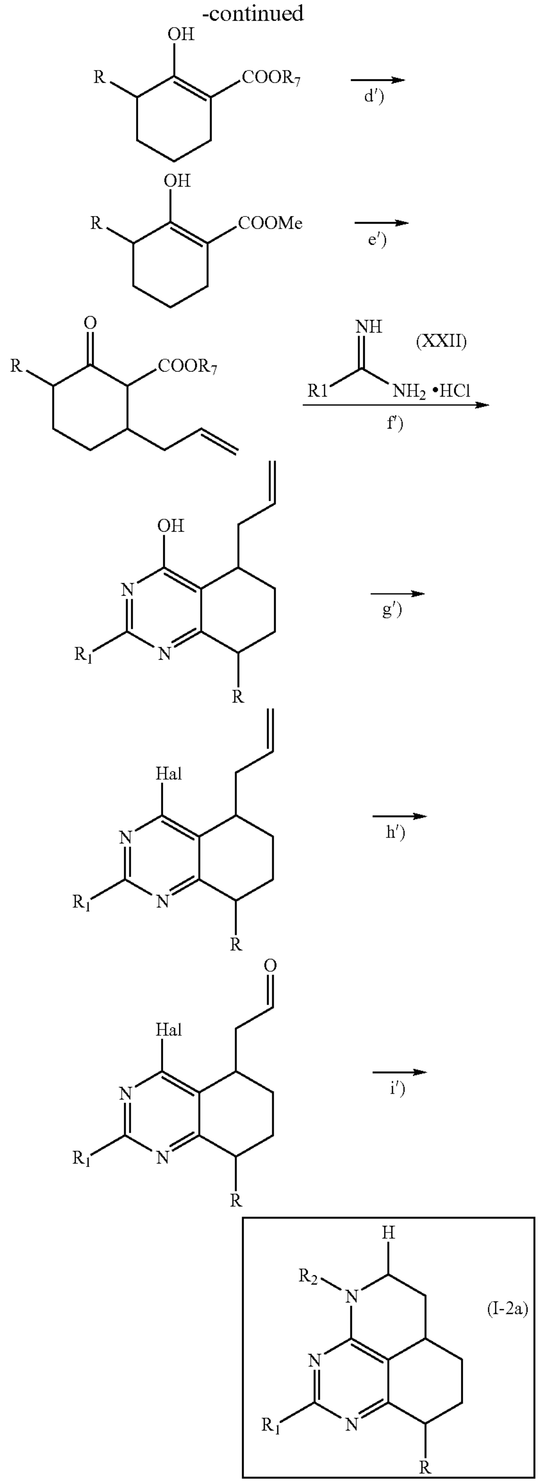

in which Hal, R, $R_1$, $R_2$, $R_7$, Rb are defined as above and preferably $R_7$ is a methyl group, Hal is chlorine, Rb is t-$BuPh_2$ Si derivative, OLa is a mesyl group and step a' stands for esterification in usual conditions ($R_7H$, acid catalyst, reflux);

step b' stands for alkylation with the suitable alkylating agent (e.g. methyl 5-iodovalerate in the presence of LiHMDS);

step c' stands for intramolecular cyclisation in basic conditions (i.e. MeONa, refluxing toluene);

step d' stands for phenylselenylation followed by oxidation with $H_2O_2$ and subsequent elimination;

step e' stands for 1,4-carbonyl addition with a suitable silane such as allyltrimethylsilane catalysed by $TiCl_4$;

step f' stands for reaction with the amidine (XXII) as described above;

step g' stands for halogenation of the hydroxy group (e.g. by treatment with $POCl_3$ at reflux);

step h' stands for oxidative cleavage of the double bond by, for example, ozonization;

step i' stands for reductive amination in the presence of $NaBH_3CN$ with the amine (IX) and subsequent intramolecular cyclisation.

In a further embodiment of the invention, compounds of formula (I-3) in which $R_3$ is hydrogen are equivalent to compounds of formula (I-3a) may be prepared according to Scheme 4

Scheme 4

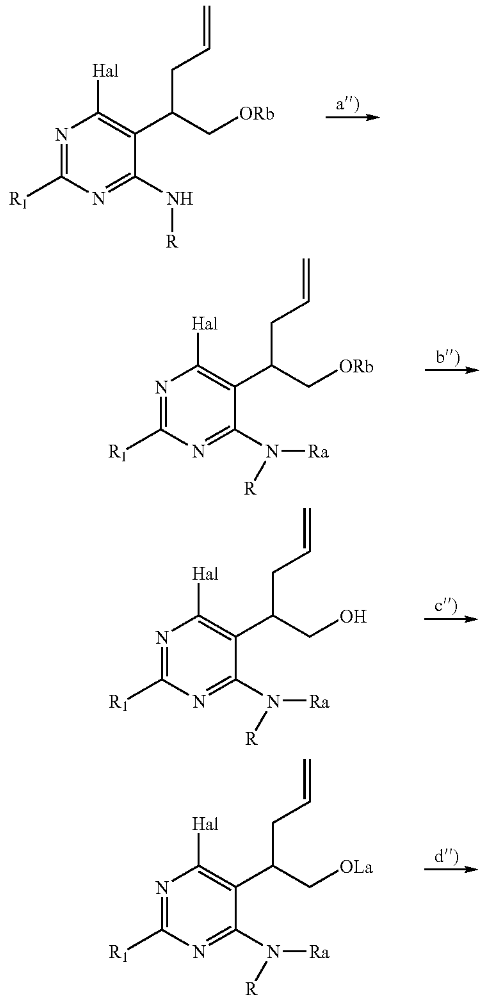

-continued

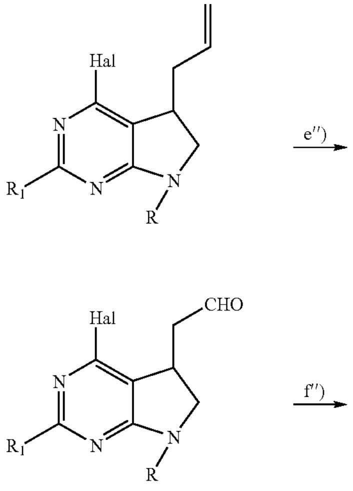

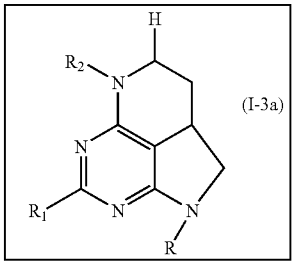

(I-3a)

in which step a'' stands for protection of the amino group with a suitale protecting group, for example by treatment with $(BOC)_2O$ in presence of DMAP;

step b'' corresponds to previous step i);

step c'' stands for mesylation of the hydroxy group in basic conditions (i.e. $Et_3N$);

step d'' stands for deprotection of the protective group of the amino, e.g. by treatment with TFA and then subsequent cyclisation in basic conditions, e.g. $Et_3N$;

step e'' corresponds to previous step h') or corresponds to previous step l);

step f'' corresponds to previous step i');

In another alternative, the last stages of the synthesis could be done as follow and compounds of formula (I-3) in which $R_3$ is different from hydrogen corresponding to compounds of formula (I-3b) according to Scheme 5

Scheme 5

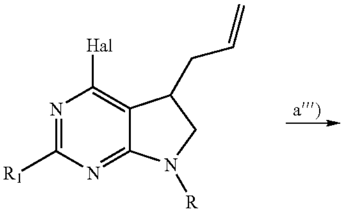

-continued

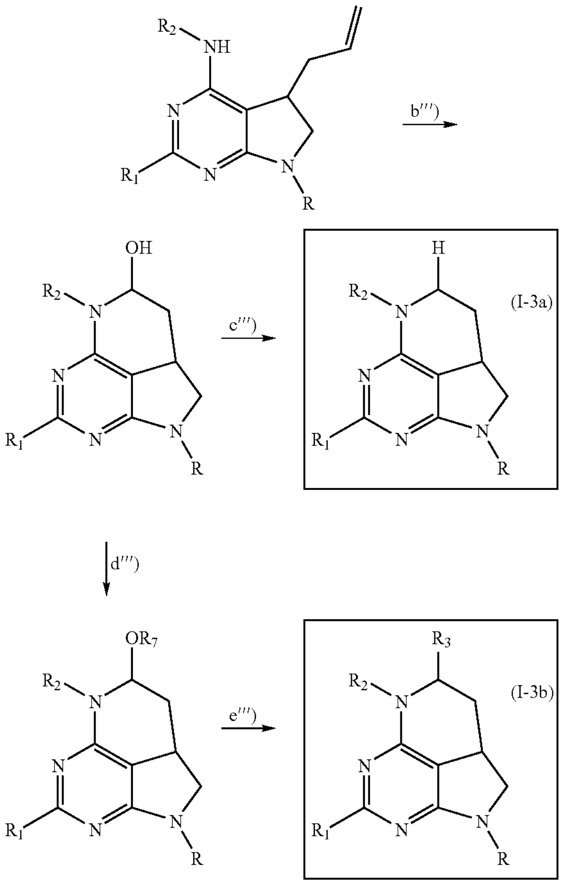

in which step a''' corresponds to previous step k);

step b''' corresponds to previous step l);

step c''' stands for reduction, e.g. by treatment with $Et_3SiH$, TFA;

step d''' stands for formation of the ether group, e.g. by treatment with methanol in presence of PTSA;

step e''' stands for reaction with an organo-metallic compound, such as $R_3Cu$ in presence of $BF_3.Et_2O$.

Alternatively compounds of formula (I-3a), when it is not necessary to protect the amino group, may be prepared as exemplified below in Scheme 6, starting from an already known intermediate:

Scheme 6

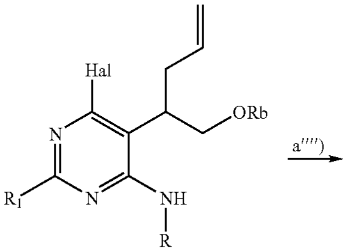

-continued

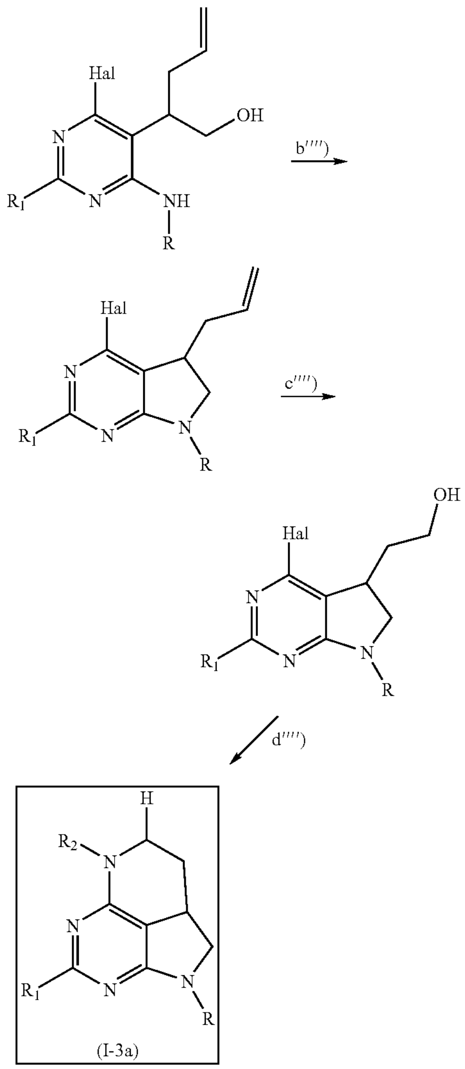

wherein step a'''' corresponds to previous step i);

step b'''' corresponds to previous step j), followed by in situ intramolecular cyclisation;

step c'''' corresponds to previous step f);

step d'''' corresponds to previous steps j) and k).

In another embodiment of the invention, compounds of formula (I-4) when $R_3$ is hydrogen corresponding to compounds of formula (I-4a) may be prepared according to Scheme 7

Scheme 7

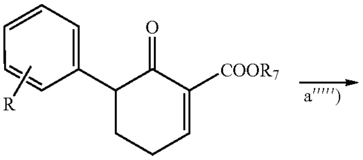

-continued

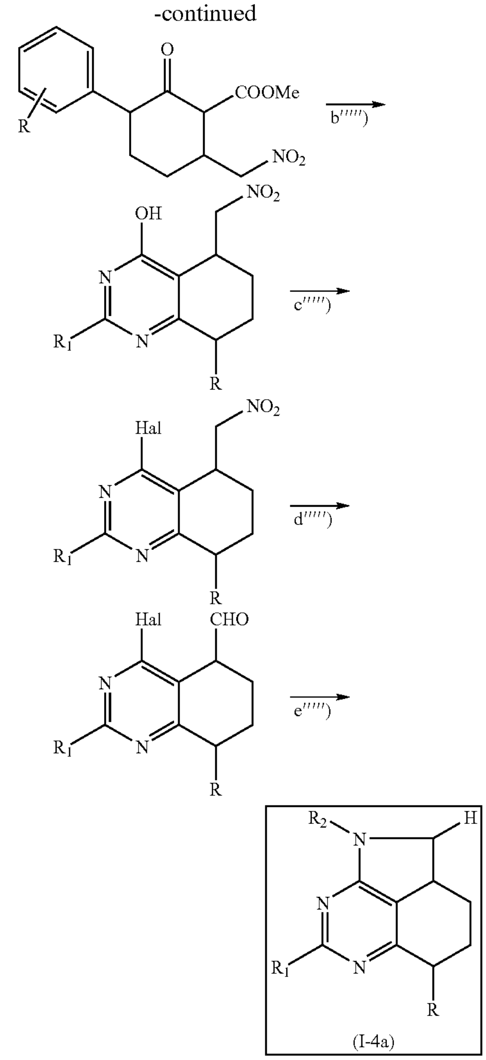

(I-4a)

in which step a''''' stands for reaction with nitromethane in usual conditions;

step b''''' stands for reaction with the amidine (XXII) as described above;

step c''''' corresponds to previous step g');

step d''''' stands for formation of the aldehyde group, e.g. by treatment with KOH in methanol and subsequent oxidation by $KMnO_4$;

step e''''' corresponds to previous step i').

Examples of suitable nitrogen protecting group include alkoxycarbonyl, e.g. t-butoxycarbonyl and arylsulphonyl, e.g phenylsulphonyl.

In any of the above reaction the nitrogen protecting group may be removed by conventional procedures known for removing such groups (such as those described in Protective Groups in Organic Chemistry, pages 46-119, Edited by J F W McOmie (Plenum Press, 1973)). Thus, when Ra is alkoxycarbonyl, the group may be removed by acid hydrolisis using for example trifluoro acetic acid.

Examples of suitable hydroxy protecting group include trihydrocarbyl silyl ethers such as the trimethylsilyl or t-butyldimethylsilyl ether.

The hydroxyl protecting groups may be removed by well-known standard procedures (such as those described in Protective Groups in Organic Chemistry, pages 46-119, Edited by J F W McOmie (Plenum Press, 1973)). For example when Rb is a t-butyldimethylsilyl group, this may be removed by treatment with triethylamine trihydrofluoride.

Pharmaceutical acceptable salts may also be prepared from other salts, including other pharmaceutically acceptable salts, of the compound of formula (I) using conventional methods.

The compounds of formula (I) may readily be isolated in association with solvent molecules by crystallisation or evaporation of an appropriate solvent to give the corresponding solvates.

When a specific enantiomer of a compound of general formula (I) is required, this may be obtained for example by resolution of a corresponding enantiomeric mixture of a compound of formula (I) using conventional methods. Thus the required enantiomer may be obtained from the racemic compound of formula (I) by use of chiral HPLC procedure.

The subject invention also includes isotopically-labeled compounds, which are identical to those recited in formulas I and following, but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorous, fluorine, iodine, and chlorine, such as $^{3}H$, $^{11}C$, $^{14}C$, $^{18}F$, $^{123}I$ and $^{125}I$.

Compounds of the present invention and pharmaceutically acceptable salts of said compounds that contain the aforementioned isotopes and/or other isotopes of other atoms are within the scope of the present invention. Isotopically —labeled compounds of the present invention, for example those into which radioactive isotopes such as $^{3}H$, $^{14}C$ are incorporated, are useful in drug and/or substrate tissue distribution assays. Tritiated, i.e., $^{3}H$, and carbon-14, i.e., $^{14}C$, isotopes are particularly preferred for their ease of preparation and detectability. $^{11}C$ and $^{8}F$ isotopes are particularly useful in PET (positron emission tomography), and $^{125}I$ are particularly useful in SPECT (single photon emission computerized tomography), all useful in brain imaging. Further, substitution with heavier isotopes such as deuterium, i.e., $^{2}H$, can afford certain therapeutic advantages resulting from greater metabolic stability, for example increased in vivo half-life or reduced dosage requirements and, hence, may be preferred in some circumstances. Isotopically labeled compounds of formula I and following of this invention can generally be prepared by carrying out the procedures disclosed in the Schemes and/or in the Examples below, by substituting a readily available isotopically labeled reagent for a non-isotopically labeled reagen.

The CRF receptor antagonists of the present invention demonstrate activity at the CRF receptor site including CRF 1 and CRF 2 receptors and may be used in the treatment of conditions mediated by CRF or CRF receptors.

The effectiveness of a compound as a CRF receptor antagonist may be determined by various assay methods. Suitable CRF antagonists of this invention are capable of inhibiting the specific binding of CRF to its receptor and antagonizing activities associated with CRF. A compound of structure (I) may be assessed for activity as a CRF antagonist by one or more generally accepted assays for this purpose, including (but not limited to) the assays disclosed by DeSouza et al. (J. Neuroscience 7: 88, 1987) and Battaglia et al. (Synapse 1: 572, 1987).

The CRF receptors-binding assay was performed by using the homogeneous technique of scintillation proximity (SPA). The ligand binds to recombinant membrane preparation expressing the CRF receptors which in turn bind to wheatgerm agglutinin coated SPA beads.

In the Experimental Part will be disclosed the details of the experiments.

With reference to CRF receptor binding affinities, CRF receptor antagonists of this invention have a Ki less than 10 μm. In a preferred embodiment of this invention, a CRF receptor antagonist has a Ki of less than 10 μm.

In a more preferred embodiment the value of Ki is less than 1 μm and more preferably less than 0.1 μm. As set forth in greater detail below, the Ki values of representative compounds of this invention were assayed by the methods set forth in Example 5.

Preferred compounds having a Ki of less than 1 μm are compound numbers 3-1-3 and 3-1-10.

More preferred compounds having a Ki less than 0.1 μm are compound numbers 1-1-1, 1-1-4, 1-1-5, 1-2-1, 3-1-5, and 3-1-6.

Compounds of the invention may be useful in the treatment of central nervous system disorders where CRF receptors are involved. In particular in the treatment or prevention of major depressive disorders including bipolar depression, unipolar depression, single or recurrent major depressive episodes with or without psychotic features, catatonic features, melancholic features, atypical features or postpartum onset, the treatment of anxiety and the treatment of panic disorders. Other mood disorders encompassed within the term major depressive disorders include dysthymic disorder with early or late onset and with or without atypical features, neurotic depression, post traumatic stress disorders and social phobia; dementia of the Alzheimer's type, with early or late onset, with depressed mood; vascular dementia with depressed mood; mood disorders induced by alcohol, amphetamines, cocaine, hallucinogens, inhalants, opioids, phencyclidine, sedatives, hypnotics, anxiolytics and other substances; schizoaffective disorder of the depressed type; and adjustment disorder with depressed mood. Major depressive disorders may also result from a general medical condition including, but not limited to, myocardial infarction, diabetes, miscarriage or abortion, etc.

Compounds of the invention are useful as analgesics. In particular they are useful in the treatment of traumatic pain such as postoperative pain; traumatic avulsion pain such as brachial plexus; chronic pain such as arthritic pain such as occurring in osteo-, rheumatoid or psoriatic arthritis; neuropathic pain such as post-herpetic neuralgia, trigeminal neuralgia, segmental or intercostal neuralgia, fibromyalgia, causalgia, peripheral neuropathy, diabetic neuropathy, chemotherapy-induced neuropathy, AIDS related neuropathy, occipital neuralgia, geniculate neuralgia, glossopharyngeal neuralgia, reflex sympathetic dystrophy, phantom limb pain; various forms of headache such as migraine, acute or chronic tension headache, temporomandibular pain, maxillary sinus pain, cluster headache; odontalgia; cancer pain; pain of visceral origin; gastrointestinal pain; nerve entrapment pain; sport's injury pain; dysmennorrhoea; menstrual pain; meningitis; arachnoiditis; musculoskeletal pain; low back pain e.g. spinal stenosis; prolapsed disc; sciatica; angina; ankylosing spondyolitis; gout; burns; scar pain; itch; and thalamic pain such as post stroke thalamic pain.

Compounds of the invention are also useful for the treatment of dysfunction of appetite and food intake and in circumstances such as anorexia, anorexia nervosa and bulimia.

Compounds of the invention are also useful in the treatment of sleep disorders including dysomnia, insomnia, sleep apnea, narcolepsy, and circadian ritmic disorders.

Compounds of the invention are also useful in the treatment or prevention of cognitive disorders. Cognitive disorders include dementia, amnestic disorders and cognitive disorders not otherwise specified.

Furthermore compounds of the invention are also useful as memory and/or cognition enhancers in healthy humans with no cognitive and/or memory deficit.

Compounds of the invention are also useful in the treatment of tolerance to and dependence on a number of substances. For example, they are useful in the treatment of dependence on nicotine, alcohol, caffeine, phencyclidine (phencyclidine like compounds), or in the treatment of tolerance to and dependence on opiates (e.g. cannabis, heroin, morphine) or benzodiazepines; in the treatment of cocaine, sedative ipnotic, amphetamine or amphetamine-related drugs (e.g. dextroamphetamine, methylamphetamine) addiction or a combination thereof.

Compounds of the invention are also useful as anti-inflammatory agents. In particular they are useful in the treatment of inflammation in asthma, influenza, chronic bronchitis and rheumatoid arthritis; in the treatment of inflammatory diseases of the gastrointestinal tract such as Crohn's disease, ulcerative colitis, inflammatory bowel disease (IBD) and non-steroidal anti-inflammatory drug induced damage; inflammatory diseases of the skin such as herpes and eczema; inflammatory diseases of the bladder such as cystitis and urge incontinence; and eye and dental inflammation.

Compounds of the invention are also useful in the treatment of allergic disorders, in particular allergic disorders of the skin such as urticaria, and allergic disorders of the airways such as rhinitis.

Compounds of the invention are also useful in the treatment of emesis, i.e. nausea, retching and vomiting. Emesis includes acute emesis, delayed emesis and anticipatory emesis. The compounds of the invention are useful in the treatment of emesis however induced. For example, emesis may be induced by drugs such as cancer chemotherapeutic agents such as alkylating agents, e.g. cyclophosphamide, carmustine, lomustine and chlorambucil; cytotoxic antibiotics, e.g. dactinomycin, doxorubicin, mitomycin-C and bleomycin; anti-metabolites, e.g. cytarabine, methotrexate and 5-fluorouracil; vinca alkaloids, e.g. etoposide, vinblastine and vincristine; and others such as cisplatin, dacarbazine, procarbazine and hydroxyurea; and combinations thereof; radiation sickness; radiation therapy, e.g. irradiation of the thorax or abdomen, such as in the treatment of cancer; poisons; toxins such as toxins caused by metabolic disorders or by infection, e.g. gastritis, or released during bacterial or viral gastrointestinal infection; pregnancy; vestibular disorders, such as motion sickness, vertigo, dizziness and Meniere's disease; post-operative sickness; gastrointestinal obstruction; reduced gastrointestinal motility; visceral pain, e.g. myocardial infarction or peritonitis; migraine; increased intercranial pressure; decreased intercranial pressure (e.g. altitude sickness); opioid analgesics, such as morphine; and gastro-oesophageal reflux disease, acid indigestion, over-indulgence of food or drink, acid stomach, sour stomach, waterbrash/regurgitation, heartburn, such as episodic heartburn, nocturnal heartburn, and meal-induced heartburn and dyspepsia.

Compounds of the invention are of particular use in the treatment of gastrointestinal disorders such as irritable bowel syndrome (IBS); skin disorders such as psoriasis, pruritis and sunburn; vasospastic diseases such as angina, vascular headache and Reynaud's disease; cerebral ischeamia such as cerebral vasospasm following subarachnoid haemorrhage; fibrosing and collagen diseases such as scleroderma and eosinophilic fascioliasis; disorders related to immune enhancement or suppression such as systemic lupus erythematosus and rheumatic diseases such as fibrositis; and cough.

Compounds of the invention are useful for the treatment of neurotoxic injury which follows cerebral stroke, thromboembolic stroke, hemorrhagic stroke, cerebral ischemia, cerebral vasospam, hypoglycemia, hypoxia, anoxia, perinatal asphyxia cardiac arrest.

The invention therefore provides a compound of formula (I) or a pharmaceutically acceptable salt or solvate thereof for use in therapy, in particular in human medicine.

There is also provided as a further aspect of the invention the use of a compound of formula (I) or a pharmaceutically acceptable salt or solvate thereof in the preparation of a medicament for use in the treatment of conditions mediated by CRF.

In an alternative or further aspect there is provided a method for the treatment of a mammal, including man, in particular in the treatment of condition mediated by CRF, comprising administration of an effective amount of a compound of formula (I) or a pharmaceutically acceptable salt or a solvate thereof.

It will be appreciated that reference to treatment is intended to include prophylaxis as well as the alleviation of established symptoms.

Compounds of formula (I) may be administered as the raw chemical but the active ingredient is preferably presented as a pharmaceutical formulation.

Accordingly, the invention also provides a pharmaceutical composition which comprises at least one compound of formula (I) or a pharmaceutically acceptable salt thereof and formulated for administration by any convenient route. Such compositions are preferably in a form adapted for use in medicine, in particular human medicine, and can conveniently be formulated in a conventional manner using one or more pharmaceutically acceptable carriers or excipients.

Thus compounds of formula (I) may be formulated for oral, buccal, parenteral, topical (including ophthalmic and nasal), depot or rectal administration or in a form suitable for administration by inhalation or insufflation (either through the mouth or nose).

For oral administration, the pharmaceutical compositions may take the form of, for example, tablets or capsules prepared by conventional means with pharmaceutically acceptable excipients such as binding agents (e.g. pregelatinised maize starch, polyvinylpyrrolidone or hydroxypropyl methylcellulose); fillers (e.g. lactose, microcrystalline cellulose or calcium hydrogen phosphate); lubricants (e.g. magnesium stearate, talc or silica); disintegrants (e.g. potato starch or sodium starch glycollate); or wetting agents (e.g. sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g. sorbitol syrup, cellulose derivatives or hydrogenated edible fats); emulsifying agents (e.g. lecithin or acacia); non-aqueous vehicles (e.g. almond oil, oily esters, ethyl alcohol or fractionated vegetable oils); and preservatives (e.g. methyl or propyl-p-hydroxybenzoates or sorbic acid). The preparations may also contain buffer salts, flavouring, colouring and sweetening agents as appropriate.

Preparations for oral administration may be suitably formulated to give controlled release of the active compound.

For buccal administration the composition may take the form of tablets or formulated in conventional manner.

The compounds of the invention may be formulated for parenteral administration by bolus injection or continuous infusion. Formulations for injection may be presented in unit dosage form e.g. in ampoules or in multi-dose containers, with an added preservative. The compositions may take such forms as suspensions, solutions or emulsions in oily or aqueous vehicles, and may contain formulatory agents such as suspending, stabilising and/or dispersing agents. Alternatively, the active ingredient may be in powder form for constitution with a suitable vehicle, e.g. sterile pyrogen-free water, before use.

The compounds of the invention may be formulated for topical administration in the form of ointments, creams, gels, lotions, pessaries, aerosols or drops (e.g. eye, ear or nose drops). Ointments and creams may, for example, be formulated with an aqueous or oily base with the addition of suitable thickening and/or gelling agents. Ointments for administration to the eye may be manufactured in a sterile manner using sterilised components.

Lotions may be formulated with an aqueous or oily base and will in general also contain one or more emulsifying agents, stabilising agents, dispersing agents, suspending agents, thickening agents, or colouring agents. Drops may be formulated with an aqueous or non-aqueous base also comprising one or more dispersing agents, stabilising agents, solubilising agents or suspending agents. They may also contain a preservative.

The compounds of the invention may also be formulated in rectal compositions such as suppositories or retention enemas, e.g. containing conventional suppository bases such as cocoa butter or other glycerides.

The compounds of the invention may also be formulated as depot preparations. Such long acting formulations may be administered by implantation (for example subcutaneously or intramuscularly) or by intramuscular injection. Thus, for example, the compounds of the invention may be formulated with suitable polymeric or hydrophobic materials (for example as an emulsion in an acceptable oil) or ion exchange resins, or as sparingly soluble derivatives, for example, as a sparingly soluble salt.

For intranasal administration, the compounds of the invention may be formulated as solutions for administration via a suitable metered or unitary dose device or alternatively as a powder mix with a suitable carrier for administration using a suitable delivery device.

A proposed dose of the compounds of the invention is 1 to about 1000 mg per day. It will be appreciated that it may be necessary to make routine variations to the dosage, depending on the age and condition of the patient and the precise dosage will be ultimately at the discretion of the attendant physician or veterinarian. The dosage will also depend on the route of administration and the particular compound selected.

Thus for parenteral administration a daily dose will typically be in the range of 1 to about 100 mg, preferably 1 to 80 mg per day. For oral administration a daily dose will typically be within the range 1 to 300 mg e.g. 1 to 100 mg.

EXAMPLES

In the Intermediates and Examples unless otherwise stated:

Melting points (m.p.) were determined on a Gallenkamp m.p. apparatus and are uncorrected. All temperatures refers to ° C. Infrared spectra were measured on a FT-IR instrument. Proton Magnetic Resonance ($^1$H-NMR) spectra were recorded at 400 MHz, chemical shifts are reported in ppm downfield (d) from $Me_4Si$, used as internal standard, and are assigned as singlets (s), doublets (d), doublets of doublets (dd), triplets (t), quartets (q) or multiplets (m). Column chromathography was carried out over silica gel (Merck AG Darmstaadt, Germany). The following abbreviations are used in text: EtOAc=ethyl acetate, cHex=cyclohexane, $CH_2Cl_2$=dichloromethane, $Et_2O$=dietyl ether, DMF=N,N-dimethylformamide, DIPEA=N,N-diisopropylethylamine, MeOH=methanol, $Et_3N$=triethylamine, TFA=trifluoroacetic acid, THF=tetrahydrofuran, DIBAL-H=diisobutylaluminium hydride, DMAP=dimethylaminopyridine, LHMDS=lithium hexamethyldisilazane; Tlc refers to thin layer chromatography on silica plates, and dried refers to a solution dried over anhydrous sodium sulphate; r.t. (RT) refers to room temperature.

Intermediate 1

(4,6-Dichloro-2-methyl-pyrimidin-5-yl)-acetic acid methyl ester

Sodium (1.74 g) was added portionwise to anh. MeOH (60 mL), at 0° C., under $N_2$. After consumption of metallic sodium, acetamidine hydrochloride (7.06 g) was added. After 20 min of stirring, the precipitated NaCl was filtered off. A solution of 2-ethoxycarbonyl-succinic acid diethyl ester (6.04 g) in anh. MeOH (20 mL) was added to the solution of free acetamidine and the mixture was stirred at r.t. for 2 days. The reaction mixture was concentrated to dryness in vacuo and the yellow foam (8.69 g) obtained was then mixed with $POCl_3$ (70 mL) and heated at reflux for 3.5 hr. The resulting solution was cooled to r.t. and poured slowly into ice/water (600 mL) and $NH_4OH$ (50 mL) with vigorous stirring. The product was extracted with EtOAc (3×50 mL) and with $Et_2O$ (3×20 mL). The combined organic extracts were washed with $H_2O$ (60 mL) and brine (40 mL), dried over $Na_2SO_4$, filtered and concentrated in vacuo. The crude oil was purified by flash chromatography (silica gel, cHex/EtOAc 9:1) to give the title compound as a yellow solid (4.27 g).

NMR ($^1$H, $CDCl_3$): δ 5.85 (m, 1H), 5.15 (dq, 1H), 5.11 (dq, 1H), 3.61 (dt, 2H), 2.67 (s, 3H).

MS (m/z): 202 $[M]^+$.2Cl; 167 $[MH-Cl]^+$,1Cl.

Intermediate 2

2-(4,6-Dichloro-2-methyl-pyrimidin-5-yl)-pent-4-enoic acid methyl ester

A solution of intermediate 1 (1.33 g, 5.68 mmol) in anh. THF (8 mL), under $N_2$, was treated with lithium bis(trimethylsilyl) amide (1M solution in hexane, 11.5 mL, 2 eq,) at 0° C. for 15 min before allylbromide (0.99 mL, 2 eq) was added. The mixture was stirred for 4 hr at r.t. and quenched with water (20 mL). The product was extracted with EtOAc (2×15 mL) and the organic phase was washed with $H_2O$ (2×15 mL) and with brine (1×15 mL), dried over $Na_2SO_4$ and concentrated in vacuo. The crude product was purified by flash chromatography (silica gel, EtOAc/cHex 1:9) to give the title compound (673.8 mg) as a white solid.

NMR ($^1$H, $CDCl_3$): δ 5.77 (m, 1H), 5.03 (m, 2H), 4.43 (dd, 1H), 3.76 (s, 3H), 3.12 (m, 1H), 2.78 (m, 1H), 2.73 (s, 3H).

MS (m/z): 374[M]+2Cl.

Intermediate 3

2-(4,6-Dichloro-2-methyl-pyrimidin-5-yl)-pent-4-en-1-ol

To a solution of intermediate 2 (257 mg) in anh. $CH_2Cl_2$ (9.3 mL), at −78° C., under $N_2$, was added DIBAl-H (1M solution in hexane, 5.6 mL, 6 eq). After the addition was complete the reaction mixture was stirred at −78° C. for 1 hr and at 0° C. for 2 hr. The reaction mixture was poured into a solution of HCl 0.5N in ice (20 mL) and extracted with $CH_2Cl_2$ (3×10 mL). The combined organic extracts were dried over anh. $Na_2SO_4$, filtered and concentrated in vacuo to give the title compound (200 mg) as a colourless oil.

NMR ($^1$H, $CDCl_3$): δ 5.76 (m, 1H), 5.12 (m, 1H), 5.01 (m, 1H), 4.16 (m, 1H), 4.06 (m, 1H), 3.91 (m, 1H), 2.8-2.6 (m, 2H), 2.70 (s, 3H), 1.50 (t, 1H).

MS (m/z): 247 $[M]^+$, 2Cl.

Intermediate 4

5-[1-(tert-Butyl-dimethyl-silanyloxymethyl)-but-3-enyl]-4,6-dichloro-2-methylpyrimidine To a solution of intermediate 3 (200 mg) in anh. DMF (12 mL), at 0° C., under $N_2$, was added tert-butyl-dimethylsilylchloride (245 mg, 2 eq) and imidazole (553 mg, 10 eq). The reaction was stirred at r.t. for 2 hr and more tert-butyl-dimethylsilylchloride (61 mg, 0.5 eq) was added. After 1 hr, sat.aq. $NH_4Cl$ (15 mL) and EtOAc (15 mL) were added and the aqueos phase was extracted with additional EtOAc (2×15 mL). The combined extracts were washed with $H_2O$ (10 mL), dried over anh. $Na_2SO_4$, filtered and concentrated in vacuo. The crude product was purified by flash chromatography (silica gel, cHex/EtOAc 19:1) to give the title compound (237 mg) as a colorless oil.

NMR ($^1$H, $CDCl_3$): δ 5.72 (m, 1H), 5.10 (d, 1H), 4.98 (d, 1H), 4.11 (m, 1H), 3.94 (m, 2H), 2.69 (s, 3H), 2.6-2.7 (m, 2H), 0.82 (s, 9H), 0.05 (s, 3H), 0.01 (s, 3H).

MS (m/z): 361 $[M]^+$, 2Cl.

Intermediate 5

{5-[1-(tert-Butyl-dimethyl-silanyloxymethyl)-but-3-enyl]-6-chloro-2-methyl-pyrimidin-4-yl}-(2,4-dichlorophenyl)amine A solution of 2,4-dichloro-aniline (192 mg) in anh. THF (12 mL), under $N_2$, was treated with sodium hydride (80% in mineral oil, 393 mg) at 0° C. for 15 min and then intermediate 4 (434 mg, 1.19 mmol) in anh. THF (4 mL) was added. The mixture was heated to reflux for 3 hr and quenched with water (20 mL). The product was extracted with EtOAc (2×20 mL), dried over anh. $Na_2SO_4$ and concentrated in vacuo. The crude product was purified by flash chromatography (silica gel, EtOAc/cHex 9:1) to give the title compound (419 mg) as a yellow oil.

NMR ($^1$H, $CDCl_3$), T=55° C.: δ 8.35 (bs, 1H), 8.13 (bd, 2H), 7.42 (d, 1H), 7.25 (dd, 1H), 5.73 (m, 1H), 5.03 (m, 2H), 4.10 (dd, 1H), 3.99 (dd, 1H), 3.65 (bm, 1H), 2.75 (m, 2H), 2.47 (s, 3H), 0.82 (s, 9H), 0.01 (s, 3H), 0.00 (s, 3H).

MS (m/z): 486 $[MH]^+$, 3Cl.

Intermediate 6

{5-[1-(tert-Butyl-dimethyl-silanyloxymethyl)-but-3-enyl]-6-chloro-2-methyl-pyrimidin-4-yl}-(2,4-dichlorophenyl)-carbamic acid tert-butyl ester To a solution of intermediate 5 (419 mg) in anh. $CH_2Cl_2$ (17 mL), under $N_2$, was added $(BOC)_2O$ (376 mg, 2 eq) and DMAP (cat). The reaction mixture was stirred at r.t. for 18 hr. The solution was diluted with water (10 ML) and extracted with EtOAc (3×15 mL). The combined organic extracts were dried over anh. $Na_2SO_4$, filtered and concentrated to dryness in vacuo. Flash chromatography of the crude product (silica gel, cHex/EtOAc 9:1) gave the title compound (420 mg) as a yellow solid.

NMR ($^1H$, $CDCl_3$, 40° C.): δ 7.47 (d, 1H), 7.30 (d, 1H), 7.14 (dd, 1H), 5.66 (m, 1H), 5.03-4.89 (m, 2H), 3.98-3.8 (m, 2H), 3.43 (b, 1H), 2.8-2.6 (m, 2H), 2.56 (bs, 3H), 1.41 (s, 9H), 0.77 (s, 9H), −0.02 (s, 3H), −0.10 (s, 3H).

IR (nujol, $cm^{-1}$): 1716.

MS (m/z): 588 $[MH]^{+}$, 3Cl.

Intermediate 7

[6-Chloro-5-(1-hydroxymethyl-but-3-enyl)-2-methyl-pyrimidin-4-yl]-(2,4-dichlorophenyl)-carbamic acid tert-butyl ester To a solution of intermediate 6 (50 mg) in anh. DMF (1 mL), under $N_2$, was added TEA-3HF (21 μl, 1.5 eq). The reaction was stirred at r.t. for 18 hr. The solution was diluted with water (10 mL) and extracted with EtOAc (3×15 mL). The combined organic extracts were dried over anh. $Na_2SO_4$, filtered and concentrated to dryness in vacuo. Flash chromatography of the crude product (silica gel, cHex/EtOAc 8:2) gave the title compound (30 mg) as colourless oil.

NMR ($^1H$, DMSO, T=70° C.): δ 7.69 (d, 1H), 7.43-7.33 (m, 2H), 5.64 (m, 1H), 5.00-4.88 (m, 2H), 4.54 (1H, m), 3.71 (m, 2H), 3.29 (m, 1H), 2.66 (m, 2H), 2.5 (s, 3H), 1.31 (s, 9H).

MS (m/z): 472 $[MH]^+$, 3Cl.

Intermediate 8

Methanesulfonic acid 2-{4-[tert-butoxycarbonyl-(2,4-dichlorophenyl)-amino]-6-chloro-2-methyl-pyrimidin-5-yl}-pent-4-enyl ester To a solution of intermediate 7 (130 mg) in anh. $CH_2Cl_2$ (5.52 mL), at r.t, under $N_2$, was added $Et_3N$ (192 μl, 5 eq) and $CH_3SO_2Cl$ (43 μl, 2 eq). The reaction was stirred at r.t. for 18 hr. The reaction mixture was diluted with water (20 mL) and extracted with EtOAc (3×25 mL). The combined organic extracts were dried over anh. $Na_2SO_4$, filtered and concentrated in vacuo. The crude product was purified by flash chromatography (silica gel, cHex/EtOAc 8:2) to give the title compound (148 mg) as a colourless oil.

NMR ($^1H$, DMSO, T=70° C.): δ 7.72 (d, 1H), 7.36 (dd, 1H), 7.28 (d, 1H), 5.56 (m, 1H), 5.00 (d, 1H), 4.92 (d, 1H), 4.46 (m, 2H), 3.51 (m, 1H), 3.02 (s, 3H), 2.65 (m, 1H), 2.54 (s, 3H), 2.50 (m, 1H), 1.38 (s, 9H).

IR ($cm^{-1}$): 1725, 1641, 1362

MS (m/z): 550 $[MH]^+$, 3Cl

Intermediate 9

5-Allyl-4-chloro-7-(2,4-dichlorophenyl)-2-methyl-6,7-dihydro-5H-pyrrolo[2,3-d]pyrimidine A solution of intermediate 8 (120 mg) in TFA 20%/$CH_2Cl_2$ (7 mL) was stirred at r.t. for 2 hr. To remove TFA, the solvent of the reaction mixture was evaporated in vacuo and repeated additions of $CH_2Cl_2$ and evaporation were made. The crude intermediate was then dissolved in anh. THF (5 mL) and $Et_3N$ (284 μl, 5 eq) was added. After 1 hr of stirring at r.t., $H_2O$ was added and the aqueous layer was extracted with EtOAc (3×10 mL). The combined organic extracts were dried over anh. $Na_2SO_4$, filtered and concentrated to dryness in vacuo to give the title compound (124 mg) as a colourless oil.

NMR ($^1H$, $CDCl_3$): δ 7.49 (dd, 1H), 7.30 (d+s, 2H), 5.77 (m, 1H), 5.16-5.12 (m, 2H), 4.00 (t, 1H), 3.77 (m, 1H), 3.57 (m, 1H), 2.7 (m, 1H), 2.47 (m, 1H), 2.45 (s, 3H).

MS (m/z): 354 $[MH]^+$, 3Cl

Intermediate 10

[4-Chloro-7-(2,4-dichlorophenyl)-2-methyl-6,7-dihydro-5H-pyrrolo[2,3-d]pyrimidin-5-yl]-acetaldehyde A solution of intermediate 9 (30 mg) in $CH_2Cl_2$ (4 mL) was ozonized (5 $g.h^{-1}$) at −78° C. for 5 min. When all the starting material had disappeared (according to TLC in cHex/EtOAc 75/25), the reaction mixture was first flushed with oxygen and then with nitrogen for 20 min. To the cooled reaction mixture was added $(CH_3)_2S$ (25 μl, 4 eq) and the temperature was allowed to warm up to r.t. The solution was stirred for 18 hr at that temperature. The solvent was removed in vacuo and the crude product was purified by flash chromatography (silica gel, cHex/EtOAc 3:1) to give the title compound (8 mg) as a colourless oil.

NMR ($^1H$, $CDCl_3$): δ 9.87 (s, 1H), 7.48 (t, 1H), 7.30 (m, 2H), 4.23 (t, 1H), 3.90 (m, 1H), 3.60 (dd, 1H), 3.29 (dd, 1H), 2.90 (dd, 1H), 2.42 (s, 3H).

MS (m/z): 356 $[MH]^+$, 3Cl.

Intermediate 11

5-[1-(tert-Butyl-diphenyl-silanyloxymethyl)-but-3-enyl]-4,6-dichloro-2-methyl-pyrimidine To a solution of intermediate 3 (152 mg) in anh. DMF (4 mL), at 0° C., under $N_2$, was added DMAP (3.8 mg), imidazole (420 mg) and $Ph_2tBuSiCl$ (0.32 mL). The reaction mixture was stirred at r.t. for 2 hr. To this solution were added 5 mL of sat.aq. $NH_4Cl$ and the mixture was extracted with $Et_2O$ (2×15 mL). The combined organic extracts were washed once with water, once with brine and dried over $Na_2SO_4$. The solids were filtered, the solvent was evaporated and the crude yellow oil was purified by flash chromatography (silica gel, cHex/EtOAc 95:5) to give the title compound as a colourless oil (270 mg).

NMR ($^1H$, $CDCl_3$): δ 7.65 (dd, 2H), 7.56 (dd, 2H), 7.49-7.36 (m, 6H), 5.67 (m, 1H), 5.03 (dd, 1H), 4.94 (dd, 1H), 4.17 (m, 1H), 4.00 (m, 2H), 2.70 (s, 3H), 2.69 (m, 1H), 2.55 (m, 1H), 0.98 (s, 9H).

MS (m/z): 485 $[MH]^+$, 2Cl.

Intermediate 12

{5-[1-(tert-Butyl-diphenyl-silanyloxymethyl)-but-3-enyl]-6-chloro-2-methyl-pyrimidin-4-yl}-(2,4-dichlorophenyl)-amine To a solution of 2,4-dichloroaniline (80 mg) in anh. THF (1 mL), at 0° C., under $N_2$, was added NaH (80% in mineral oil, 31 mg) and left to react at r.t. for 30 min. To this mixture cooled back at 0° C. was added a solution of intermediate 11 (227 mg, 0.467 mmol) in anh. THF (2 mL). The reaction mixture was stirred at reflux for 5 hr. It was then quenched with water (20 mL), and extracted with $Et_2O$ (4×20 mL). The combined organic extracts were washed once with water, once with brine and dried over anh. $Na_2SO_4$. The solids were filtered, the solvent evaporated and the crude orange oil was purified by flash chromatography (silica gel, cHex/EtOAc 95:5) to give the title compound as yellow oil (131.6 mg).

NMR ($^1$H, $CDCl_3$): δ 8.2-7.7 (broad d, 1H), 7.55 (d, 2H), 7.50 (d, 2H), 7.40-7.20 (m, 9H), 5.70 (m, 1H), 5.07 (dd, 1H), 4.94 (dd, 1H), 4.06 (m, 2H), 3.70 (m, 1H), 2.71 (m, 2H), 2.50 (m, 3H), 0.95 (s, 9H).

MS (m/z): 610 $[MH]^+$, 3 Cl.

Intermediate 13

{5-[1-(tert-Butyl-diphenyl-silanyloxymethyl)-but-3-enyl]-6-chloro-2-methyl-pyrimidin-4-yl}-(2,4-dichlorophenyl)-carbamic acid tert-butyl ester To a solution of intermediate 12 (128 mg) in anh. $CH_2Cl_2$ (2 mL), at r.t., under $N_2$, were added $Boc_2O$ (61 mg) and DMAP (3 mg). The reaction mixture was stirred at r.t. for 16 hr. The complete conversion of the starting material was obtained after 2 days by addition of fresh $Boc_2O$ (58 mg+46 mg) and catalytic amounts of DMAP. The reaction mixture was then diluted with water and extracted with $CH_2Cl_2$ (2×5 mL). The combined organic extracts were washed once with water and dried over anh. $Na_2SO_4$. The solids were filtered, the solvent evaporated and the crude yellow oil was purified by flash chromatography (silica gel, cHex/EtOAc 9:1) to give the title compound as pale yellow oil (138 mg).

NMR ($^1$H, DMSO, 70° C.): δ 7.67 (d, 1H), 7.54-7.30 (m, 5H+5H), 7.19 (m, 2H), 5.51 (m, 1H), 4.87 (d, 1H), 4.82 (d, 1H), 3.94 (m, 1H), 3.84 (bm, 1H), 3.53 (m, 1H), 2.57 (s, 3H), 2.62 (m, 1H), 2.35 (m, 1H), 1.35 (s, 9H), 0.90 (s, 9H).

IR (nujol, $cm^{-1}$): 1732.

MS (m/z): 710 $[MH]^+$, 3 Cl, 722 $[M+Na]^+$, 610 $[MH-Boc+H]^+$.

Intermediate 14

{5-[1-(tert-Butyl-diphenyl-silanyloxymethyl)-3-hydroxy-propyl]-6-chloro-2-methyl-pyrimidin-4-yl}-(2,4-dichlorophenyl)-carbamic acid tert-butyl ester A solution of intermediate 13 (108 mg) in 3 mL of $CH_2Cl_2/CH_3OH$ (9:1) was cooled at −78° C. $O_3$ was bubbled in the solution for 30 min under magnetic stirring. $NaBH_4$ (23.1 mg) was then added under $N_2$ atmosphere at low temperature. The reaction mixture was stirred for 3 hr at r.t. It was then quenched with water and extracted with $CH_2Cl_2$ (2×5 mL). The combined organic extracts were washed once with sat.aq. $NH_4Cl$ and dried over anh. $Na_2SO_4$. The solids were filtered, the solvent was evaporated and the crude yellow oil was purified by flash chromatography (silica gel, cHex/EtOAc 9:1) to give the title compound as a colourless oil (59 mg).

NMR ($^1$H, DMSO, 70° C.): δ 7.65 (d, 1H), 7.48-7.34 (m, 5H+5H), 7.28 (d, 1H), 7.12 (bd, 1H), 5.51 (m, 1H), 4.18 (t, 1H), 4.02 (bt, 1H), 3.82 (bm, 1H), 3.51 (m, 1H), 3.29 (bm, 2H), 2.55 (s, 3H), 2.05 (m, 1H), 1.84 (bm, 1H), 1.35 (s, 9H), 0.89 (s, 9H).

IR (film, $cm^{-1}$): 1733.

MS (m/z): 714 $[MH]^+$, 3 Cl, 736 $[M+Na]^+$, 3 Cl, 678 $[MH-HCl]^+$, 2 Cl, 614 $[MH-Boc+H]^+$.

Intermediate 15

Methanesulfonic acid 3-{4-[tert-butoxycarbonyl-(2,4-dichlorophenyl-amino]-6-chloro-2-methyl-pyrimidin-5-yl}-4-(tert-butyl-diphenyl-silanyloxy)-butyl ester To a solution of intermediate 14 (57 mg) in anh. $CH_2Cl_2$ (1 mL), were added $Et_3N$ (55 μl) and MsCl (13 μl) at r.t., under $N_2$. The reaction mixture was stirred for 5 hr, diluted with water and extracted with $CH_2Cl_2$ (2×5 mL). The combined organic extracts were washed once with water, once with brine, and dried over anh. $Na_2SO_4$. The solids were filtered, the solvent evaporated to obtain the crude colourless title compound (60 mg).

NMR ($^1$H, DMSO, 70° C.): δ 7.65 (d, 1H), 7.50-7.34 (m, 5H+5H), 7.24 (bd, 1H), 7.15 (bd, 1H), 4.20-4.00 (m, 3H), 3.80-3.60 (m, 2H), 3.02 (s, 3H), 2.56 (s, 3H), 2.30-2.10 (m, 2H), 1.35 (s, 9H), 0.89 (s, 9H).

IR (nujol, $cm^{-1}$): 1725.

MS (m/z): 794 $[MH]^+$, 3 Cl, 694 $[MH-Boc+H]^+$.

Intermediate 16

Methanesulfonic acid 4-(tert-butyl-diphenyl-silanyloxy)-3-[4-chloro-6-(2,4-dichlorophenyl-amino)-2-methyl-pyrimidin-5-yl]-butyl ester To a solution of intermediate 15 (58 mg) in anh. $CH_2Cl_2$ (1 mL), at r.t., under $N_2$, was added TFA (200 μl, 35 eq). The reaction mixture was stirred for 16 hr, then evaporated under reduced pressure, diluted several times with $CH_2Cl_2$ and evaporated again to obtain the crude title compound (64 mg) as a yellow oil.

MS (m/z): 694 $[MH]^+$, 3 Cl.

Intermediate 17

5-(tert-Butyl-diphenyl-silanyloxymethyl)-4-chloro-8-(2,4-dichlorophenyl)-2-methyl-5,6,7,8-tetrahydro-pyrido[2,3-d]pyrimidine To a solution of intermediate 16 (64 mg) in anh. THF (1 mL), at 0° C., under $N_2$, was added $Et_3N$ (100 μl). The reaction mixture was stirred for 16 hr at r.t., then diluted with water and extracted with $Et_2O$ (2×20 mL). The combined organic extracts were washed once with water, once with brine and dried over anh. $Na_2SO_4$. The solids were filtered, the solvent was evaporated and the crude oil was purified by flash chromatography (silica gel, cHex/EtOAc 95:5) to obtain the title compound as a colourless oil (26.4 mg).

NMR ($^1$H, $CDCl_3$): δ 7.74-6.98 (m, 5H+5H+1H+2H), 4.10-3.90, 3.76-3.55, 3.48-3.28 (m, 5H), 2.58-2.38 (m, 1H), 2.24, 2.22 (s, 3H), 2.1-1.9 (m, 1H), 1.07 (s, 9H).

MS (m/z): 598 $[MH]^+$, 3 Cl.

Intermediate 18

[4-Chloro-8-(2,4-dichlorophenyl)-2-methyl-5,6,7,8-tetrahydro-pyrido[2,3-d]pyrimidine-5-yl]-methanol To a solution of intermediate 17 (22 mg) in anh. DMF (2 mL), at r.t., under $N_2$, was added $Et_3N3HF$ (20 µl). The reaction mixture was stirred for 4 hr at 40° C., then diluted with water and extracted with $Et_2O$ (3×20 mL). The combined organic extracts were washed once with water, once with brine and dried over anh. $Na_2SO_4$. The solids were filtered, the solvent evaporated and the crude oil was purified by flash chromatography (silica gel, cHex/EtOAc 2:1) to give the title compound as colourless oil (13 mg).

NMR ($^1H$, DMSO, 90° C.): δ 7.66 (bs, 1H), 7.50-7.42 (m, 2H), 4.66 (m, 1H), 3.82 (bt, 1H), 3.68 (m, 1H), 3.66-3.36 (m, 2H), 3.20 (m, 1H), 2.33 (m, 1H), 2.14 (s, 3H), 1.94 (m, 1H).

MS (m/z): 358 $[MH]^+$, 3 Cl, 360.

Intermediate 19

Methanesulfonic acid 4-chloro-8-(2,4-dichlorophenyl)-2-methyl-5,6,7,8-tetrahydro-pyrido[2,3-d]pyrimidine-5-ylmethyl ester To a solution of intermediate 18 (13 mg) in anh. $CH_2Cl_2$ (1 mL), at 0° C., under $N_2$, were added $Et_3N$ (20.0 µl) and MsCl (6.0 µl). The reaction mixture was stirred for 16 hr at r.t., then diluted with water and extracted with $CH_2Cl_2$ (3×10 mL). The combined organic extracts were washed once with water, once with brine and dried over anh. $Na_2SO_4$. The solids were filtered and the solvent was evaporated to give the crude title compound (14.7 mg) as a colourless oil.

NMR ($^1H$, $CDCl_3$): δ 7.50 (dd, 1H), 7.40-7.15 (m, 2H), 4.50-4.15 (m, 2H), 3.90-3.70 (m, 1H), 3.65-3.30 (m, 2H), 3.05 (s, 3H), 2.45-2.2 (m, 1H), 2.25 (s, 3H), 2.2-2.0 (m, 1H).

MS (m/z): 438 $[MH]^+$, 3 Cl.

Intermediate 20

5-Iodo-pentanoic acid methyl ester

To a solution of methyl 4-bromovalerate (14 g) in acetone (63 mL), NaI (11.5 g) was added and the mixture was refluxed for 2 hr. It was then cooled to r.t. and the precipitate was filtered. The filtrate was evaporated and ether was added to the residue. The resulting suspension was filtered and the ethereal phase washed with 5% aq $NaHSO_3$ (3×100 mL) and with brine (1×100 mL) and dried over anh. $Na_2SO_4$. The solids were filtered and the solvent evaporated to give the crude title compound as a yellow oil (15.85 g).

NMR ($^1H$, $CDCl_3$): δ 3.68 (s, 3H), 3.19 (t, 2H), 2.34 (t, 2H), 1.86 (m, 2H), 1.74 (m, 2H).

MS (m/z): 242 $[M]^+$, 211 $[M-OMe]^+$, 115 $[M-I]^+$.

Intermediate 21

2-(2,4-dichlorophenyl)-heptanedioic acid dimethyl ester

To a solution of methyl 2,4-dichlorophenylacetate (2 g) in anh. THF (27 mL), at −78° C., under $N_2$, a 1M solution of LHMDS in THF (10.04 mL) was added dropwise and the mixture was stirred at −78° C. for 30 min. Neat intermediate 20 (2.87 g, 1.3 eq) was then added dropwise at −78° C. and the dropping funnel was washed with anh. THF (2 mL). The cooling bath was then removed and the mixture was stirred at r.t. for 3.5 hr. The solvents were evaporated under reduced pressure. The residue was dissolved in ether, washed with water (3×30 mL) and brine (1×30 mL) and dried over anh. $Na_2SO_4$. The solids were filtered and the solvent evaporated. The crude product was purified by flash chromatography (silica gel, cHex/EtOAc 9:1) to give the title compound as a pale yellow oil (2.7 g).

NMR ($^1H$, $CDCl_3$): δ 7.39 (d, 1H), 7.30 (d, 1H), 7.22 (dd, 1H), 4.10 (t, 1H), 3.67 (s, 3H), 3.65 (s, 3H), 2.29 (t, 2H), 2.05 (m, 1H), 1.74 (m, 1H), 1.64 (m, 2H), 1.40-1.20 (m, 2H).

IR (film, $cm^{-1}$): 1738.

MS (m/z): 332 $[M]^+$, 300 $[M-CH_3OH]^+$, 159.

Intermediate 22

3-(2,4-Dichlorophenyl)-2-hydroxy-cyclohex-1-enecarboxylic acid methyl ester

Sodium (0.7 g) was added portionwise under vigorous stirring, at 0° C., under $N_2$, to anh. MeOH (26 mL). After consumption of metallic sodium, anh. toluene (100 mL) was added and a MeOH/toluene mixture (36 mL) was distilled off by means of a Dean-Stark apparatus. The mixture was allowed to cool to r.t. before adding a solution of intermediate 21 (2.52 g) in anh. toluene (1 mL). The mixture was refluxed for 3.5 hr and then cooled to r.t. before acidifying with AcOH. The organic phase was washed with water. The aqueous phase was extracted with EtOAc (2×20 mL) and the combined organic extracts were washed with water (2×20 mL), brine (2×20 mL) and dried over anh. $Na_2SO_4$. The solids were filtered and the solvent evaporated. The crude product was purified by flash chromatography (silica gel, cHex/EtOAc 95:5) to obtain the title compound (colourless oil: 1.8 g)

NMR ($^1H$, $CDCl_3$): δ 12.19 (s, 1H), 7.40 (d, 1H), 7.19 (dd, 1H), 7.08 (d, 1H), 4.07 (t, 1H), 3.81 (s, 3H), 2.35 (m, 2H), 2.01 (m, 1H), 1.73 (m, 1H), 1.60 (m, 2H).

MS (m/z): 300 $[M]^+$, 265, 233.

Intermediate 23

5-(2,4-Dichlorophenyl)-6-oxo-cyclohex-1-enecarboxylic acid methyl ester

Phenylselenenylchloride (2.44 g) was placed in a two-necked flask under nitrogen and dissolved in anh. $CH_2Cl_2$ (21 mL). The brown solution was cooled to 0° C. and anh. pyridine (0.9 mL) was added resulting in a yellow solution which was stirred at 0° C. for 30 min. A solution of intermediate 22 (1.5 g) in anh. $CH_2Cl_2$ (12 mL) was added dropwise at 0° C. and the reaction mixture was stirred at r.t. for 4.5 hr. The reaction mixture was then transfered to a separatory funnel and washed with 1M HCl (2×10 mL) and with water (3×10 mL). The $CH_2Cl_2$ layer was then transfered to a flask and cooled to 0° C. Aqueous $H_2O_2$ (30% w/w, 3 mL) was added and the mixture was stirred for 10 min at 0° C. followed by addition of a second aliquot of $H_2O_2$ (3 mL). The reaction mixture turned colourless and a white solid formed. After 20 min at 0° C. the mixture was washed with sat.aq. $NaHCO_3$ (2×10 mL) and brine (1×10 mL) and dried over anh. $Na_2SO_4$. The solids were filtered and the solvent evaporated to give the title compound (1.45 g) as a pale yellow oil, which becomes solid by cooling.

NMR ($^1H$, $CDCl_3$): δ 7.77 (m, 1H), 7.43 (d, 1H), 7.24 (dd, 1H), 7.11 (d, 1H), 4.12 (dd, 1H), 3.83 (s, 3H), 2.70 (m, 2H), 2.40-2.20 (m, 2H).

IR (film, $cm^{-1}$): 1737, 1673.

MS (m/z): 298 $[M]^+$, 263 $[M-Cl]^+$, 126.

Intermediate 24

5-Allyl-8-(2,4-dichlorophenyl)-2-methyl-5,6,7,8-tetrahydroquinazolin-4-ol

To a solution of intermediate 23 (690 mg) in anh. $CH_2Cl_2$ (6.5 mL), at −78° C., $TiCl_4$ (0.255 mL) was added. The resulting brown solution was stirred at −78° C. for 5 min, after which a solution of allyltrimethylsilane (0.440 mL) in anh. $CH_2Cl_2$ (6.5 mL) was added. After stirring for 1.5 hr at −78° C., the reaction was quenched with water, diluted with $CH_2Cl_2$ and the mixture was allowed to warm to r.t. The aqueous layer was extracted with $CH_2Cl_2$ and the organic phase was washed with brine (1×10 mL) and dried over anh. $Na_2SO_4$. The solids were filtered and the solvent evaporated to obtain the allylated compound (676 mg) as pale yellow oil and as a mixture of diastereoisomeric enolesters and ketoesters.

Sodium (140 mg, 3 eq) was added portionwise to anh. MeOH (6 mL) under $N_2$. After consumption of metallic sodium, acetamidine hydrochloride (600 mg) was added. After 10 min of stirring, the precipitated NaCl was filtered off and washed with anh. MeOH (2 mL). The solution of free acetamidine was added to the crude allylated product (676 g) and the mixture was stirred at r.t. for 18 hr. The solvent was evaporated and the crude product was purified by flash chromatography (silica gel, $CH_2Cl_2$/MeOH 98:2→97:3) to give the title compound as a 3:1 mixture of two diastereoisomers (538 mg).

NMR ($^1H$, $CDCl_3$)(anti isomer): δ 11.82 (bs, 1H), 7.42 (d, 1H), 7.10 (dd, 1H), 6.58 (d, 1H), 5.87 (m, 1H), 5.06 (m, 2H), 4.34 (d, 1H), 3.01 (m, 1H), 2.68 (m, 1H), 2.37 (s, 3H), 2.20 (m, 1H), 2.07 (m, 1H), 1.80 (m, 1H), 1.70 (m, 1H), 1.49 (m, 1H).

NMR ($^1H$, $CDCl_3$)(syn isomer): δ 11.70 (bs, 1H), 7.36 (d, 1H), 7.12 (dd, 1H), 6.81 (d, 1H), 5.83 (m, 1H), 5.02 (m, 2H), 4.23 (bt, 1H), 2.98 (m, 1H), 2.66 (m, 1H), 2.28 (s, 3H), 2.20 (m, 1H), 2.02-1.80 (m, 2H), 1.62-1.47 (m, 2H).

MS (m/z): 348 $[M]^+$, 307 $[M-allyl]^+$.

Intermediate 25

Anti-5-Allyl-4-chloro-8-(2,4-dichlorophepyl)-2-methyl-5,6,7,8-tetrahydroquinazoline (isomer 1) and Syn-5-Allyl-4-chloro-8-(2,4-dichlorophepyl)-2-methyl-5,6,7,8-tetrahydroquinazoline (isomer 2)

Intermediate 24 (538 mg) was dissolved in $POCl_3$ (5 mL) and the mixture was refluxed for 2 hr. The $POCl_3$ was evaporated, the residue was dissolved in $CH_2Cl_2$ and treated with conc. $NH_4OH$. The two phases were separated and the aqueous layer was extracted with $CH_2Cl_2$ (3×10 mL). The combined organic extracts were washed with brine (2×10 mL) and dried over $Na_2SO_4$. The solids were filtered and the solvent evaporated. The crude product was purified by flash chromatography (silica gel, cHex/EtOAc 95:5)to give the title compound isomer 1 (262 mg) and the title compound isomer 2 (94 mg) as colourless oils.

isomer 1:NMR ($^1H$, $CDCl_3$): δ 7.44 (d, 1H), 7.06 (dd, 1H), 6.20 (d, 1H), 5.86 (m, 1H), 5.14 (m, 2H), 4.63 (d, 1H), 3.16 (m, 1H), 2.60 (m, 1H), 2.59 (s, 3H), 2.30 (m, 1H), 2.16 (m, 1H), 1.89 (m, 1H), 1.80 (m, 1H), 1.64 (m, 1H).

MS (m/z): 367 $[M+H]^+$.

isomer 2:NMR ($^1H$, $CDCl_3$): δ 7.36 (d, 1H), 7.15 (dd, 1H), 6.83 (bd, 1H), 5.82 (m, 1H), 5.10-5.06 (m, 2H), 4.35 (m, 1H), 3.12 (m, 1H), 2.62 (m, 1H), 2.48 (s, 3H), 2.25 (m, 1H), 2.22-2.00 (m, 2H), 1.90-1.78 (m, 2H).

MS (m/z): 367 $[M+H]^+$.

Intermediate 26

[5-Allyl-7-(2,4-dichlorophenyl)-2-methyl-6,7-dihydro-5H-pyrrolo[2,3-d]pyrimidin-4-yl]-cyclopropylmethyl-amine A solution of intermediate 9 (160 mg, 0.451 mmol) in cyclopropylmethylamine (0.5 mL) was heated at 130° C. (screw cap vial) for 4 hr. The amine was then evaporated and the residue was purified by flash chromatography (silica gel, gradient: $CH_2Cl_2$/EtOAc 9:1 to 7:3) to give the title compound (162 mg, 0.416 mmol, 92%) as a colourless oil.

NMR ($^1H$, $CDCl_3$): δ 7.43 (d, 1H), 7.36 (d, 1H), 7.24 (dd, 1H), 5.86 (m, 1H), 5.20-5.13 (m, 2H), 4.39 (bt, 1H), 3.88 (dd, 1H), 3.71 (dd, 1H), 3.40-3.30 (m, 3H), 2.46 (m, 1H), 2.35 (m, 1H), 2.36 (s, 3H), 1.08 (m, 1H), 0.60-0.27 (m, 4H).

MS (m/z): 389 $[M+H]^+$ (2 Cl).

Intermediate 27

5-Cyclopropylmethyl-1-(2,4-dichlorophenyl)-7-methyl-1,2,2a,3,4,5-hexahydro-1,5,6,8-tetraaza-acenaphthylen-4-ol To a solution of intermediate 26 (160 mg, 0.411 mmol) in a 8:1 mixture of acetone and water (8 mL) was added N-methylmorpholine-N-oxide (100 mg, 2 eq), followed by a 4% aqueous solution of $OsO_4$ (0.260 mL, 0.1 eq) and the reaction mixture was stirred at r.t. for 3.5 hr. The solution was then concentrated under reduced pressure, and sat.aq. $Na_2SO_3$ (50 mL) was added. The aqueous phase was extracted with EtOAc (3×10 mL) and dried over anh. $Na_2SO_4$. The solids were filtered and the solvent evaporated. The crude diol was dissolved in a 1:1 mixture of THF and water (8 mL) and $NaIO_4$ (132 mg, 1.5 eq) was added. The reaction mixture was stirred at r.t. for 45 min. It was then diluted with water and extracted with EtOAc (3×10 mL). The combined organic extracts were washed once with brine and dried over anh. $Na_2SO_4$. The solids were filtered and the solvent evaporated. The crude product was purified by flash chromatography (silica gel, cHex/EtOAc 1:1). The title compound was obtained as a colourless oil (111 mg, 0.284 mmol, 69%).

NMR ($^1H$, DMSO-$d_6$): δ 7.68 (d, 1H), 7.44 (m, 2H), 5.92 (d, 1H), 5.17 (m, 1H), 4.13 (t, 1H), 3.79 (m, 1H), 3.76 (dd, 1H), 3.50 (m, 1H), 3.15 (dd, 1H), 2.24 (m, 1H), 2.21 (s, 3H), 1.43 (dt, 1H), 1.06 (m, 1H), 0.50-0.20 (m, 4H).

MS (m/z): 391 $[M+H]^+$ (2 Cl).

Intermediate 28

5-Cyclopropylmethyl-1-(2,4-dichlorophenyl)-4-methoxy-7-methyl-1,2,2a,3,4,5-hexahydro-1,5,6,8-tetraaza-acenaphthylene A solution of PTSA (1.5 mg, 0.042 eq) in anh. MeOH (1.5 mL) was added to the neat intermediate 27 (73 mg, 0.187 mmol) and the resulting solution was stirred at r.t. for 18 hr. The solvent was then evaporated and the residue was dissolved in $CH_2Cl_2$ (10 mL). A solution prepared by diluting sat.aq. $NaHCO_3$ with water (1:1, 10 mL) was then added and the aqueous phase was extracted with $CH_2Cl_2$ (2×10 mL). The combined organic extracts were washed with water (1×10 mL), sat.aq. NaCl (1×10 mL) and dried over anh. $Na_2SO_4$. The solids were filtered and the solvent evaporated. The title compound was obtained as a yellow oil and was used in the subsequent step without further purification (68 mg, 0.168 mmol, 90%).

NMR ($^1$H, acetone-$d_6$): δ 7.53 (d, 1H), 7.47 (d, 1), 7.35 (dd, 1H), 4.93 (t, 1H), 4.23 (t, 1H), 4.05 (dd, 1H), 3.78 (dd, 1H), 3.51 (m, 1H), 3.39 (s, 3H), 3.13 (dd, 1H), 2.53 (dddd, 1H), 2.25 (s, 3H), 1.40 (dt, 1H), 1.09 (m, 1H), 0.50-0.20 (m, 4H).

MS (m/z): 405 $[MH]^+$2 Cl).

Intermediate 29

Alternative preparation of intermediate 2: 2-[4-Chloro-7-(2,4-dichlorophenyl)-2-methyl-6,7-dihydro-5H-pyrrolo[2,3-d]pyrimidin-5-yl]-ethanol To a solution of intermediate 10 (93 mg, 0.261 mmol) in a 2:1 mixture of anh. $CH_2Cl_2$/MeOH (3 mL), at 0° C., under $N_2$, was added $NaBH_4$ (20 mg, 2 eq). The reaction mixture was stirred at r.t. for 1 hr. The reaction was then quenched with water (10 mL) and concentrated under reduced pressure. The aqueous phase was extracted with EtOAc (3×10 mL) and the combined organic extracts were dried over anh. $Na_2SO_4$. The solids were filtered and the solvent evaporated. The title compound was obtained as a white solid (80 mg, 0.223 mmol, 85%) and was used without further purification in the subsequent step.

NMR ($^1$H, $CDCl_3$): δ 7.54 (d, 1H), 7.40-7.30 (m, 2H), 4.20 (t, 1H), 3.93 (dd, 1H), 3.87 (m, 2H), 3.75 (m, 1H), 2.57 (s, 3H), 2.27 (m, 1H), 1.99 (m, 1H).

MS (m/z): 358 $[MH]^+$ (3Cl).

Intermediate 30

Methanesulfonic acid 2-[4-chloro-7-(2,4-dichlorophenyl)-2-methyl-6,7-dihydro-5H-pyrrolo[2,3-d]pyrimidin-5-yl]-ethyl ester To a solution of intermediate 29 (80 mg, 0.223 mmol) in anh. $CH_2Cl_2$ (2 mL), at r.t., under $N_2$, was added triethylamine (155 μL, 5 eq) followed by mesyl chloride (35 μL, 2 eq). The reaction mixture was stirred at r.t. for 1 hr. It was then quenched with water (10 mL) and extracted with $CH_2Cl_2$ (3×10 mL). The combined organic extracts were washed once with brine and dried over anh. $Na_2SO_4$. The solids were filtered and the solvent evaporated. The crude compound was purified by flash chromatography (silica gel, cHex/EtOAc 1:1). The title compound was obtained as a pale yellow oil (71 mg, 0.163 mmol, 73%).

NMR ($^1$H, $CDCl_3$): δ 7.48 (m, 1H), 7.32 (m, 2H), 4.38 (m, 2H), 4.09 (t, 1H), 3.82 (dd, 1H), 3.66 (m, 1H), 3.00 (s, 3H), 2.46 (m, 1H), 2.42 (s, 3H), 2.14 (m, 1H).

MS (m/z): 436 $[MH]^+$ (3Cl).

Intermediate 31

{5-[1-(tert-Butyl-diphenyl-silanyloxymethyl)-but-3-enyl]-6-chloro-2-methyl-pyrimidin-4-yl}-(2,4-bis-trifluoromethyl-phenyl)-amine To a solution of 2,4-bis(trifluoromethyl)aniline (2.11 g, 9.21 mmol) in anh. DMF (45 mL), at 0° C., under $N_2$, was added NaH 80%/oil (608 mg, 2.2 eq). After 30 min the reaction mixture was warmed to r.t. After 30 min a solution of intermediate 11 (4.46 g, 9.21 mmol) in anh. DMF (30 mL) was added. The reaction mixture was left at r.t. for 15 min, then cooled down at 0° C. and diluted with water. The aqueous phase was extracted with EtOAc (3×50 mL) and the combined organic extracts were washed with water (50 mL), brine (50 mL) and then dried over anh. $Na_2SO_4$. The solids were filtered and the solvent evaporated. The crude product was purified by flash chromatography (silica gel, cHex/EtOAc 97:3) to give the title compound (4.546 g, 6.71 mmol, 73%) as a clear oil.

NMR ($^1$H, DMSO): δ 8.34 (s, 1H), 7.97 (s, 1H), 7.53 (d, 1H), 7.48 (d, 1H), 7.54-7.31 (m, 10H), 5.7 (m, 1H), 4.97 (d, 1H), 4.90 (d, 1H), 4.11 (m, 1H), 3.99 (m, 1H), 3.72 (m, 1H), 2.56 (m, 2H), 2.18 (s, 3H), 0.91 (s, 9H).

MS (m/z): 678 $[MH]^+$.

Intermediate 32

5-(tert-Butyl-diphenyl-silanyloxymethyl)-4-chloro-2-methyl-8-(2,4-bis-trifluoromethyl-phenyl)-5,6,7,8-tetrahydro-pyrido[2,3-d]pyrimidin-7-ol To a solution of intermediate 31 (2 g, 2.95 mmol) in an 8:1 mixture of acetone/$H_2O$ (36 mL), at r.t., were added N-methyl-morpholine-N-oxide (716 mg, 2 eq) and $OsO_4$ 4%/$H_2O$ (1.8 mL, 0.1 eq). After 3.5 h the solvent was evaporated and a saturated solution of $Na_2SO_3$ was added. The product was extracted with EtOAc (2×20 mL) and the combined organic extracts were dried over anh. $Na_2SO_4$. The solids were filtered and the solvent was evaporated. The oil obtained was dissolved in a 9:1 mixture of THF/$H_2O$ (45 mL) and $NaIO_4$ (947 mg, 1.5 eq) was added. The reaction mixture was stirred at r.t. for 18 hr. It was then diluted with water and the product was extracted with EtOAc (3×20 mL). The combined organic extracts were washed with brine and dried over anh. $Na_2SO_4$. The solids were filtered and the solvent was evaporated to give the title compound (1.932 g, 2.85 mmol, 96%), as a mixture of two diastereoisomers.

NMR ($^1$H, Acetone):

Isomer 1: δ 8.15 (m, 2H), 7.72 (m, 5H), 7.44 (m, 6H), 6.19 (d, 1H), 5.27 (m, 1H), 4.41 (t, 1H), 4.08 (dd, 1H), 3.52 (m, 1H), 2.81 (m, 1H), 2.35 (m, 1H), 2.15 (s, 3H), 1.07 (s, 9H).

Isomer 2: δ 8.15 (m, 2H), 7.72 (m, 5H), 7.44 (m, 6H), 5.8-5.4 (m, 2H), 4-3.8 (m, 2H), 3.6-3.4 (m, 1H), 3-2.8 (m, 1H), 2.35 (m, 1H), 2.15 (s, 3H), 1.07 (s, 9H).

MS (m/z): 680 $[MH]^+$.

Intermediate 33

5-(tert-Butyl-diphenyl-silanyloxymethyl)-4-chloro-2-methyl-8-(2,4-bis-trifluoromethyl-phenyl-5,6,7,8-tetrahydro-pyrido[2,3-d]pyrimidine To a solution of intermediate 32 (1.93 g, 2.84 mmol) in anh. $CH_2Cl_2$ (50 mL), at −78° C., were added $Et_3SiH$ (1.82 mL, 4 eq) and $BF_3.Et_2O$ (1.58 mL, 4.4 eq). The reaction mixture was stirred 1 hr at −78° C. and then was allowed to warm to r.t. and stirred for 18 hr. A saturated solution of $NaHCO_3$ was then added and the product was extracted with $CH_2Cl_2$ (3×50 mL). The combined organic extracts were dried over anh. $Na_2SO_4$, the solids were filtered and the solvent evaporated. The crude product was purified by flash chromatography (silica gel, cHex/EtOAc 95:5) to give the title compound (0.607 g, 9.16 mmol, 32%) as a white solid.

NMR ($^1$H, $CDCl_3$): δ 7.98-7.94 (d, 1H), 7.88-7.80 (dd, 1H), 7.7-7.58 7.44-7.32 (m, 10H), 7.35-7.14 (d, 1H), 3.98-3.94 (dd, 1H), 3.73-3.55 (m, 1H), 3.63-3.59 (m, 1H), 3.44-3.36 3.38-3.3 (2m, 2H), 2.55-2.4 (m, 1H), 2.17-2.15 (s, 3H), 2.04-1.9 (m, 1H), 0.98 (s, 9H).

MS (m/z): 664$[MH]^+$.

Intermediate 34

{4-Chloro-2-methyl-8-(2,4-bis-trifluoromethyl-phenyl)-5,6,7,8-tetrahydro-pyrido[2,3-d]pyrimidin-5-yl}-methanol To a solution of intermediate 33 (600 mg, 0.91 mmol) in anh. DMF (15 mL), at r.t., under $N_2$, was added $Et_3N.3HF$ (1.25 mL, 8.4 eq) and the reaction mixture was heated at 40° C. for 6.5 h. It was then cooled down to r.t. and diluted with water. The product was extracted with $Et_2O$ (3×20 mL). The combined organic extracts were washed with brine and dried over anh. $Na_2SO_4$. The solids were filtered and the solvent evaporated. The crude product was purified by flash chromatography (silica gel, cHex/EtOAc 6:4) to give the title compound (337 mg, 0.8 mmol, 88%) as a clear oil.

NMR ($^1H$, DMSO): δ 8.26-8.12 (m, 2H), 7.9-7.8 (d, 1H), 5.08-4.98 (t, 1H), 3.9-3.6 (2H), 3.7-3.3 (2H), 3.24-3.10 (1H), 2.3 (m, 1H), 2.09 (s, 3H), 2.0-1.8 (m, 1H).

MS (m/z): 426[MH]$^+$.

Intermediate 35

Methanesulfonic acid 4-chloro-2-methyl-8-(2,4-bis-trifluoromethyl-phenyl)-5,6,7,8-tetrahydro-pyrido[2,3-d]pyrimidin-5-ylmethyl ester To a solution of intermediate 34 (200 mg, 0.47 mmol), in anh. $CH_2Cl_2$ (10 mL), under $N_2$, at 0° C., were added $Et_3N$ (0.26 mL, 4 eq) and MsCl (73 µl, 2 eq). The reaction mixture was warmed to r.t. and stirred for 18 hr. It was then diluted with water and the product was extracted with $CH_2Cl_2$ (3×20 mL). The combined organic extracts were washed with brine and dried over anh. $Na_2SO_4$. The solids were filtered, the solvent evaporated and the crude product was purified by flash chromatography (silica gel, cHex/EtOAc 6:4) to give the title compound (203 mg, 0.4 mmol, 86%) as a clear oil.

NMR ($^1H$,DMSO): δ 8.3 8.14 (m, 2H), 7.95-7.8 (d+d, 1H), 4.56-4.20 (2H), 3.9-3.4 (m, 3H), 3.25 (s, 3H), 2.11 (s, 3H), 2.2-1.9 (m, 2H).

MS (m/z): 504[MH]$^+$.

Intermediate 36

{4-Chloro-2-methyl-7-(2,4-bis-trifluoromethyl-phenyl)-6,7-dihydro-5H-pyrrolo[2,3-d]pyrimidin-5-yl}-acetaldehyde To a solution of intermediate 31 (0.6 g, 0.886 mmol) in anh. DMF (15 mL), at r.t., under $N_2$ was added $Et_3N.3HF$ (1.22 mL, 8.4 eq). The reaction mixture was stirred at r.t. for 18 hr. The reaction mixture was diluted with water and the product was extracted with $Et_2O$ (3×20 mL). The combined organic extracts were washed with brine and dried over anh. $Na_2SO_4$. The solids were filtered and the solvent evaporated. The crude product was purified by flash chromatography (silica gel, cHex/EtOAc 8:2) to give an alcohol intermediate (346 mg, 89%) which was dissolved into anh. $CH_2Cl_2$ (15 mL) and cooled down to 0° C. $Et_3N$ (0.44 mL, 4 eq) and MsCl (0.122 mL, 2 eq) were added, and the reaction mixture was warmed to r.t. and stirred for 18 hr. The reaction mixture was diluted with water and the product was extracted with $CH_2Cl_2$ (3×20 mL). The combined organic extracts were dried over anh. $Na_2SO_4$, the solids were filtered and the solvent evaporated. The crude product was purified by flash chromatography (silica gel, cHex/EtOAc 8:2) to give a cyclic pyrrolidine intermediate (276 mg, 83%). This intermediate was dissolved in an 8:1 mixture of acetone/$H_2O$ (18 mL) and N-methyl-morpholine-N-oxide (230 mg, 2 eq) and $OsO_4$ (403 µl, 0.1 eq) were added. The reaction mixture was stirred at r.t. for 6 h. The solvent was evaporated and a saturated solution of $Na_2SO_3$ was added. The product was extracted with EtOAc (3×20 mL) and the combined organic extracts were dried over anh. $Na_2SO_4$. The solids were filtered and the solvent evaporated. The crude product was dissolved into a 9:1 mixture of THF/$H_2O$ (15 mL) and $NaIO_4$ (210 mg, 1.5 eq) was added. The reaction mixture was stirred at r.t. for 18 hr, then it was diluted with water and the product was extracted with EtOAc (3×20 mL). The combined organic extracts were washed with brine and dried over anh. $Na_2SO_4$. The solids were filtered and the solvent evaporated to give the title compound (250 mg, 0.59 mmol, 90%) as a clear oil.

NMR ($^1H$, $CDCl_3$): δ 9.86 (s, 1H), 8.05 (s, 1H), 7.93 (d, 1H), 7.5 (d, 1H), 4.24 (m, 1H), 3.93 (m, 1H), 3.65 (dd, 1H), 3.25 (dd, 1H), 2.93 (dd, 1H), 2.4 (s, 3H).

MS (m/z): 424[MH]$^+$.

Intermediate 37

Methanesulfonic acid 2-{4-chloro-2-methyl-7-(2,4-bis-trifluoromethyl-phenyl)-6,7-dihydro-5H-pyrrolo[2,3-d]pyrimidin-5-yl}-ethyl ester To a solution of intermediate 36 (250 mg, 0.59 mmol) in a 9:1 mixture of $CH_2Cl_2$/MeOH (15 mL), at 0° C., under $N_2$, was added $NaBH_4$ (44 mg, 2 eq). The reaction mixture was stirred for 30 min at 0° C. Conc. HCl was added until pH=7 was reached. The reaction mixture was then diluted with water and the product was extracted with $CH_2Cl_2$ (3×20 mL). The combined organic extracts were washed with brine and dried over anh. $Na_2SO_4$. The solids were filtered and the solvent evaporated to give a white solid (alcohol intermediate, 231 mg, 0.54 mmol, 93%) which was dissolved in anh. $CH_2Cl_2$ (15 mL). The reaction mixture was cooled at 0° C., then $Et_3N$ (302 µl, 4 eq) and MsCl (85 µl, 2 eq) were added. The reaction mixture was stirred at r.t. for 18 hr, then it was diluted with water and the product was extracted with $CH_2Cl_2$ (3×20 mL). The combined organic extracts were dried over anh. $Na_2SO_4$, the solids were filtered and the solvent evaporated. The crude product was purified by flash chromatography (silica gel, cHex/EtOAc 6:4) to give the title compound (252 mg, 0.50 mmol, 93%) as a clear oil.

NMR ($^1H$, $CDCl_3$): δ 8.05 (bs, 1H), 7.94 (bd, 1H), 7.53 (bd, 1H), 4.42 (m, 2H), 4.07 (t, 1H), 3.83 (dd, 1H), 3.71 (m, 1H), 3.04 (s, 3H), 2.46 (m, 1H), 2.43 (s, 3H), 2.13 (m, 1H).

MS (m/z): 504[MH]$^+$.

Intermediates 38 and 39

(S)-2-Acetoxy-propionic acid 4-chloro-2-methyl-8-(2,4-bis-trifluoromethyl-phenyl)-5,6,7,8-tetrahydro-pyrido[2,3-d]pyrimidin-5(S)-ylmethyl ester and (S)-2-Acetoxy-propionic acid 4-chloro-2-methyl-8-(2,4-bis-trifluoromethyl-phenyl)-5,6,7,8-tetrahydro-pyrido[2,3-d]pyrimidin-5(R)-ylmethyl ester To a solution of intermediate 34 (320 mg, 0.753 mmol) in $CH_2Cl_2$ (7 mL) at 0° C., under $N_2$, were added DMAP (230 mg, 2.5 eq), $Et_3N$ (0.73 mL, 7 eq) and (S)-2-acetoxypropionyl chloride (0.61 mL, 6.4 eq). The reaction mixture was stirred at 0° C. for 30 min, warmed to r.t and diluted with a saturated solution of $NaHCO_3$. The product was extracted with $CH_2Cl_2$ (3×30 mL) and the combined organic extracts were dried over anh. $Na_2SO_4$. The solids were filtered and the solvent was evaporated. The crude product was purified by flash chromatography (silica gel, cHex/EtOAc 8:2). The two diastereoisomers were separated by preparative chiral hplc: intermediate 38 (97 mg, 0.18 mmol, d.e.=97%) and intermediate 39 (89.7 mg, 0.17 mmol, d.e.>99%) were obtained as white solids.

NMR ($^1$H, Acetone):

Intermediate 38: δ 8.22-8.13 (m, 2H), 7.96-7.8 (d+d, 1H), 5.06 (, 11H), 4.56-4.34 (m, 2H), 4.07-3.54 (m, 3H), 2.34-2.05 (m, 2H), 2.7 (s, 3H), 2.06 (s, 3H), 1.48 (d+d, 3H).

Intermediate 39: δ 8.22-8.14 (m, 2H), 7.96-7.81 (d+d, 1H), 5.06 (m, 1H), 4.5-4.3 (m, 2H), 4.1-3.54 (m, 3H), 2.7 (s, 3H), 2.3-2.0 (m, 2H), 2.13 (s, 3H), 1.47 (d, 3H).

MS (m/z): 540[MH]$^+$.

| HPLC: | |
|---|---|
| Preparative: | |
| Pre-column/Guard column: | Filter Rhodyne |
| Column type: | Daicel CHIRALPAK AD |
| Column length [cm]: | 25 |
| Internal diameter [mm]: | 2 |
| Injection volume [μl]: | 500 |
| Mobile phase: | n-hexane-IPA 90/10 v/v |
| Flow rate [mL/min]: | 6.5 |
| Detector type: | DAD |
| Wavelength [nm]: | 225, 292 |
| Intermediate 38: | 21.8, r.t. (min) |
| Intermediate 39: | 26.5, r.t. (min) |
| Analytical: | |
| Pre-column/Guard column: | Filter Rhodyne |
| Column type: | CHIRALPAK AD |
| Column length [cm]: | 25 |
| Internal diameter [mm]: | 4.6 |
| Particle size [μm]: | 5 |
| Column temperature [ˆC]: | r.t. |
| Autosampler temperature [ˆC] | r.t. |
| Injection volume [μl]: | 20 |
| Mobile phase: | n-hexane/isopropylalcohol 90/10 v/v |
| Flow rate [mL/min]: | 1.0 |
| Detector type: | DAD |
| Wavelength [nm]: | 225 |
| Intermediate 38: | 6.88, r.t. (min) |
| Pre-column/Guard column: | Filter Rhodyne |
| Column type: | CHIRALPAK AD |
| Column length [cm]: | 25 |
| Internal diameter [mm]: | 4.6 |
| Column temperature [° C.]: | r.t. |
| Autosampler temperature [° C.] | r.t. |
| Mobile phase: | n-hexane/2-Propanol 90/10 v/v |
| Flow rate [mL/min]: | 1.0 |
| Detector type: | DAD |
| Wavelength [nm]: | 220-350 |
| Intermediate 39: | 8.29, r.t. (min) |

Intermediate 40

{4-Chloro-2-methyl-8-(2,4-bis-trifluoromethyl-phenyl)-5,6,7,8-tetrahydro-pyrido[2,3-d]pyrimidin-5(S)-yl}-methanol To a solution of intermediate 38 (90 mg, 0.167 mmol) in a 4:1 mixture of THF/$H_2O$ (5 mL), at 0° C., was added LiOH (14 mg, 2 eq) and the reaction mixture was stirred for 50 min. It was then diluted with water and the product was extracted with $Et_2O$ (2×10 mL) and with EtOAc (1×10 mL). The combined organic extracts were dried over anh. $Na_2SO_4$. The solids were filtered, the solvent was evaporated and the crude product was purified by flash chromatography (silica gel, cHex/AcOEt 6:4) to give the title compound (65 mg, 0.15 mmol, 92%, e.e.=97%) as a clear oil.

NMR ($^1$H, DMSO): δ 8.3-8.1 (m, 2H), 7.88-7.81 (d+d, 1H), 5.00 (broad, 1H), 3.9-3.6 (m, 2H), 3.7-3.3 (m, 2H), 3.2-3.1 (m, 1H), 2.3 (m, 1H), 2.09 (s, 3H), 2.00-1.8 (m, 1H).

MS (m/z): 426[MH]$^+$.

| HPLC: | |
|---|---|
| Analytical | |
| Pre-column/Guard column: | Filter Rhodyne |
| Column type: | Daicel CHIRALPAK AD |
| Column length [cm]: | 25 |
| Internal diameter [mm]: | 0.46 |
| Column temperature [ˆC]: | r.t. |
| Autosampler temperature [ˆC] | r.t. |
| Injection volume [μl]: | 20 |
| Mobile phase: | n-hexane/IPA/EtOH |
| Step 1: | Time-Reserv.A-ReservB: 95/3.5/1.5 |
| Flow rate [mL/min]: | 1.0 |
| Detector type: | DAD |
| Wavelength [nm]: | 225 |
| Intermediate 40: | 10.28, r.t. (min) |

Intermediate 41

Methanesulfonic acid 4-chloro-2-methyl-8-(2,4-bis-trifluoromethyl-phenyl)-5,6,7,8-tetrahydro-pyrido[2,3-d]pyrimidin-5(S)-ylmethyl ester To a solution of intermediate 40 (62 mg, 0.145 mmol) in anh. $CH_2Cl_2$ (5 mL), at 0° C., under $N_2$, were added $Et_3N$ (80 μl, 4 eq) and MsCl (23 μl, 2 eq). The reaction mixture was brought to r.t., stirred for 1 h. and then diluted with water. The product was extracted with $CH_2Cl_2$ (3×20 mL) and the combined organic extracts were washed with brine and dried over anh. $Na_2SO_4$. The solids were filtered and the solvent evaporated. The crude product was purified by flash chromatography (silica gel, cHex/EtOAc 6:4) to give the title compound (67 mg, 0.13 mmol, 92%, e.e.=95%) as a clear oil.

NMR ($^1$H, DMSO): δ 8.3-8.14 (m, 2H), 7.94-7.83 (d, 1H), 4.55-4.20 (2H), 3.94-3.4 (m, 3H), 3.25 (s, 3H), 2.11 (s, 3H), 2.25-1.94 (m, 2H).

MS (m/z): 504[MH]$^+$.

| HPLC: | |
|---|---|
| Analytical | |
| Pre-column/Guard column: | Filter Rhodyne |
| Column type: | CHIRALPAK AD |
| Column length [cm]: | 25 |
| Internal diameter [mm]: | 4.6 |
| Particle size [μm]: | 5 |
| Column temperature [ˆC]: | r.t. |
| Autosampler temperature [ˆC] | r.t. |
| Injection volume [μl]: | 20 |
| Mobile phase: | n-hexane/EtOH/IPA 73.5/1.5/25 v/v |
| Flow rate [mL/min]: | 1.0 |
| Detector type: | DAD |
| Wavelength [nm]: | 225 |
| Intermediate 41: | 6.52, r.t. (min) |

Intermediate 42

{4-Chloro-2-methyl-8-(2,4-bis-trifluoromethyl-phenyl)-5,6,7,8-tetrahydro-pyrido[2,3-d]pyrimidin-5(R)-yl}-methanol To a solution of intermediate 39 (83 mg, 0.154 mmol) in a 4:1 mixture of THF/$H_2O$ (5 mL), at 0° C., was added LiOH (14 mg, 2 eq) and the reaction mixture was stirred for 20 min. It was then diluted with water and the product was extracted with $Et_2O$ (2×10 mL) and with EtOAc (1×10 mL), and the combined organic extracts were dried over anh. $Na_2SO_4$. The solids were filtered, the solvent was evaporated and the crude product was purified by flash chromatography (silica gel, cHex/EtOAc 7:3) to give the title compound (61 mg, 0.14 mmol, 93%, e.e.>99%) as a clear oil.

NMR ($^1H$, DMSO): δ 8.26-8.12 (m, 2H), 7.9-7.8 (d, 1H), 5.08-4.98 (t, 1H), 3.9-3.6 (m, 2H), 3.7-3.3 (m, 2H), 3.24-3.1 (m, 1H), 2.3 (m, 1H), 2.09 (s, 3H), 2.00-1.8 (m, 1H).

MS (m/z): 426[MH]$^+$.

HPLC:

| Analytical | |
|---|---|
| Pre-column/Guard column: | Filter Rhodyne |
| Column type: | CHIRALPAK AD |
| Column length [cm]: | 15 |
| Internal diameter [mm]: | 4.6 |
| Injection volume [μl] | 10 |
| Mobile phase: | n-hexane/Ethanol/IPA |
| Step 1: | Time-Reserv.A-Reserv.B: 95/1.5/3.5 v/v |
| Flow rate [mL/min]: | 1.0 |
| Detector type: | DAD |
| Wavelength [nm]: | 225 |
| Intermediate 42: | 9.417, r.t. (min) |

Intermediate 43

Methanesulfonic acid 4-chloro-2-methyl-8-(2,4-bis-trifluoromethyl-phenyl)-5,6,7,8-tetrahydro-pyrido[2,3-d]pyrimidin-5(R)-ylmethyl ester To a solution of intermediate 42 (58 mg, 0.136 mmol) in anh $CH_2Cl_2$ (5 mL), at 0° C., under $N_2$, were added $Et_3N$ (76 μl, 4 eq) and MsCl (21 μl, 2 eq). The reaction mixture was brought to r.t., stirred for 1 h. and then diluted with water. The product was extracted with $CH_2Cl_2$ (3×20 mL) and the combined organic extracts were washed with brine and dried over anh. $Na_2SO_4$. The solids were filtered, the solvent evaporated and the crude product was purified by flash chromatography (silica gel, cHex/EtOAc 7:3) to give the title compound (57.6 mg, 0.11 mmol, 85%, e.e.>99%) as a clear oil.

NMR ($^1H$, DMSO): δ 8.3-8.14 (m, 2H), 7.95-7.8 (d, 1H), 4.56-4.20 (2H), 3.9-3.4 (m, 3H), 3.25 (s, 3H), 2.11 (s, 3H), 2.2-1.9 (m, 2H).

MS (m/z): 504[MH]$^+$.

HPLC:

| Analytical | |
|---|---|
| Pre-column/Guard column: | Filter Rhodyne |
| Column type: | CHIRALPAK AD |
| Column length [cm]: | 25 |
| Internal diameter [mm]: | 4.6 |
| Particle size [μm]: | 3 |
| Injection volume [μl]: | 10 |
| Mobile phase: | n-hexane/Ethanol/IPA |
| Step 1: | Time-Reserv.A-Reserv.B: 75/1.5/23.5 v/v |
| Flow rate [mL/min]: | 1.0 |
| Detector type | DAD |
| Wavelength [nm]: | 225 |
| Intermediate 43: | 4.703, r.t. (min) |

Intermediate 44

3-(2,4-Dichloro-phenyl)-2-hydroxy-6-nitromethyl-cyclohex-1-enecarboxylic acid methyl ester To a solution of intermediate 23 (26 mg, 0.087 mmol) in an anh. mixture of $Et_2O$/THF (0.5 mL/0.1 mL) was added nitromethane (0.005 mL, 1.1 eq) and Amberlyst A21 (weekly basic resin: 260 mg). The solvent was slowly evaporated at r.t. without agitation. After 2.5 hr, the dry resin was diluted with $Et_2O$ and decanted. It was rinsed further with $Et_2O$ (7×) and the combined organic fractions were evaporated. The crude product was purified by flash chromatography (silica gel, cHex/EtOAc, 9:1) to give the title compound (25 mg, 80%) as a clear oil.

NMR ($^1H$, $CDCl_3$): δ 12.72 (s, 1H), 7.41 (d, 1H), 7.24 (dd, 1H), 7.03 (d, 1H), 4.64 (dd, 1H), 4.50 (t, 1H), 4.07 (bm, 1H), 3.87 (s, 3H), 3.58 (m, 1H), 2.08 (bm, 1H), 1.85 (bm, 3H).

MS (m/z): 359 [MH]$^+$ (2 Cl).

Intermediate 45

8-(2,4-Dichloro-phenyl)-2-methyl-5-nitromethyl-5,6,7,8-tetrahydro-quinazolin-4-ol Sodium (21 mg, 3.1 eq) was added portionwise to anh. MeOH (1.5 mL) under $N_2$. After consumption of metallic sodium, acetamidine hydrochloride (96 mg, 3.3 eq) was added. After 10 min of stirring, the precipitated NaCl was filtered off and washed with anh. MeOH (2 mL). The solution of free acetamidine was added to intermediate 44 (106 mg, 0.294 mmol) and the mixture was stirred at r.t. for 18 hr. The solvent was evaporated and the crude product was purified by flash chromatography (silica gel, EtOAc/cHex 8:2) to give the title compound as a clear oil (81 mg, 75%).

MS (m/z): 368 [MH]$^+$ (2 Cl).

Intermediate 46

4-Chloro-8-(2,4-dichloro-phenyl)-2-methyl-5-nitromethyl-5,6,7,8-tetrahydro-quinazoline A solution of intermediate 45 (73 mg, 0.198 mg) in $POCl_3$ (2 mL) was heated at reflux for 2.5 hr. $POCl_3$ was evaporated and the residue was taken up in $CH_2Cl_2$. The organic phase was washed with conc. $NH_4OH$, the phases were separated and the aqueous layer was extracted with $CH_2Cl_2$ (3×10 mL). The combined organic extracts were washed with sat.aq. NaCl and dried over anh. $Na_2SO_4$. The solids were filtered and the solvent was evaporated. The crude title compound (68 mg, 89%) was used as such in the next step.

MS (m/z): 386 [MH]$^+$ (3 Cl).

Intermediate 47

4-Chloro-8-(2,4-dichloro-phenyl)-2-methyl-5,6,7,8-tetrahydro-quinazoline-5-carbaldehyde To a stirred solution of intermediate 46 (64 mg, 0.166 mmol) in anh. MeOH (1 mL), at −10° C., under $N_2$, was added methanolic KOH (0.1M, 2.3 mL) dropwise. After stirring at −10° C. for 15 min, a solution of $KMnO_4$ (18 mg, 0.7 eq) and $MgSO_4$ (20 mg, 1 eq) in $H_2O$ (2.5 mL) was added dropwise (reaction temperature kept below 0° C.). The reaction mixture was stirred at 0° C. for 24 hr. It was then filtered on Celite, and the Celite cake washed with $CH_2Cl_2$. The solvent was evaporated and the aqueous phase extracted with $CH_2Cl_2$ (3×10 mL). The combined organic extracts were dried over anh. $Na_2SO_4$, the solids were filtered and the solvent evaporated. The crude oil obtained was purified by flash chromatography (silica gel, cHex/EtOAC 9:1→8:2). The title compound was obtained as a 65:35 mixture of diastereomers (27 mg, 46%, clear oil).

MS (m/z): 355 $[MH]^+$ (3 Cl).

Example 1

Synthesis of Representative Compounds of Structure (I-1)

5-(2,4-Dichlorophenyl)-1-(1-ethylpropyl)-7-methyl-1,2,2a,3,4,5-hexahydro-1,5,6,8-tetraaza-acenaphthylene (I-1-1)

A solution of intermediate 19 (14 mg) in pure 3-pentylamine (60 μl) was stirred at 120° C. for 8 hr. The reaction mixture was then diluted with water and extracted with $Et_2O$ (3×10 mL). The combined organic extracts were washed once with water, once with brine and dried over anh. $Na_2SO_4$. The solids were filtered, the solvent evaporated and the crude pale yellow oil was purified by flash chromatography (silica gel, cHex/EtOAc 8:2) to give the title compound as a pale yellow oil (5.9 mg).

5-(2,4-Dichlorophenyl)-1-(2-ethyl-butyl)-7-methyl-1,2,2a,3,4,5,5a,8b-octahydro-1,5,6,8-tetraaza-acenaphthylene (I-1-2)

A solution of intermediate 19 (10.0 mg) in pure 2-ethyl-n-butylamine (100 μl) was stirred in a sealed vial at 120° C. for 7 hr. The reaction mixture was then cooled down to r.t. and directly purified by flash chromatography (silica gel, Toluene/EtOAc 95:5) to give the title compound as pale yellow oil (1.9 mg).

5-(2,4-Dichlorophenyl)-1-(2-methoxy-1-methoxymethyl-ethyl)-7-methyl-1,2,2a,3,4,5,5a,8b-octahydro-1,5,6,8-tetraazaacenaphthylene (I-1-3)

A solution of intermediate 19 (16.5 mg) in pure 2-methoxy-1-(methoxymethyl)ethylamine (52.6 mg) was stirred at 150° C. (screw cap vial) for 4 hr. The reaction mixture was then cooled down to r.t. and directly purified by flash chromatography (silica gel, Toluene/EtOAc 6:4) to obtain the title compound as a pale yellow oil (4.2 mg).

7-Methyl-1-(1-propylbutyl)-5-(2,4-bis-trifluoromethyl-phenyl)-1,2,2a,3,4,5-hexahydro-1,5,6,8-tetraaza-acenaphthylen (I-1-4).

Intermediate 35 (135 mg, 0.27 mmol) and 4-aminoheptane (0.5 mL, 12 eq) were heated at 130° C. (screw cap vial) for 3 hr. The reaction mixture was then cooled down to r.t. and diluted with $CH_2Cl_2$. The solvent was evaporated and the crude product was purified by flash chromatography (sililca gel, cHex/EtOAc 9:1) to give the title compound (29.4 mg, 0.06 mmol, 23%) as a yellow solid.

Enantiomeric Resolution

First Enantiomer

7-Methyl-1-(1-propylbutyl)-5-(2,4-bis-trifluoromethyl-phenyl)-1,2,2a(S),3,4,5-hexahydro-1,5,6,8-tetraaza-acenaphthylene Intermediate 41 (60 mg, 0.119 mmol) and 4-aminoheptane (178 μl, 10 eq) were heated at 130° C. (screw cap vial) for 3 h. The reaction mixture was diluted with $CH_2Cl_2$ and the solvent was evaporated. The crude product was purified by flash chromatography (silica gel, cHex/EtOAc 95:5) to give the title compound (19.4 mg, 0.04 mmol, 33%, e.e.=95%) as a clear oil.

| HPLC: | |
|---|---|
| Analytical | |
| Column type: | CHIRALPAK OD |
| Column length [cm]: | 25 |
| Internal diameter [mm]: | 4.6 |
| Column temperature [°C]: | 35 |
| Injection volume [μl]: | 10 |
| Mobile phase: | $CO_2$/EtOH (0.15% Ipa) 85/15 |
| Flow rate [mL/min]: | 2.5 |
| Detector type: | UV |
| Wavelength [nm]: | 225 |
| Column pressure [bar]: | 150 |
| Title compound: | 2.55, r.t. (min) |

$^1$H-NMR and MS data are the same as reported in the following Table 1 for compound I-1-4

Second Enantiomer

7-Methyl-1-(1-propylbutyl)-5-(2,4-bis-trifluoromethyl-phenyl)-1,2,2a(R),3,4,5-hexahydro-1,5,6,8-tetraaza-acenaphthylene Intermediate 43 (55 mg, 0.109 mmol) and 4-aminoheptane (163 μl, 10 eq) were heated at 130° C. (screw cap vial)

for 3 h. The reaction mixture was diluted with $CH_2Cl_2$ and the solvent was evaporated. The crude product was purified by flash chromatography (silica gel, cHex/EtOAc 95:5) to give the title compound (25.7 mg, 0.053 mmol, 49%, e.e.>99%) as a clear oil.

| HPLC: Analitical | |
|---|---|
| Column type: | CHIRALPAK OD |
| Column length [cm]: | 25 |
| Internal diameter [mm]: | 4.6 |
| Column temperature [° C]: | 35 |
| Injection volume [µl]: | 10 |
| Mobile phase: | $CO_2$/EtOH (0.15% Ipa) 85/15 |
| Flow rate [mL/min]: | 2.5 |
| Detector type: | UV |
| Wavelength [nm]: | 225 |
| Column pressure [bar]: | 150 |
| Title compound: | 2.12, r.t. (min) |

$^1$H-NMR and MS data are the same as reported in the following Table 1 for compound I-1-4

5-(2,4-Dichlorophenyl)-7-methyl-1-(1-propylbutyl)-1,2,2a,3,4,5-hexahydro-1,5,6,8-tetraaza-acenaphthylene (I-1-5)

A solution intermediate 19 (20 mg, 0.046 mmol) in 4-aminoheptane (100 µL) was heated at 130° C. (screw cap vial) for 18 hr. The amine was evaporated and the residue was directly purified by flash chromatography (silica gel, toluene/EtOAc, 9:1→8:2) to give the title compound as a clear oil (7 mg, 0.017 mmol, 36%).

Enantiomeric Resolution

First Enantiomer 5-(2,4-Dichlorophenyl)-7-methyl-1-(1-propylbutyl)-1,2,2a-(S),3,4,5,5a,8b-octahydro-1,5,6,8-tetraaza-acenaphthyl Intermediate 47 (120 mg, 0.276 mmol) and 4-aminoheptane (0.412 mL, 10 eq) was stirred at 130° C. (screw cap vial) for 18 hr. Then it was diluted with $CH_2Cl_2$ (5 mL) and the solvent was evaporated. The resulting crude product was purified by flash chromatography (silica gel, cHex/EtOAc 9.5:0.5) to afford the title compound (62 mg, 53%, ee %>99%) as a clear oil.

| HPLC: Analytical: | |
|---|---|
| Pre-column/Guard column: | Rheodyne filter |
| Column type: | CHIRALPAK AD |
| Column lenght (cm): | 25 |
| Internal diameter (mm): | 4.6 |
| Particle size (µm): | 5 |
| Column temperature (° C.): | r.t. |
| Autosampler temperature: (° C.): | r.t. |

-continued

| HPLC: Analytical: | |
|---|---|
| Injection volume (µL): | 20 |
| Mobile phase: | n-Hexane/tert-butanol 90/10 a/a |
| Flow rate (mL/min): | 1 |
| Detector type: | DAD |
| Wavelenght (nm): | 220-350 |
| Title compound: | 10.2 rt (min) |

$^1$H-NMR and MS data are the same as reported in the following Table 1 for compound I-1-5.

Second Enantiomer 5-(2,4-Dichlorophenyl)-7-methyl-1-(1-propylbutyl)-1,2,2a-(R),3,4,5,5a,8b-octahydro-1,5,6,8-tetraaza-acenaphthyl Intermediate 49 (130 mg, 0.298 mmol) and 4-aminoheptane (0.342 mL, 10 eq) were stirred at 130° C. (screw cap vial) for 18 hr. Then it was diluted with $CH_2Cl_2$ (5 mL) and the solvent was evaporated. The resulting crude product was purified by flash chromatography (silica gel, cHex/EtOAc 9.5:0.5) to afford the title compound (74 mg, 59%, ee %=90%) as a clear oil.

| HPLC: Analytical: | |
|---|---|
| Pre-column/Guard column: | Rheodyne filter |
| Column type: | CHIRALPAK AD |
| Column lenght (cm): | 25 |
| Internal diameter (mm): | 4.6 |
| Particle size (µm): | 5 |
| Column temperature (° C.): | r.t. |
| Autosampler temperature: (° C.): | r.t. |
| Injection volume (µL): | 20 |
| Mobile phase: | n-Hexane/tert-butanol 90/10 a/a |
| Flow rate (mL/min): | 1 |
| Detector type: | DAD |
| Wavelenght (nm): | 220-350 |
| Title compound: | 7.5, rt (min), 90%. |

$^1$H-NMR and MS data are the same as reported in the following Table 1 for compound I-1-5.

All the analytical data are set forth in the following Table 1.

TABLE 1

(I-1)

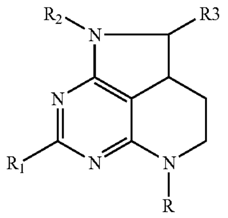

| Cpd. No. | R | $R_1$ | $R_2$— | $R_3$— | Analytical Data |
|---|---|---|---|---|---|
| 1-1-1 | 2,4-dichloro-phenyl | $CH_3$ | 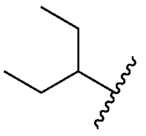 | H | NMR ($^1H$, $CDCl_3$, 55° C.): δ 7.46(d, 1H), 7.35-7.25(m, 2H), 3.86 (m, 1H), 3.69(m, 1H), 3.63(bm, 2H), 3.42(m, 1H), 3.23(m, 1H), 2.27(s, 3H), 2.24(m, 1H), 1.77(m, 1H), 1.70-1.40(m, 4H), 1.00(t, 3H), 0.82(t, 3H). MS (m/z): 391 $[MH]^+$, 2 Cl. |
| 1-1-2 | 2,4-dichloro-phenyl | $CH_3$ | 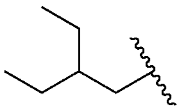 | H | NMR ($^1H$, $CDCl_3$): δ 7.46(s, 1H), 7.26(m, 2H), 3.86(m, 1H), 3.60(m, 2H+1H), 3.40(m, 1H), 3.06 (m, 1H), 2.70(dd, 1H), 2.35-2.20(m, 2H), 2.29(s, 3H), 1.60(m, 1H), 1.40-1.20 (m, 4H), 0.94(t, 6H). MS (m/z): 405 $[MH]^+$. |
| 1-1-3 | 2,4-dichloro-phenyl | $CH_3$ | 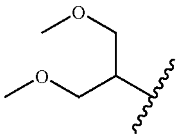 | H | NMR ($^1H$, $CDCl_3$, 55° C.): δ 7.43(bs, 1H), 7.23(bs, 2H), 4.30(bm, 1H), 3.80(bm, 1H), 3.59(m, 5H), 3.40 (bm, 3H), 3.35(s, 3H), 3.29(s, 3H), 2.26 (bs, 3H), 2.24(bm, 1H), 1.75(bm, 1H). MS (m/z): 423 $[MH]^+$. |
| 1-1-4 | 2,4-trifluoro-methylphenyl | $CH_3$ | 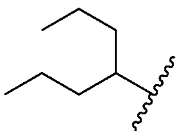 | H | NMR ($^1H$, $CDCl_3$): δ 7.99(s, 1H), 7.83 (d, 1H), 7.48(d, 1H), 4.06-3.24(bm, 5H), 2.23-2.2(bm, 4H), 1.74-1.1(bm, 10H), 0.97(t, 3H), 0.91(t, 3H). MS (m/z): 487$[MH]^+$. |
| 1-1-5 | 2,4-dichloro-phenyl | $CH_3$ | 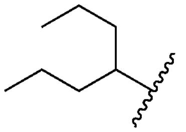 | H | NMR ($^1H$, $CDCl_3$): δ 7.46(d, 1H), 7.29 (d, 1H), 7.26(dd, 1H), 4.04(m, 1H), 3.67 (t, 1H), 3.64(bm, 2H), 3.41(m, 1H), 3.20 (t, 1H), 2.27(m, 4H), 1.55-1.10(m, 8H), 0.95(t, 3H), 0.88(t, 3H). MS (m/z): 419 $[MH]^+$ 2Cl. |

Example 2

Synthesis of Representative Compounds of Structure (1-2)

9-(2,4-Dichlorophenyl)-4-(1-ethylpropyl)-2-methyl-5,6,6a,7,8,9-hexahydro-4H-1,3,4-triazaphenalene (isomer 1) and 9-(2,4-Dichlorophenyl)-4-(1-ethyl-propyl)-2-methyl-5,6,6a,7,8,9-hexahydro-4H-1,3,4-triazaphenale (isomer 2) (2-1-1)

Intermediate 25 (isomer 1) was dissolved in anh. $CH_2Cl_2$ (6 mL) and treated with $O_3$ (5 g/hr) at −78° C. for 20 min. Dimethylsulfide (1 mL) was added and the mixture was allowed to warm to r.t. and stirred overnight. Then the reaction mixture was dried over $Na_2SO_4$, the solids were filtered and the solvent evaporated. The crude aldehyde (106 mg) was obtained as a 1:1 mixture of two diastereoisomers and used without further purification. To a solution of the aldehyde prepared above (30 mg) in anh. MeOH (1 mL), 1-ethyl-propylamine (0.010 mL) was added and the reaction mixture was stirred at r.t. for 3 hr. A 1M solution of $NaBH_3CN$ in 1M (0.162 mL) was then added and the mixture was stirred at r.t. for 65 hr. Another aliquot of 1M $NaBH_3CN$ in THF (0.080 mL) was added and the reaction was stirred at r.t. for 3 hr. The solvent was evaporated and the residue was partitioned between water and EtOAc. The aqueous layer was extracted with EtOAc (4×10 mL) and the combined organic extracts were washed with brine (2×10 mL), dried over anh. $Na_2SO_4$. The solids were filtered and the solvent evaporated. The crude product was purified by flash chromatography (silica gel, $CH_2Cl_2$/EtOAc 7:3) to give the title compound (16 mg) as a mixture of two diastereoisomers.

The two diastereoisomers were separated by preparative TLC (1% $NH_4OH$ in toluene/EtOAc 95:5) to give isomer 1 (5.4 mg) and isomer 2 (5.6 mg) as yellow oils.

All the analytical data are set forth in the following Table 2.

TABLE 2

(I-2)

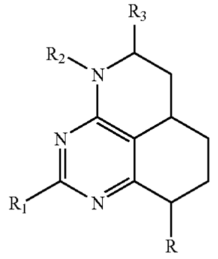

| Cpd. No. | R | $R_1$ | $R_2$— | $R_3$— | Analytical Data |
|---|---|---|---|---|---|
| 2-1-1 | 2,4-dichlorophenyl | $CH_3$ | 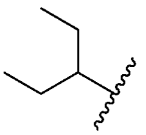 | H | Isomer 1: NMR ($^1H$, $CDCl_3$): δ 7.31(d, 1H), 7.14(dd, 1H), 7.01(bs, 1H), 5.01(bs, 1H), 4.41(bs, 1H), 3.34 (bd, 1H), 3.17(dt, 1H), 2.68(m, 1H), 2.40-2.30(m, 1H), 2.37(bs, 3H), 2.04(m, 2H), 1.67(bd, 1H), 1.55(m, 4H), 1.50-1.35(m, 2H), 0.87(t, 3H), 0.79(t, 3H). MS (m/z): 404 [M+H]. |
| | 2,4-dichlorophenyl | $CH_3$ | 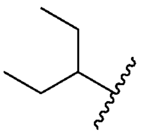 | H | Isomer 2: NMR ($^1H$, $CDCl_3$): δ 7.40(bs, 1H), 7.05(dd, 1H), 6.36(d, 1H), 5.03(bs, 1H), 5.00-4.50(broad, 1H), 3.40(bd, 1H), 3.22(dt, 1H), 2.60(m, 1H), 2.45(bs, 3H), 2.16-2.06(m, 2H), 2.03(m, 1H), 1.75(bd, 1H), 1.70-1.50(m, 4H), 1.45(dq, 1H), 1.24(m, 1H), 0.86(t, 6H). MS (m/z): 404 $[M+H]^+$. |

Example 3

Synthesis of Representative Compounds of Structure (1-3)

5-Cyclopropylmethyl-1-(2,4-dichlorophenyl)-7-methyl-1,2,2a,3,4,5-hexahydro-1,5,6,8-tetraaza-acenaphthylene (3-1-1)

To a solution of intermediate 10 (20 mg) in anh. $CH_3OH$ (1 mL) was added (aminomethyl)cyclopropane (5 μl, 1 eq). The reaction was stirred at r.t. for 90 min and then $NaBH_3CN$ 1.0M/THF (113 μl) was added. The mixture was stirred for an additional 18 hr at r.t. and quenched with $H_2O$ (10 mL). The product was extracted with EtOAc (2×15 mL), the combined extracts were dried over anh. $Na_2SO_4$, filtered and concentrated to dryness in vacuo. Flash chromatography of the crude product (silica gel, cHex/EtOAc 9:1) gave the title compound (5 mg) as a colourless oil.

1-(2,4-Dichlorophenyl)-5-(2-methoxyethyl)-7-methyl-1,2,2a,3,4,5-hexahydro-1,5,6,8-tetraaza-acenaphthylene (3-1-2)

To a solution of intermediate 10 (16 mg) in anh. THF (1 mL) was added 2-methoxy-ethylamine (4 μl). The reaction was stirred at r.t. for 90 min and then $NaBH_3CN$ 1.0M/THF (90 μl) was added. The mixture was stirred for an additional 18 hr at r.t. and quenched with $H_2O$ (10 mL). The product was extracted with EtOAc (2×15 mL). The combined extracts were dried over anh. $Na_2SO_4$, filtered and concentrated to dryness in vacuo. The crude product was dissolved in anh. THF (2 mL) and TEA (30 μl) was added. The reaction mixture was heated to reflux for 10 hr and quenched with $H_2O$. The product was extracted with EtOAc (2×10 mL). The combined extracts were dried over anh. $Na_2SO_4$, filtered and concentrated to dryness in vacuo. 2 mg (12%) of the title compound were obtained as a light beige oil after prep-TLC purification (eluted 3 times: 1: cHex 100%, 2: cHex/EtOAc 75:25, 3: cHex/EtOAc 50:50).

1-(2,4-Dichlorophenyl)-5-(1-ethylpropol)-7-methyl-1,2,2a,3,4,5-hexahydro-1,5,6,8-tetraaza-acenaphthylene (3-1-3)

To a solution of intermediate 10 (20 mg) in anh. THF (1 mL) was added 1-ethyl-propylamine (6.5 μl). The reaction mixture was stirred at r.t. for 90 min and then $NaBH_3CN$ 1.0M/THF (112 μl) was added. The mixture was stirred for an additional 18 hr at r.t. and quenched with water (10 mL). The product was extracted with EtOAc (2×10 mL). The combined extracts were dried over anh. $Na_2SO_4$, filtered and concentrated to dryness in vacuo. The crude product was dissolved in anh. toluene (2 mL) and heated to reflux for 18 hr. The reaction mixture was diluted with $H_2O$ (10 mL) and extracted with EtOAc (3×10 mL). The combined organic extracts were dried over anh. $Na_2SO_4$, filtered and concentrated to dryness in vacuo to give the title compound (1.6 mg, 7%).) as a colourless oil after prep-TLC purification (cHex/EtOAc 75:25).

1-(2,4-Dichlorophenyl)-5-(2-ethylbutyl)-7-methyl-1,2,2a,3,4,5-hexahydro-1,5,6,8-tetraaza-acenaphthylene (3-1-4)

To a solution of intermediate 10 (35.5 mg) in anh. MeOH (2 mL) was added 2-ethylbutylamine (0.014 mL) at r.t., under $N_2$. The reaction mixture was stirred at r.t. for 90 min. $NaBH_3CN$ (1 N solution in THF, 0.2 mL) was then added at r.t. and the reaction mixture was heated to 70° C. for 3 hr. It was then allowed to cool to r.t. and $H_2O$ (5 mL) was added. The organic solvent was evaporated under reduced pressure and the aqueous suspension was extracted with EtOAc (3×5 mL). The combined organic layers were washed with sat. aq. NaCl (5 mL) and dried over anh. $Na_2SO_4$. The solids were filtered and the solvent evaporated. The crude product was purified by flash chromatography (silica gel, cHex 100%→cHex/EtOAc 95:5) to yield the title compound as a yellow solid (0.018 g).

1-(2,4-Dichlorophenyl)-7-methyl-5-(1-propylbutyl)-1,2,2a,3,4,5-hexahydro-1,5,6,8-tetraaza-acenaphthylene (3-1-5)

A solution intermediate 30 (20 mg, 0.046 mmol) in 4-aminoheptane (100 μL) was heated at 130° C. (screw cap vial) for 6.5 hr, and then at r.t. for 18 hr. The amine was evaporated and the residue was directly purified by flash chromatography (silica gel, cHex/EtOAc, 9:1) to give the title compound as a clear oil (9 mg, 0.021 mmol, 47%).

7-Methyl-5-(1-propylbutyl)-1-(2,4-bis-trifluoromethyl-phenyl)-1,2,2a,3,4,5-hexahydro-1,5,6,8-tetraazaacenaphthylene (3-1-6)

Intermediate 37 (230 mg, 0.457 mmol) and 4-aminoheptane (0.68 mL, 10 eq) were heated at 130° C. (screw cap vial) for 14 hr. The reaction mixture was diluted with $CH_2Cl_2$ and the solvent were evaporated. The crude product was purified by flash chromatography (silica gel, cHex/EtOAc 95:5) to give the title compound (54 mg, 0.11 mmol, 24%) as a white solid.

5-Cyclopropylmethyl-1-(2,4-dichlorophenyl)-7-methyl-4-propyl-1,2,2a,3,4,5-hexahydro-1,5,6,8-tetraazaacenaphthylene (3-1-7)

To a suspension of $CuBr.Me_2S$ (48 mg, 5 eq) in anh. $Et_2O$ (0.8 mL) at −50° C., under $N_2$, was added PrMgBr 1M/THF (0.188 mL, 4 eq) dropwise under vigorous stirring. The dark yellow mixture was stirred for 45 min at −50° C. and was then cooled to −78° C. $BF_3.Et_2O$ (0.024 mL, 4 eq) was added and the reaction mixture was stirred for 20 min at −78° C. A solution of intermediate 28 (19 mg, 0.047 mmol) in anh. THF (0.5 mL) was added and the reaction temperature was allowed to rise to r.t. over 3 hr. After a total reaction time of 4 hr, a 1:1 mixture of conc. $NH_4OH$ and sat.aq. $NH_4Cl$ (2 mL) was added and the mixture was stirred for 15 min. Water and EtOAc were added, the phases were separated and the aqueous layer was extracted with EtOAc (3×10 mL). The combined organic extracts were washed with water and dried over anh. $Na_2SO_4$. The solids were filtered and the solvent evaporated. The crude product was purified by flash chromatography (silica gel, cHex/EtOAc 9:1). The title compound was obtained as a light yellow oil (3 mg, 0.007 mmol, 15%).

4-Butyl-5-cyclopropylmethyl-1-(2,4-dichlorophenyl)-7-methyl-1,2,2a,3,4,5-hexahydro-1,5,6,8-tetraazaacenaphthylene (3-1-8)

To a suspension of $CuBr.Me_2S$ (72 mg, 4.3 eq) in anh. $Et_2O$ (1 mL) at −50° C., under $N_2$, was added dropwise n-BuLi 1.6M/hexanes (0.21 mL, 4.15 eq) under vigorous stirring. The dark brown mixture was stirred for 40 min at −50° C., was then cooled at −78° C. and $BF_3.Et_2O$ (0.043 mL, 4.15 eq) was added. After stirring for 15 minutes at −78° C., a solution of intermediate 28 (33 mg, 0.081 mmol) in anh. THF (0.5 mL) was added and the reaction temperature was allowed to rise to r.t. over 3 hr. After a total reaction time of 3.5 hr, a 1:1 mixture of conc. $NH_4OH$ and a sat.aq. $NH_4Cl$ (1 mL) was added and the mixture was stirred for 15 min. Water and EtOAc were then added, the phases were separated and the aqueous layer was extracted with EtOAc (3×10 mL). The combined organic extracts were washed with water and dried over anh. $Na_2SO_4$. The solids were filtered and the solvent evaporated. The crude product was purified by flash chromatography (silica gel, cHex/EtOAc 9:1). The title compound (isomer 1: syn) was obtained as a pale yellow oil (16 mg, 0.037 mmol, 46%). A small percentage of the anti isomer 2 was also isolated.

5-Cyclopropylmethyl-1-(2,4-dichlorophenyl)-7-methyl-4-propoxy-1,2,2a,3,4,5-hexahydro-1,5,6,8-tetraazaacenaphthylene (3-1-9)

To a suspension of $CuBr.SMe_2$ (27 mg, 2 eq) in anh. $Et_2O$ (0.2 mL), at −60° C., under $N_2$, was added a solution of propyl magnesium bromide (0.2 mL, 2 eq: prepared by the addition of Mg (27 mg, 1.1 mmol) and propyl bromide in anh. $Et_2O$ (1.5 mL), at r.t., under $N_2$, for 1 hr). The yellow heterogeneous reaction mixture was diluted with an additional 0.2 mL of anh. $Et_2O$ and stirred at −60° C. for 30 min. It was then cooled down to −78° C. and $BF_3.Et_2O$ (17 μL, 2 eq) was added. After 10 min at −78° C., a solution of intermediate 28 (27 mg, 0.067 mmol) in anh. THF (0.4 mL) was added and the reaction mixture was slowly warmed to r.t. (4 hr). It was then diluted with a 1:1 mixture of conc. $NH_4OH$/sat.aq. $NH_4Cl$ and stirred at r.t. for 10 min. The aqueous phase was then extracted with $CH_2Cl_2$ (4×20 mL) and the combined organic extracts were washed with $H_2O$ (2×20 mL) and dried over anh. $Na_2SO_4$. The solids were filtered and the solvent evaporated. The crude compound was purified by flash chromatography (silica gel, 9:1→7:3 cHex/EtOAc). The title compound was obtained as a clear oil (4 mg, 0.009 mmol, 14%)

4,5-Dibutyl-1-(2,4-dichlorophenyl)-7-methyl-1,2,2a,3,4,5-hexahydro-1,5,6,8-tetraazaacena -phthylene (3-1-10)

To a suspension of $CuBr.Me_2S$ (65 mg, 4.3 eq) in anh. $Et_2O$ (1 mL) cooled to −50° C., under $N_2$, a 1.6 M solution of BuLi (0.184 mL, 0.295 mmol, 4 eq) was added dropwise under vigorous stirring. The dark brown mixture was stirred for 40 min between −50° C. and −40° C., then it was cooled to −78° C. and $BF_3.Et_2O$ (0.037 mL, 4 eq) was added. After stirring for 15 min at −78° C., intermediate 28 was added (30 mg, 0.074 mmol) dissolved in anh. THF (0.5 mL) and the reaction temperature was allowed to rise to r.t. over 3 hr. After a total reaction time of 3.5 hr, a 1:1 mixture of $NH_4OH$ and a saturated solution of $NH_4Cl$ (1 mL) was added and the mixture was stirred for 15 min. Then water and EtOAc were added, the phases were separated and the aqueous layer was extracted with EtOAc (3×10 mL). The combined organic extracts were washed with water and dried over anh. $Na_2SO_4$. The solids were filtered and the solvent evaporated. The crude product (28 mg) was purified by flash chromatography (cHex/EtOAc 9:1). The title compound (12 mg, 0.028 mmol, 37%) was obtained as a colourless oil.

All the analytical data are set forth in the following Table 3.

TABLE 3

(I-3)

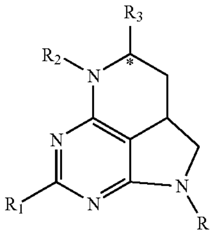

| Cpd. No. | R | $R_1$ | $R_2$— | $R_3$— | Analytical Data |
|---|---|---|---|---|---|
| 3-1-1 | 2,4-dichloro-phenyl | $CH_3$ | 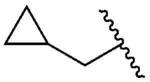 | H | NMR ($^1H$, $CDCl_3$): δ 7.41(d, 1H), 7.36(d, 1H), 7.22 (dd, 1H), 4.23(t, 1H), 3.7(dd, 1H), 3.55(t, 1H), 3.54-3.44(m, 3H), 3.25(dd, 1H), 2.37(s, 3H), 2.24 (m, 1H), 1.66(m, 1H), 1.00(m, 1H), 0.52(m, 2H), 0.29(m, 1H). MS (m/z): 375 $[MH]^+$, 2Cl. |
| 3-1-2 | 2,4-dichloro-phenyl | $CH_3$ | 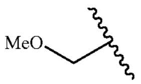 | H | NMR ($^1H$, $CDCl_3$): δ 7.41(d, 1H), 7.35(d, 1H), 7.22 (dd, 1H), 4.23(t, 1H), 3.94(m, 1H), 3.62-3.47(m, 5H), 3.37(s, 3H), 2.38(s, 3H), 2.21(m, 1H), 1.64(m, 1H). MS (m/z) 379 $[MH]^+$, 2Cl. |
| 3-1-3 | 2,4-dicloro-phenyl | $CH_3$ | 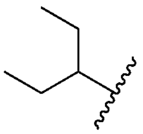 | H | NMR ($^1H$, $CDCl_3$): δ 7.41(d, 1H), 7.35(d, 1H), 7.22 (dd, 1H), 4.23(t, 1H), 3.94(m, 1H), 3.62-3.47(m, 5H), 3.37(s, 3H), 2.38(s, 3H), 2.21(m, 1H), 1.64(m, 1H). MS (m/z): 379 $[MH]^+$, 2Cl. |
| 3-1-4 | 2,4-dichloro-phenyl | $CH_3$ | 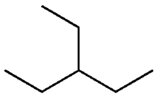 | H | NMR ($^1H$, $CDCl_3$): δ 7.56-7.30(m, 3H), 4.25(t, 1H), 3.68-3.40(m, 3H), 2.56(s, 3H), 2.45-2.27(m, 2H), 1.67(m, 6H), 0.95(m, 8H). MS (m/z): 405 $[MH]^+$. |
| 3-1-5 | 2,4-dichloro-phenyl | $CH_3$ | 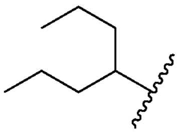 | H | NMR ($^1H$, $CDCl_3$): δ 7.35(m, 2H), 7.20(d, 1H), 4.80(m, 1H), 4.20(t, 1H), 3.55(m, 1H), 3.45(m, 1H), 3.35(m, 1H), 3.10(m, 1H), 2.30(s, 3H), 2.20(m, 1H), 1.60-1.15(m, 9H), 0.90(m, 6H). MS (m/z): 419 $[MH]^+$. |
| 3-1-6 | 2,4-trifluoro-methylphenyl | $CH_3$ | 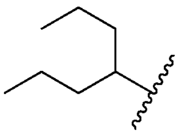 | H | NMR ($^1H$, $CDCl_3$): δ 7.93(s, 1H), 7.73(d, 1H), 7.59(d, 1H), 4.84(m, 1H), 4.14(t, 1H), 3.52(m, 1H), 3.47(m, 1H), 3.37(m, 1H), 3.12 (m, 1H), 2.34(s, 3H), 2.27(m, 1H), 1.6-1.2(m, 9H), 0.92(m, 6H). MS (m/z): 487 $[MH]^+$. |
| 3-1-7 | 2,4-dichloro-phenyl | $CH_3$ | 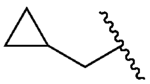 | 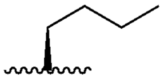 | NMR ($^1H$, $CDCl_3$): δ 7.40(d, 1H), 7.35(d, 1H), 7.20 (dd, 1H), 4.27-4.10(m, 2H), 3.68 (m, 1H), 3.55-3.42(m, 2H), 3.03 (dd, 1H), 2.35(s, 3H), 2.40-2.25 (m, 1H), 1.85-1.75(m, 1H), 1.75-1.50(m, 2H), 1.45-1.25(m, 2H), 0.95(t, 3H), 0.85(m, 1H), 0.55-0.25(m, 4H). MS (m/z): 417 $[MH]^+$ 2Cl. |

TABLE 3-continued (I-3)

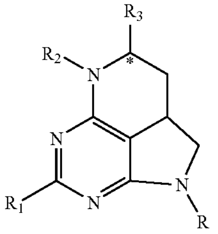

| Cpd. No. | R | $R_1$ | $R_2$— | $R_3$— | Analytical Data |
|---|---|---|---|---|---|
| 3-1-8 | 2,4-dichloro-phenyl | $CH_3$ | 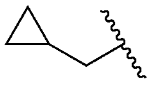 | 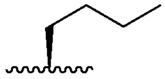 | Isomer 1 (syn): NMR ($^1H$, $CDCl_3$): δ 7.42(d, 1H), 7.37(d, 1H), 7.24 (dd, 1H), 4.24(m, 1H), 4.18(dd, 1H), 3.72(m, 1H), 3.53(m, 1H), 3.49(m, 1H), 3.06(dd, 1H), 2.38 (s, 3H), 2.32(m, 1H), 1.84(m, 1H), 1.74(m, 1H), 1.62(q, 1h), 1.45-1.25 (m, 4H), 1.02(m, 1H), 0.94(t, 3H), 0.52(m, 1H), 0.44(m, 1H), 0.38 (m, 1H), 0.30(m, 1H). MS (m/z): 431 $[M+H]^+$ (2 Cl). |
| | 2,4-dichloro-phenyl | $CH_3$ | 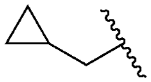 | 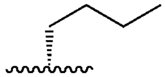 | Isomer 2 (anti): NMR ($^1H$, $CDCl_3$): δ 7.43(d1H), 7.39(d, 1H), 7.23 (dd, 1H), 4.27(m, 1H), 4.08(dd, 1H), 3.69(m, 1H), 3.57(m, 1H), 3.49(m, 1H), 2.99(dd, 1H), 2.39 (s, 3H), 2.24(m, 1H), 1.80-1.20 (m, 7H), 1.02(m, 1H), 0.94(t, 3H), 0.55(m, 1H), 0.46(m, 1H), 0.29 (m, 2H). MS (m/z): 431 $[M+H]^+$ 2Cl. |
| 3-1-9 | 2,4-dichloro-phenyl | $CH_3$ | 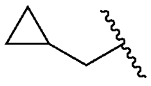 | 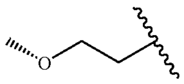 | NMR ($^1H$, Acetone-$d_6$): δ 7.55(d, 1H), 7.48(d, 1H), 7.37(d, 1H), 5.03(t, 1H), 4.25(t, 1H), 4.03(dd, 1H), 3.78(dd, 1H), 3.56(m, 3H), 3.15(dd, 1H), 2.54(m, 1H), 2.25 (s, 3H), 1.59(m, 2H), 1.43(td, 1H), 1.11(m, 1H), 0.92(t, 3H), 0.50-0.24(m, 4H). MS (m/z): 433 $[MH]^+$. |
| 3-1-10 | 2,4-dichloro-phenyl | $CH_3$ | 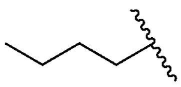 | 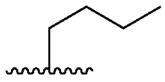 | NMR ($^1H$, $CDCl_3$): δ 7.54(d, 1H), 7.47(d, 1H), 7.36(dd, 1H), 4.39 (m, 1H), 4.19(m, 1H), 3.68(m, 1H), 3.59(m, 1H), 3.50(m, 1H), 3.07(m, 1H), 2.40(m, 1H), 2.20(s, 3H), 1.90-1.70(m, 3H), 1.60-1.50 (m, 3H), 1.40-1.20(m, 5H), 0.95 (2t, 6H). MS (m/z): 433 $[M+H]^+$ (2 Cl). |

Example 4

Synthesis of Representative Compounds of Structure (1-4)

5-(2,4-Dichlorophenyl-1-(1-ethylpropyl)-7-methyl-1,2,2a,3,4,5-hexahydro-1,6,8-triaza -acenaphthylene (4-1-1)

To a solution of intermediate 47 (22 mg, 0.062 mmol) in anh. MeOH (1 mL), under $N_2$, at r.t., was added 1-ethyl propylamine (9 μL, 1.25 eq) and the reaction mixture was stirred at r.t. for 1.25 hr. $NaBH_3CN$ 1.0M/THF (0.15 mL, 2.4 eq) was then added and the reaction mixture was stirred at r.t. for 2 hr, then at −18° C. for 4 days. The solvent was evaporated and the residue partitioned between EtOAc/$H_2O$. The phases were separated and the aqueous layer was extracted with EtOAc (3×5 mL). The combined organic extracts were washed with sat.aq. NaCl (1×5 mL) and dried over anh. $Na_2SO_4$. The solids were filtered and the solvent evaporated. The crude product was purified by flash chromatography (silica gel, cHex/EtOAc 9:1→8:2). The title compound was obtained as a clear oil (3 mg, 0.008 mmol, 12%).

All the analytical data are set forth in the following Table 4.

TABLE 4

(I-4)

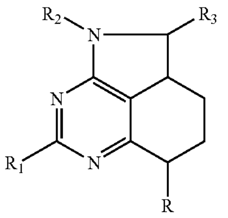

| Cpd. No. | R | $R_1$ | $R_2$— | $R_3$— | Analytical Data |
|---|---|---|---|---|---|
| 4-1-1 | 2,4-dichloro-phenyl | $CH_3$ | 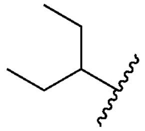 | H | MS (m/z): 390 $[MH]^+$ (2 Cl). |

Example 5

CRF Binding Activity

CRF binding affinity has been determined in vitro by the compounds' ability to displace $^{125}$I-oCRF and $^{125}$I-Sauvagine for CRF1 and CRF2 SPA, respectively, from recombinant human CRF receptors expressed in Chinese Hamster Ovary (CHO) cell membranes. For membrane preparation, CHO cells from confluent T-flasks were collected in SPA buffer (HEPES/KOH 50 mM, EDTA 2 mM; $MgCl_2$ 10 mM, pH 7.4.) in 50 mL centrifuge tubes, homogenized with a Polytron and centrifuged (50,000 g for 5 min at 4° C.: Beckman centrifuge with JA20 rotor). The pellet was resuspended, homogenized and centrifuged as before.

The SPA experiment has been carried out in Optiplate by the addition of 100 μL the reagent mixture to 1 μL of compound dilution (100% DMSO solution) per well. The assay mixture was prepared by mixing SPA buffer, WGA SPA beads (2.5 mg/mL), BSA (1 mg/mL) and membranes (50 and 5 μg of protein/mL for CRF1 and CRF2 respectively) and 50 pM of radioligand.

The plate was incubated overnight (>18 hr) at room temperature and read with the Packard Topcount with a WGA-SPA $^{125}$I counting protocol.

Example 6

CRF Functional Assay

Compounds of the invention were characterised in a functional assay for the determination of their inhibitory effect. Human CRF-CHO cells were stimulated with CRF and the receptor activation was evaluated by measuring the accumulation of cAMP.

CHO cells from a confluent T-flask were resuspended with culture medium without G418 and dispensed in a 96-well plate, 25'000 c/well, 100 μL/well and incubated overnight. After the incubation the medium was replaced with 100 μL of cAMP IBMX buffer warmed at 37° C. (5 mM KCl, 5 mM $NaHCO_3$, 154 mM NaCl, 5 mM HEPES, 2.3 mM $CaCl_2$, 1 mM $MgCl_2$; 1 g/L glucose, pH 7.4 additioned by 1 mg/mL BSA and 1 mM IBMX) and 1 μL of antagonist dilution in neat DMSO. After 10 additional minutes of incubation at 37° C. in a plate incubator without CO2, 1 μL of agonist dilution in neat DMSO was added. As before, the plate was incubated for 10 minutes and then cAMP cellular content was measured by using the Amersham RPA 538 kit.

All publications, including but not limited to patents and patent applications, cited in this specification are herein incorporated by reference as if each individual publication were specifically and individually indicated to be incorporated by reference herein as though fully set forth.

It is to be understood that the present invention covers all combinations of particular and preferred groups described herein above.

The application of which this description and claims forms part may be used as a basis for priority in respect of any subsequent application. The claims of such subsequent application may be directed to any feature or combination of features described herein. They may take the form of product, composition, process, or use claims and may include, by way of example and without limitation, the following claims:

The invention claimed is:

1. A compound of formula (I), or a pharmaceutically acceptable salt thereof:

(I)

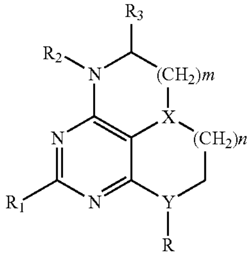

wherein

R is aryl or heteroaryl, wherein each of the above groups R may be substituted by 1 to 4 substituents independently selected from the group consisting of:

halogen, C1-C6 alkyl, C1-C6 alkoxy, halo C1-C6 alkyl, C2-C6 alkenyl, C2-C6 alkynyl, halo C1-C6 alkoxy, C1-C6 mono or dialkylamino, nitro, cyano and a group $R_4$;

$R_1$ is hydrogen, C1-C6 alkyl, C2-C6 alkenyl, C2-C6 alkynyl, halo C1-C6 alkyl, halo C1-C6 alkoxy, $NH_2$, halogen or cyano;

$R_2$ is hydrogen or $C(H)_n(R_5)_q(CH_2)_pZR_6$;

$R_3$ is hydrogen, C2-C6 alkenyl, C2-C6 alkynyl or $[CH(R_5)(CH_2)_p]_mZR_6$;

$R_4$ is C3-C7 cycloalkyl, which may contain one or more double bonds; aryl; or a 5-6 membered heterocycle;

wherein each of the above groups $R_4$ may be substituted by one or more groups selected from: halogen, C1-C6 alkyl, C1-C6 alkoxy, halo C1-C6 alkyl, C2-C6 alkenyl, C2-C6 alkynyl, halo C1-C6 alkoxy, C1-C6 mono or dialkylamino, nitro, and cyano;

$R_5$ is hydrogen, C2-C6 alkenyl, C2-C6 alkynyl or $(CH_2)_pZR_6$;

$R_6$ is C1-C6 alkyl, which may be substituted by one or more groups selected from halogen, halo C1-C6 alkyl, C2-C6 alkenyl, C2-C6 alkynyl, halo C1-C6 alkoxy, C1-C6 alkoxy, C1-C6 mono or dialkylamino, nitro, cyano and a group R4;

X is carbon;

Y is carbon or nitrogen;

m and n are independently 0 or 1;

p is 0 or an integer from 1 to 4;

q is 1 or 2; and

Z is a bond, O, NH or S.

2. A compound, according to claim 1, of formula (IIa)

(IIa)

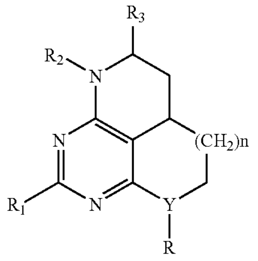

in which R, $R_1$, $R_2$, $R_3$, n and Y are defined as in claim 1 or a pharmaceutically acceptable salt thereof.

3. A compound, according to claim 1, of formula (IIb)

(IIb)

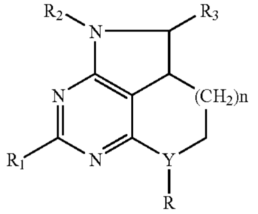

in which R, $R_1$, $R_2$, $R_3$, n and Y are defined as in claim 1.

4. A compound, according to claim 1, of formula (IIc)

(IIc)

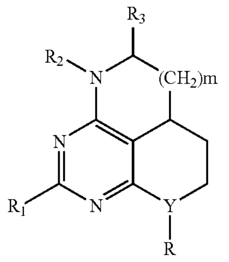

in which R, $R_1$, $R_2$, $R_3$, m and Y are defined as in claim 1 or a pharmaceutically acceptable salt thereof.

5. A compound, according to claim 1, of formula (IId)

(IId)

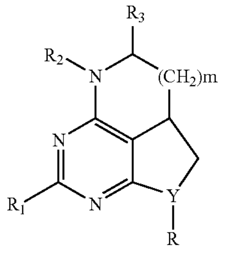

in which R, $R_1$, $R_2$, $R_3$, m and Y are defined as in claim 1 or a pharmaceutically acceptable salt thereof.

6. A compound, according to claim 4, of formula (Ia-1)

(Ia-1)

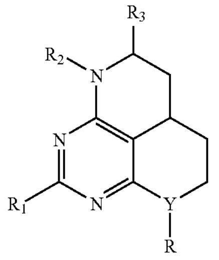

in which R, $R_1$, $R_2$, $R_3$ and Y are defined as in claim 1 or a pharmaceutically acceptable salt thereof.

7. A compound, according to claim 4, of formula (Ib-1)

(Ib-1)

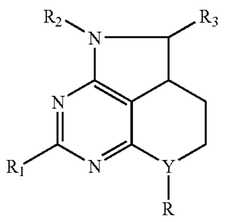

in which R, $R_1$, $R_2$, $R_3$ and Y are defined as in claim 1 or a phannaceutically acceptable salt thereof.

8. A compound, according to claim 2, of formula (Ic-1)

(Ic-1)

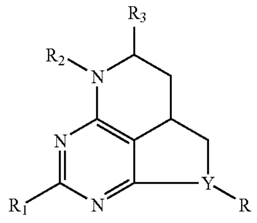

in which R, $R_1$, $R_2$, $R_3$ and Y are defined as in claim 1 or a pharmaceutically acceptable salt thereof.

9. A compound, according to claim 7, of formula (I-1), (I-1)

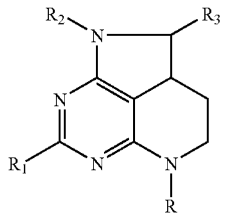

in which R, $R_1$, $R_2$, $R_3$ are defined as in claim 1 or a pharmaceutically acceptable salt thereof.

10. A compound, according to claim 6, of formula (I-2), (I-2)

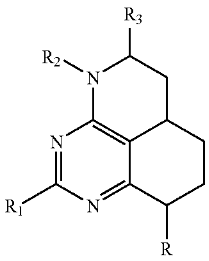

in which R, $R_1$, $R_2$, $R_3$ are defined as in claim 1 or a phannaceutically acceptable salt thereof.

11. A compound, according to claim 5, of formula (I-3), (I-3)

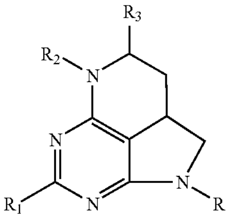

in which R, $R_1$, $R_2$, $R_3$ are defined as in claim 1 or a pharmaceutically acceptable salt thereof.

12. A compound, according to claim 7, of formula (I-4), (I-4)

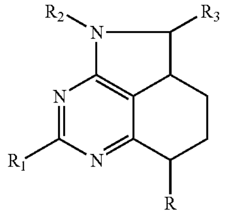

in which R, $R_1$, $R_2$, $R_3$ are defined as in claim 1 or a pharmaceutically acceptable salt thereof.

13. A compound, according to claim 1, wherein $R_2$ and $R_3$ are not simultaneously hydrogen; or a pharmaceutically acceptable salt thereof.

14. A compound, according to claim 1, wherein $R_1$ is C1-C3 alkyl group or halo C1-C3 alkyl group; or a phannaccutically acceptable salt thereof.

15. A compound, according to claim 1, wherein R is an aryl group selected from: 2,4-dichlorophenyl, 2-chloro-4-methylphenyl, 2-chloro-4-trifluoromethylphenyl, 2-chloro-4-methoxyphenyl, 2,4,5-trimethyiphenyl, 2,4-dimethyl-phenyl, 2-methyl-4-methoxyphenyl, 2-methyl-4-chlorophenyl, 2-methyl-4-trifluoromethylphenyl, 2,4-dimethoxyphenyl, 2-methoxy-4-trifluoromethylphenyl, 2-methoxy-4-chlorophenyl, 3-methoxy-4-chlorophenyl, 2,5-dimethoxy-4-chlorophenyl, 2-methoxy-4-isopropylphenyl, 2-methoxy-4-trifluoromethylphenyl, 2-methoxy-4-isopropylphenyl 2-methoxy-4-methylphenyl, 2-trifluoromethyl-4-chlorophenyl, 2,4-trifluoromethylphenyl, 2-trifluoromethyl-4-methylphenyl, 2-trifluoromethyl-4-methoxyphenyl, 2-bromo-4-isopropylphenyl, 4-methyl-6-dimethylaminopyridin-3-yl, 4-dimethylamino-6-methyl-pyridin-3-yl, 6-dimethylamino-pyridin-3-yl and 4-dimethylamino-pyridin-3-yl; or a pharmaceutically acceptable salt thereof.

16. A compound, according to claim 1, selected from the group consisting of:

5-(2,4-dichlorophenyl)-1-(1-ethylpropyl)-7-methyl-1,2,2a,3,4,5-hexahydro-1,5,6,8-tetraaza-acenaphthylene;

5-(2,4-dichlorophenyl)-1-(2-ethylbutyl)-7-methyl-1,2,2a,3,4,5,5a,8b-octahydro-1,5,6,8-tetraazaacenaphthylene;

5-(2,4-dichlorophenyl)-1-(2-methoxy-1-methoxymethyl-ethyl)-7-methyl-1,2,2a,3,4,5,5a,8b-octahydro-1,5,6,8-tetraazaacenaphthylene;

7-methyl-1-(1-propylbutyl)-5-[4-(1,1,2-trifluoroethyl)-2-trifluoromethylphenyl]-1,2,2a,3,4,5-hexahydro-1,5,6,8-tetraazaacenaphthylene;

7-methyl-1-(1-propylbutyl)-5-[4-(1,1,2-trifluoroethyl)-2-trifluoromethylphenyl]-1,2,2a(S),3,4,5-hexahydro-1,5,6,8-tetraazaacenaphthylene;

7-methyl-1-(1-propylbutyl)-5-[4-(1,1,2-trifluoroethyl)-2-trifluoromethylphenyl]-1,2,2a(R),3,4,5-hexahydro-1,5,6,8-tetraazaacenaphthylene;

5-(2,4-dichlorophenyl)-7-methyl-1-(1-propylbutyl)-1,2,2a,3,4,5-hexahydro-1,5,6,8-tetraazaacenaphthylene;

5-(2,4-dichlorophenyl)-7-methyl-1-(1-propylbutyl)-1,2,2a-(S),3,4,5,5a,8b-octahydro-1,5,6,8-tetraazaacenaphthylene;

5-(2,4-dichlorophenyl)-7-methyl-1-(1-propylbutyl)-1,2,2a-(R),3,4,5,5a,8b-octahydro-1,5,6,8-tetraazaacenaphthylene;

9-(2,4-dichlorophenyl)-4-(1-ethylpropyl)-2-methyl-5,6,6a,7,8,9-hexahydro-4H-1,3,4-triazaphenalene (isomer 1) and 9-(2,4-dichlorophenyl)-4-(1-ethylpropyl)-2-methyl-5,6,6a,7,8,9-hexahydro-4H-1,3,4-triazaphenalene (isomer 2);

5-cyclopropylmethyl-1-(2,4-dichlorophenyl)-7-methyl-1,2,2a,3,4,5-hexahydro-1,5,6,8-tetraazaacenaphthylene;

1-(2,4-dichlorophenyl)-5-(2-methoxyethyl)-7-methyl-1,2,2a,3,4,5-hexahydro-1,5,6,8-tetraazaacenaphthylene;

1-(2,4-dichlorophenyl)-5-(1-ethylpropyl)-7-methyl-1,2,2a,3,4,5-hexahydro-1,5,6,8-tetraazaacenaphthylene;

1-(2,4-dichlorophenyl)-5-(2-ethylbutyl)-7-methyl-1,2,2a,3,4,5-hexahydro-1,5,6,8-tetraazaacenaphthylene;

1-(2,4-dichlorophenyl)-7-methyl-5-(1-propylbutyl)-1,2,2a,3,4,5-hexahydro-1,5,6,8-tetraazaacenaphthylene;

7-methyl-5-(1-propylbutyl)-1-[4-(1,1,2-trifluoro-ethyl)-2-trifluoromethylphenyl]-1,2,2a,3,4,5-hexahydro-1,5,6,8-tetraazaacenaphthylene;

5-cyclopropylmethyl-1-(2,4-dichlorophenyl)-7-methyl-4-propyl-1,2,2a,3,4,5-hexahydro1,5,6,8-tetraazaacenaphthylene;

4-butyl-5-cyclopropylmethyl-1-(2,4-dichlorophenyl)-7-methyl-1,2,2a,3,4,5-hexahydro1,5,6,8-tetraazaacenaphthylene;

5-cyclopropylmethyl-1-(2,4-dichlorophenyl)-7-methyl-4-propoxy-1,2,2a,3,4,5-hexahydro1,5,6,8-tetraazaacenaphthylene;

4,5-dibutyl-1-(2,4-dichlorophenyl)-7-methyl-1,2,2a,3,4,5-hexahydro-1,5,6,8-tetraaza -acenaplithylene; and 5-(2,4-dichlorophenyl)-1-(1-ethylpropyl)-7-methyl-1,2,2a,3,4,5-hexahydro-1,6,8-triaza-acenaphthylene; or a pharmaceutically acceptable salt thereof.

17. A pharmaceutical composition comprising a compound according to claim 1, or a pharmaceutically acceptable salt thereof, in admixture with one or more physiologically acceptable carriers or excipients.

* * * * *